US011918610B2

(12) United States Patent
Tets et al.

(10) Patent No.: US 11,918,610 B2
(45) Date of Patent: Mar. 5, 2024

(54) METHODS FOR DIAGNOSIS AND TREATMENT OF TYPE 1 DIABETES

(71) Applicants: Viktor Veniaminovich Tets, New York, NY (US); Georgy Viktorovich Tets, New York, NY (US)

(72) Inventors: Viktor Veniaminovich Tets, New York, NY (US); Georgy Viktorovich Tets, New York, NY (US)

(73) Assignees: Viktor Veniaminovich Tets, New York, NY (US); Georgy Viktorovich Tets, New York, NY (US)

( * ) Notice: Subject to any disclaimer, the term of this patent is extended or adjusted under 35 U.S.C. 154(b) by 361 days.

(21) Appl. No.: 17/256,428

(22) PCT Filed: Jun. 28, 2019

(86) PCT No.: PCT/US2019/039732
§ 371 (c)(1),
(2) Date: Dec. 28, 2020

(87) PCT Pub. No.: WO2020/006357
PCT Pub. Date: Jan. 2, 2020

(65) Prior Publication Data
US 2021/0275600 A1  Sep. 9, 2021

Related U.S. Application Data

(60) Provisional application No. 62/737,029, filed on Sep. 26, 2018, provisional application No. 62/692,204, filed on Jun. 29, 2018.

(51) Int. Cl.
| *A61K 35/74* | (2015.01) |
| *A61K 31/65* | (2006.01) |
| *A61K 31/7004* | (2006.01) |
| *A61K 33/06* | (2006.01) |
| *A61K 35/745* | (2015.01) |
| *A61K 35/747* | (2015.01) |
| *A61K 35/76* | (2015.01) |
| *A61K 38/08* | (2019.01) |
| *A61K 38/17* | (2006.01) |
| *A61K 38/46* | (2006.01) |
| *A61K 39/00* | (2006.01) |
| *A61K 39/108* | (2006.01) |
| *A61P 3/10* | (2006.01) |
| *C07K 16/12* | (2006.01) |
| *C12N 15/113* | (2010.01) |
| *C12Q 1/6883* | (2018.01) |

(52) U.S. Cl.
CPC ............ *A61K 35/74* (2013.01); *A61K 31/65* (2013.01); *A61K 31/7004* (2013.01); *A61K 33/06* (2013.01); *A61K 35/745* (2013.01); *A61K 35/747* (2013.01); *A61K 35/76* (2013.01); *A61K 38/08* (2013.01); *A61K 38/1709* (2013.01); *A61K 38/465* (2013.01); *A61K 39/0258* (2013.01); *A61P 3/10* (2018.01); *C07K 16/1232* (2013.01); *C12N 15/113* (2013.01); *C12Q 1/6883* (2013.01); *A61K 2039/505* (2013.01); *C12N 2310/14* (2013.01); *C12Q 2600/118* (2013.01); *C12Q 2600/156* (2013.01)

(58) Field of Classification Search
CPC ...................................................... A61K 35/74
See application file for complete search history.

(56) References Cited

U.S. PATENT DOCUMENTS

| 5,955,287 A | 9/1999 | Fernandez-Pol |
| 6,201,104 B1 | 3/2001 | MacDonald et al. |
| 6,528,269 B1 | 3/2003 | Sy et al. |
| 9,063,141 B2 | 6/2015 | Grallert et al. |
| 2002/0012927 A1 | 1/2002 | Burmer et al. |
| 2005/0124794 A1 | 6/2005 | McCrae et al. |
| 2006/0233780 A1 | 10/2006 | Genkin et al. |
| 2006/0263767 A1 | 11/2006 | Castrillon et al. |
| 2007/0221559 A1 | 9/2007 | Wang |
| 2013/0183284 A1 | 7/2013 | Genkin et al. |

(Continued)

FOREIGN PATENT DOCUMENTS

| CA | 2628552 A1 | 5/2007 |
| HU | 0100159 A2 * | 5/2001 |

(Continued)

OTHER PUBLICATIONS

Gianchecchi et al., Immunol/ Res, 2017; 65:242-256 (Year: 2017).*

(Continued)

*Primary Examiner* — Brian Gangle
*Assistant Examiner* — Lakia J Jackson-Tongue
(74) *Attorney, Agent, or Firm* — Troutman Pepper Hamilton Sanders LLP

(57) ABSTRACT

Methods for preventing, treating or diagnosing Type 1 Diabetes (T1D) are described. Amyloid-producing bacteria within microbiota are inactivated. Amyloid-producing bacteria are inactivated in microbiota, gastrointestinal tract, bodily fluids or tissues. Type-1 Diabetes associated microbial product production or release by microbiota is prevented. Also described is inactivation of bacteria-derived T1DAMP present in microbiota, bodily fluids or tissues of a mammal. Release of bacteria-derived T1DAMP from biofilm or bacteria to gastrointestinal tract is inhibited. Entry of bacteria-derived T1DAMP to microbiota, gastrointestinal tract, bodily fluids or tissues of a mammal is inhibited.

11 Claims, 8 Drawing Sheets

Specification includes a Sequence Listing.

(56) References Cited

U.S. PATENT DOCUMENTS

| | | | |
|---|---|---|---|
| 2013/0203849 A1 | 8/2013 | Ben Yehuda | |
| 2014/0234260 A1 | 8/2014 | Borody | |
| 2014/0271701 A1* | 9/2014 | Sechi | C07K 16/28 514/250 |
| 2017/0020937 A1 | 1/2017 | Mattey et al. | |

FOREIGN PATENT DOCUMENTS

| | | | |
|---|---|---|---|
| WO | WO2019/028456 | * | 2/2013 |
| WO | 2016190780 A1 | | 12/2016 |
| WO | 2017042831 A2 | | 3/2017 |
| WO | 2017118924 A1 | | 7/2017 |

OTHER PUBLICATIONS

Vaarala et al., Diabetes, 2008; 57: 2555-2562 (Year: 2008).*

Google patent translation of HU0100159A2 (Year: 2001).*

Supplementary European Search Report dated Feb. 9, 2022 in connection with EP Application No. 19826448.

Gianchecchi E. et al., "On the pathogenesis of insulin-dependent diabetes mellitus: the role of microbiota", Immunologic Research, Humana Press, Inc. US, vol. 65, No. 1, Jul. 16, 2016, pp. 242-256.

Vaarala O. et al., "The Perfect Storm" for Type 1 Diabetes: The Complex Interplay Between Intestinal Microbiota, Gut Permeability, and Mucosal Immunity, Diabetes, vol. 57, No. 10, Sep. 26, 2008, pp. 2555-2562.

Kosiewicz M. et al., "Relationship between gut microbiota and development of T cell associated disease", Febs Letters, Elsevier Amsterdam, NL, vol. 588, No. 22, Mar. 26, 2014, pp. 4195-4206.

Communication (International Search Report) mailed in International Application No. PCT/US19/39732 dated Nov. 6, 2019, 5 pages total.

Communication (Written Opinion) mailed in International Application No. PCT/US19/39732 dated Nov. 6, 2019, 9 pages total.

Gallo, P.M. et al., "Amyloid-DNA Composites of Bacterial Biofilms Stimulate Autoimmunity" Immunity (2015) vol. 42, No. 6, pp. 1171-1184.

Newby, B.N., "Type 1 Inteferons Promote a Diabetogenic Microenvironment in Type 1 Diabetes" (2017) University of Florida, 150 pages total.

Tetz, G. et al., "Bacteriophages as New Human Viral Pathogens" Microrganisms (2018) vol. 6, No. 2, 12 pages total.

Tursi, S.A. et al., "Bacterial Amyloid Curli Acts as a Carrier for DNA to Elicit an Autoimmune Response via TLR2 and TLR9" PLOS Pathogens (2017) vol. 13, No. 4, 25 pages total.

Zaccone, P. et al., "Salmonella Typhirnurium Infection Halts Developmen of Type 1 Diabetes in NOD Mice, Inflammation and Innate Immunity" Eur. J. Immunol. (2004) vol. 34, No. 11, pp. 3246-3256.

Aviv, O. et al., "Poly(hexamethylene guanidine)-poly(ethylene glycol) Solid Blend for Water Microbial Deactivation" Polymer Degradation and Stability (2016) vol. 129, pp. 1-21.

Bille, E. et al., "Association of a Bacteriophage with Meningococcal Disease in Young Adults" PLoS One (2008) vol. 3, Issue 12, 6 pages total.

Communication (International Preliminary Report on Patentability) issued by the International Searching Authority in International Application No. PCT/US2018/028640 dated Nov. 26, 2019, 19 pages total.

Communication (International Preliminary Report on Patentability) mailed in International Application No. PCT/ JS19/39732 dated Dec. 29, 2020, 10 pages total.

Communication (International Search Report) issued by the International Searching Authority in International Application No. PCT/US2018/028640 dated Sep. 4, 2018, 8 pages total.

Communication (Written Opinion) issued by the International Searching Authority in International Application No. PCT/US2018/028640 dated Sep. 4, 2018, 18 pages total.

Costa, L. et al., "Photodynamic Inactivation of Mammalian Viruses and Bacteriophages" Viruses (2012) vol. 4, pp. 1034-1075.

De Haard, H.J.W. et al., "Llama Antibodies Against a Lactococcal Protein Located at the Tip of the Phage Tail Prevent Phage Infection" Journal of Bacteriology (2005) vol. 187, No. 13, pp. 4531-4541.

De Paepe, M. et al., "Bacteriophages: An Underestimated Role in Human and Animal Health?" Frontiers in Cellular and Infection Microbiology (2014) vol. 4, Article 39, 11 pages total.

European Communication (Extended European Search Report) issued by the European Patent Office in European Application No. 18805942.2 dated Apr. 22, 2021, 13 pages total.

European Communication (pursuant to Rule 164(1) EPC) issued by the European Patent Office in European Application No. 18805942.2 dated Jan. 22, 2021, 16 pages total.

Findley, K. et al., "The Skin Microbiome: A Focus on Pathogens and Their Association with Skin Disease" PLoS One (2014) vol. 10, No. 10, pp. 1-3.

Galtier, M. et al., "Bacteriophages to Reduce Gut Carriage of Antibiotic Resistant Uropathogens with Low Impact on Microbiota Composition" Environmental Microbiology (2016) vol. 18, No. 7, pp. 2237-2245.

Garneau, JE et al., "The CRISPR/Cas Bacterial immune System Cleaves Bacteriophage and Plasmid DNA" Nature (2010) vol. 468, No. 7320, pp. 67-71.

Horwich, A. et al., "Protein aggregation in disease: a role for folding intermediates forming specific multimeric Interactions" Journal of Clinical Investigation, Nov. 2002, vol. 110, No. 9, pp. 1221-1232.

Santiago-Rodriguez, T.M. et al., "Transcriptome Analysis of Bacteriophage Communities in Periodontal Health and Disease" BMC Genomics (2015) vol. 16, No. 549, 9 pages total.

Shukla, G.S. et al., "Intravenous Infusion of Phage-Displayed Antibody Library in Human Cancer Patients: Enrichment and Cancer-Specificity of Tumor-Homing Phage-Antibodies" Cancer Immunology, Immunotherapy (2013) vol. 62, No. 8, pp. 1-14.

Tetz, G. et al., "Bacteriophage Infections of Microbiota can Lead to Leaky Gut in an Experimental Rodent Model" Gut Pathogens (2016) vol. 8, No. 33, pp. 1-4.

Tetz, G. et al., "Bacteriophages as Potential New Mammalian Pathogens" Scientific Reports (2017) vol. 7, No. 7043, 9 pages total.

Tetz, G. et al., "Parkinson's Disease and Bacteriophages as its Overlooked Contributors" Scientific Reports (2018) vol. 8, No. 10812, 11 pages total.

Tetz, G. et al., "Type 1 Diabetes: an Association Between Autoimmunity, the Dynamics of Gut Amyloid-producing E. coli and Their Phages" bioRxiv (2018) 433110, doi: https://doi.org/10.1101/433110, 31 pages total.

Wagner, J. et al., "Bacteriophages in Gut Samples from Pediatric Crohn's Disease Patients: Metagenomic Analysis Using 454 Pyrosequencing" HHS Public Access Author Manuscript (2013) vol. 19, No. 8, pp. 1598-1608.

Zaczek, M. et al., "Antibody Production in Response to Staphylococcal MS-1 Phage Cocktail in Patients Undergoing Phage Therapy" Frontiers in Microbiology (2016) vol. 7, No. 1681, pp. 1-14.

Office Action dated Jul. 13, 2022 in connection with U.S. Appl. No. 16/616,231.

M. Dupon, et al., "Plasma levels of piperacillin and vancomycin used as prophylaxis in liver transplant patients", Eur J Clin Pharmacol (1993) 45:529-534.

Office Action dated Apr. 24, 2023 in connection with U.S. Appl. No. 16/616,231.

Anderson et al., "Enumeration of bacteriophage particles" Bacteriophage 1(2):86-93 (2011).

Castilla et al., "In Vitro Generation of Infectious Scrapie Prions,"Cell, Apr. 22, 2005, vol. 121, pp. 195-206.

Cordeiro et al., "DNA Converts Cellular Prion Protein in the ß-Sheet Conformation and Inhibits Prion Peptide Aggregation," The Journal of Biological Chemistry, Dec. 28, 2001, vol. 276, No. 52, pp. 49400-49409.

Prusiner, S. "Biology and Genetics of Prions Causing Neurodegeneration," Annual Review of Genetics, Nov. 23, 2013, vol. 47, pp. 601-623.

(56) References Cited

OTHER PUBLICATIONS

Kipkorir et al., "Highly Infectious CJD Particles Lack Prion Protein but Contain Many Viral-Linked Peptides by LC-MS/MS," Journal of Cellular Biochemistry, Jun. 16, 2014, vol. 115, No. 11, pp. 2012-2221.
Tetz et al., "Prion-like Domains in Eukaryotic Viruses," Scientific Reports, Jun. 12, 2018, vol. 8, pp. 1-10.
Tetz et al., "Bacterial DNA Induces the Formation of Heat-Resistant Disease-Associated 'Tezt-Proteins' in Human Plasma," bioRxiv, Apr. 9, 2019, pp. 1-24.
Tetz et al., "Effect of Deoxyribonuclease I Treatment for Dementia in End-Stage Alzheimer's Disease: a Case Report," Journal of Medical Case Reports, May 28, 2016, vol. 10, No. 1, pp. 1-3.
Written Opinion dated Jul. 23, 2019, issued in connection with international Application No. PCT/US2019/026272, 18 pages total.
International Search Report dated Jul. 23, 2019, issued in connection with international Application No. PCT/US2019/026272, 6 pages total.
International Report on Patentability dated Nov. 3, 2020, issued in connection with international Application No. PCT/US2019/026272, 19 pages total.
Supplementary Partial European Search Report dated Feb. 2, 2022 in connection with EP Application No. 19796997.
March Z. M. et al., "Prion-like domains as epigenetic regulators, scaffolds for subcellular organization, and drivers of neurodegenerative disease", Brain Research, Elsevier, Amsterdam, NL, vol. 1647, Mar. 19, 2016, pp. 9-18.
Kovachev et al., "Distinct modulatory role of RNA in the aggregation of the tumor suppressor protein p53 core domain", Journal of Biological Chemistry, vol. 292, No. 22, Apr. 18, 2017, pp. 9345-9357.
O'Toole, P.W. et al., "Gut Microbiota and Aging" Science (2015) vol. 350, No. 6265, pp. 1214-1215, XP055669176.
Petrascheck, M. et al., "Computational Analysis of Lifespan Experiment Reproducibility" Frontiers in Genetics (2017) vol. 8, No. 92, pp. 1-11, XP055669171.
Pitchaimani, M. et al., "Maximum Life Span Predictions Using the Gompertz Tumour Growth Model" IOSR Journal of Mathematics (2014) vol. 10, Issue 6, pp. 55-62, XP055669182.
Tetz, G. et al., "Tet's Theory and Law of Longevity" Theory in Biosciences (2018) vol. 137, No. 2, pp. 145-154.
European Communication (Extended European Search Report) issued by the European Patent Office in European Application No. 19830501.3 dated Mar. 10, 2022, 11 pages total.
Jonas Zierer et al., "Integration of "omics"data in aging research: from biomarkers to systems biology", Aging Cell, vol. 14, No. 6, Aug. 30, 2015, pp. 933-944, XP055766774, GB issn: 1474-9718, DOI: 10.1111/acel.12386.
Garagnani P. et al., "The Three Genetics (Nuclear DNA, Mitochondrial DNA, and Gut Microbiome) of Longevity in Humans Considered as Metaorganisms", Biomed Research Int, vol. 2014, (Jan. 1, 2014), pp. 1-14, XP055896304, ISSN: 2314-6133, DOI: 10.1155/2014/560340.
Dato Serena et al, "The genetics of human longevity: an intricacy of genes, environment, culture and microbiome", Mechanisms of Ageing and Development, (Jul. 1, 2017), vol. 165, doi: 10.1016/J.MAD.2017.03.011, ISSN 0047-6374, pp. 147-155, XP085162845.
Xian Xia et al., "Molecular and phenotypic biomarkers of aging", F1000RESEARCH, (Jan. 1, 2017), vol. 6, pp. 1-10 doi:10.12688/f1000research. 10692.1, 860, XP055388474.
Santoro Aurelia et al, "Gut microbiota changes in the extreme decades of human life: a focus on centenarians", CMLS Cellular and Molecular Life Sciences, Birkhauser Verlag, Heidelberg, DE, vol. 75, No. 1, doi:10.1007/S00018-017-2674-Y, IsSN 1420-682X, (Oct. 14, 2017), pp. 129-148, (Oct. 14, 2017), XP036389430.
Elena Biagi et al, "Gut Microbiota and Extreme Longevity", Current Biology, GB, (Jun. 1, 2016), vol. 26, No. 11, doi:10.1016/j.cub.2016.04.016, ISSN 0960-9822, pp. 1480-1485, XP055683144.
Office Action dated Jun. 29, 2023 in connection with U.S. Appl. No. 17/257,389.
Palma et al., "Dietary water affects human skin hydration and biomechanics", Clinical Cosmetic and Investigational Dermatology, 2015, 413-421.
Janeway C. A. et al., "The complement system and innate immunity—Immunology—NCBI Bookshelf" In: Immunobiology: The Immune System in Health and Disease, Jan. 1, 2001, Garland Science, New York, pp. 1-14.
Sim et al., "Nucleophilic compounds acting on C3 and C4", Activators and Inhibitors of Complement, Springer Netherlands, Dordrecht, pp. 107-125, Oct. 31, 1992.
Fernandez-Pol Alberto J. et al., "Genomics, Proteomics and Cancer: Specific Ribosomal, Mitochondrial, and Tumor Reactive Proteins Can Be Used as Biomarkers for Early Detection of Breast Cancer in Serum", Cancer Genomics & Proteomics, vol. 2, No. 1, Jan. 1, 2005, pp. 1-24.
Communication (International Preliminary Report on Patentability) mailed in International Application No. PCT/US19/40524 dated Jan. 14, 2021, 12 pages total.
Biagi, E. et al., "Through Ageing and Beyond: Gut Microbiota and Inflammatory Status in Seniors and Centenarians" (2010) PLoS One vol. 5, Issue 5, pp. 1-14.
Claesson, M.J. et al., "Gut Microbiota Composition Correlates with Diet and Health in the Elderly" Nature (2012) vol. 488, No. 7410, pp. 178-184.
Communication (International Search Report) mailed in International Application No. PCT/US19/40524 dated Nov. 18, 2019, 9 pages total.
Communication (Written Opinion) mailed in International Application No. PCT/US19/40524 dated Nov. 18, 2019, 10 pages total.
Juge, R. et al., "Shift in Skin Microbiota of Western European Women Across Aging" Journal of Applied Microbiology (2018) vol. 125, No. 3, pp. 907-916.
Jylhava, J. et al., "Biological Age Predictors" EBioMedicine (2017) vol. 21, pp. 29-36.
Lepage, P. et al., "Dysbiosis in Inflammatory Bowel Disease: A Role for Bacteriophages?" Gut Microbiota (2008) vol. 57, No. 3, pp. 424-425.
Mirzaei, MK et al., "Isolation of Phages for Phage Therapy: A Comparison of Spot Tests and Efficiency of Plating Analyses for Determination of Host Range and Efficacy" PLOS One (2015) vol. 10, No. 3, pp. 1-13.

\* cited by examiner

METHODS FOR DIAGNOSIS AND TREATMENT OF TYPE 1 DIABETES

CROSS-REFERENCE TO RELATED APPLICATIONS

This application is a U.S. National Phase of International Patent Application No. PCT/US2019/039732, filed on Jun. 28, 2019, which published as WO 2020/006357 A1 on Jan. 2, 2020, and claims priority to U.S. Provisional Application No. 62/692,204, filed on Jun. 29, 2018, and U.S. Provisional Application No. 62/737,029, filed Sep. 26, 2018, both of which application are herein incorporated by reference in their entireties.

SEQUENCE LISTING

The instant application contains a Sequence Listing which has been submitted electronically in ASCII format and is hereby incorporated by reference in its entirety. Said ASCII copy, created on Jun. 27, 2019, is named 244008_000126_sequence_list_ST25.TXT and is 16,467 bytes in size.

FIELD OF THE INVENTION

Provided herein are methods for preventing, treating or diagnosing Type 1 Diabetes (T1D). Prevention and treatment methods comprise (i) inactivation of amyloid-producing bacteria within microbiota and/or (ii) inactivation of amyloid-producing bacteria getting from the outer environment to microbiota, gastrointestinal tract, bodily fluid(s) or tissue(s) of a mammal and/or (iii) inactivation of Type-1 Diabetes associated microbial product (T1DAMP) production/release by microbiota and/or (iv) inactivation of bacteria-derived T1DAMP present in microbiota, bodily fluid(s) or tissue(s) of a mammal and/or (v) inhibiting release of bacteria-derived T1DAMP from biofilm and/or bacteria to gastrointestinal tract, bodily fluid(s) or tissue(s) of a mammal and/or (vi) inhibiting entry of bacteria-derived T1DAMP to microbiota, gastrointestinal tract, bodily fluid(s) or tissue(s) of a mammal and/or (vii) inhibiting effect of bacteria-derived T1DAMP and/or its complexes to trigger T1D.

BACKGROUND OF THE INVENTION

The microbiota of the human intestinal tract is comprised of bacteria, fungi, and viruses, including bacteriophages. This highly diverse and complex ecosystem is characterized by dynamic stability of each of its components in the context of the host organism. The human gut contains approximately $10^{13}$ bacteria, which >10 times of the number of human cells (Dalmasso, M. et al., 2014).

Growing evidence suggests that alterations of the intestinal microbiota are critical pathogenic factors that trigger various polyaetiological diseases associated with increased intestinal permeability and chronic inflammation (Bosi E. et al., 2006; Vaarala O et al., 2008).

Intestinal barrier dysfunction or disruption, known as "leaky gut" syndrome, is characterized by the translocation of macromolecules, bacteria or their toxins to the lamina propria, which is implicated in the pathogenesis of numerous diseases (Maes M. et al., 2012). An abnormally permeable mucosal barrier is associated with various pathologies including inflammatory bowel disease, Crohn's disease, neurodegenerative diseases, diabetes type 1, some types of cancers, cardiovascular disorders, rheumatoid arthritis, etc. (Tlaskalova-Hogenová, H. et al., 2011; Berk, M. et al., 2013 Fasano 2012).

Bacteria in the human gut live within surface-associated microbial communities named biofilms, which are characterized by the presence of self-produced extracellular matrix (ECM) and surface film that protect microorganisms for the outer environment (Costerton et al., 1999). ECM consists of different biomolecules including extracellular nucleic acids, polysaccharides and proteins, and several microorganisms within human microbiome predominantly among the members of Enterobactericeae family possess amyloid proteins that can form so called curli fibers within ECM as well that provide them with unique mechanical properties and representing an important step during biofilm formation (Gallo, P. M. et al., 2015).

Type 1 Diabetes (T1D) is an autoimmune disorder driven by T cell-mediated destruction of the insulin-secreting β-cells of the pancreatic islets that often manifests during childhood. There are many factors associated with the development of T1D, and the susceptibility to T1D is conferred by a combination of genetic and environmental factors. The strongest susceptibility alleles for T1D are certain human leukocyte antigens (HLA), which determine a central role for autoreactive T cells in pathogenesis. The major genetic determinants of T1D are polymorphisms of class II HLA genes inherited from both parents that are the key for the development of T1D predisposing over 60% of its familial clustering. However only around 10% of children carrying HLA risk alleles will develop T1D, which indicates a large role of nongenetic environmental factors in the initiation of disease (Noble et al, 2011; Knip et al., 2005).

T1D usually has a long pre-diabetic period, named seroconversion. Seroconversion is characterized by the presence of autoantibodies to antigens of the pancreatic β cells or insulin without progression to T1D. A few factors are explored as triggers of the seroconversion; however what they have in common is that they lead to the death of islet cells, which in turn leads to formation of β-cell antigens, activation of dendric cells (DC) and antigen presentation.

SUMMARY OF THE INVENTION

There is a need in to develop methods for prophylaxis, therapy and diagnosis of T1D. The present invention addresses these and other needs by providing methods and compositions for reducing the exposure of host organism to bacterial amyloid.

In one aspect is provided a method for preventing or treating Type 1 Diabetes (T1D) or consequences thereof in a mammal in need thereof, said method comprising one or more of (i) inactivating amyloid-producing bacteria within microbiota in the mammal, (ii) preventing amyloid-producing bacteria from entering the microbiota, the gastrointestinal tract, a bodily fluid or a tissue of the mammal from an environment outside the mammal, (iii) inactivating a T1D-associated microbial product (T1DAMP) that is released by microbiota of the mammal, (iv) inactivating a T1DAMP present, a bodily fluid or a tissue of the mammal, (v) inhibiting release of a T1DAMP from a biofilm and/or bacteria in the gastrointestinal tract, a bodily fluid or a tissue of the mammal, (vi) inhibiting entry of T1DAMP to microbiota, the gastrointestinal tract, a bodily fluid or a tissue of the mammal, (vii) inhibiting the triggering of T1D by bacteria, T1DAMP derived from the bacteria, or a complex comprising the bacteria or the T1DAMP, (viii) administering to the mammal *E. coli* that do not produce an amyloid protein, (ix) administering to the mammal a pilocene or a curlicide, and (x) inhibiting the activity of a bacteriophage (xi)) inhibiting the prophage inductors.

In some embodiments, the mammal expresses a T1D susceptible HLA allele.

In some embodiments, the T1D susceptible HLA allele is selected from an HLA allele having a DR4-DQ8 and/or DRB1 haplotype, an HLA allele having a DR3-DQ2 haplotype, HLA allele DQB1*02/*0302-DRB1*0404, HLA allele DQB1*0302/*0501-DRB1*0401, and DQB1*0302/*04-DRB1*0401*.

In some embodiments, the mammal comprises an increased amount of *E. coli* or *Salmonella* in the gastrointestinal tract as compared to a second mammal that does not develop T1D, and optionally wherein the mammal and the second mammal both express a T1D susceptible HLA allele, and optionally wherein the mammal and the second mammal both express the same T1D susceptible HLA allele.

In some embodiments, the second mammal is age-matched and/or gender-matched to the mammal comprising the increased amount of *E. coli* or *Salmonella* in the gastrointestinal tract.

In some embodiments, the method comprises administering to the mammal *E. coli* in a manner effective to populate the microbiota with the *E. coli*, wherein the administered *E. coli* do not produce an amyloid protein or produce a reduced amount of the amyloid protein as compared to a wild-type *E. coli*.

In some embodiments, the administered *E. coli* comprises a mutation in a gene encoding for an amyloid protein.

In some embodiments, the method comprises administering to the mammal *E. coli* that comprises a mutation in a sequence regulating expression of a gene encoding for an amyloid protein.

In some embodiments, inactivation of amyloid-producing bacteria within microbiota comprises preventing transfer of amyloid-producing bacteria to the mammal from a mother of the mammal during birth or breastfeeding.

In some embodiments, the inactivation of amyloid-producing bacteria within microbiota comprises administering to the mammal a microorganism or a by-product of the microorganism, wherein the microorganism or the byproduct is effective to prevent colonization of the amyloid-producing bacteria in the gastrointestinal tract of the mammal.

In some embodiments, the microorganism is from an order selected from Bacteroidales, Lactobacillales, Erysipelotrichales, Coriobacteriales, Clostridiales, Bacillales, and Bifidobacteriales.

In some embodiments, the microorganism is a non-amyloid-producing strain of bacteria or a strain of bacteria that synthesizes a reduced amount of amyloid.

In another aspect is provided a method for preventing or treating Type 1 Diabetes (T1D) or consequences thereof in a mammal in need thereof, the method comprising vaccination of the mammal against Enterobacteriales bacteria.

In some embodiments, the method further comprises vaccination of the mammal against *E. coli* or *Salmonella*.

In some embodiments, the method further comprises vaccination of the mammal against Enterobacteriales bacteria.

In some embodiments, the method further comprises vaccination of the mammal against *E. coli* or *Salmonella*.

In some embodiments, the inactivation of amyloid-producing bacteria within microbiota comprises i) colonization of gastrointestinal microbiota of the mammal with non-amyloid-producing bacteria and/or ii) administering an anti-amyloid antibody to the mammal.

In some embodiments, the inactivation of amyloid-producing bacteria within microbiota comprises editing one or more genes in the genome of the amyloid-producing bacteria, wherein the inactivation inhibits adhesion of the amyloid-producing bacteria, wherein the one or more genes are selected from afa-dra, daaD, tsh, vat, ibeA, fyuA, mat, sfa-foc, malX, plc, irp2, papC, fimH; PapAH papEF, bmaE, sfa/focDE, papC, focG, sfaI, sfa II, sfaS, aah, aidA, fasA, faeG, bfpA, eaeA, Paa, fasA, faeG, fedA, fanC, sfaY, and a gene in the Cpx pathway.

In some embodiments, the inactivation of the amyloid-producing bacteria within microbiota comprises administering to the mammal a composition comprising one or more of fosfomycin, Doxycycline, Ciprofloxacin, Trimethoprim/sulfamethoxazole, Levofloxacin, Amoxicillin, Aztreonam, Nitrofurantoin, Ceftriaxone, imipenem, and Rifaximin, a FimH antagonist, and a pilicide.

In some embodiments, the FimH antagonist is an n-Heptyl α-D-mannose glycopolymer, methyl R-D-mannoside, or a thiazolylmannoside.

In some embodiments, the pilicide is
i) 7-(1-naphthylmethyl)-5-oxo-8-phenyl-2,3,6,7-tetrahydro-5H-[1,3]thiazolo[3,2-a]pyridine-3-carboxylic acid
ii) 8-cyclopropyl-7-(1-naphthylmethyl)-5-oxo-2,3,6,7-tetrahydro-5H-[1,3]thiazolo[3,2-a]pyridine-3-carboxylic acid
iii) 7-(1-naphthylmethyl)-5-oxo-8-pentyl-2,3,6,7-tetrahydro-5H-[1,3]thiazolo[3,2-a]pyridine-3-carboxylic acid
iv) 8-(4-bromophenyl)-7-(1-naphthylmethyl)-5-oxo-2,3,6,7-tetrahydro-5H-[1,3]thiazolo[3,2-a]pyridine-3-carboxylic acid
v) 7-(1naphthylmethyl)-5-oxo-8-phenyl-2,3-dihydro-5H-[1,3]thiazolo[3,2-a]pyridine-3-carboxylic acid, lithium salt
vi) 8-cyclopropyl-7-(1-naphthylmethyl)-5-oxo-2,3-dihydro-5H-[1,3]thiazolo[3,2-a]pyridine-3-carboxylic acid, lithium salt
vii) 7-methyl-5-oxo-8-phenyl-2,3-dihydro-5H-[1,3]thiazolo[3,2-a]pyridine-3-carboxylic acid, lithium salt
viii) 6-dimethylaminomethyl-7-(1-naphthylmethyl)-5-oxo-8-phenyl-2,3-dihydro-5H-[1,3]thiazolo[3,2-a]pyridine-3-carboxylic acid, lithium salt
ix) 6-morpholinomethyl-7-(1-naphthylmethyl)-5-oxo-8-phenyl-2,3-dihydro-5H-[1,3]thiazolo[3,2-a]pyridine-3-carboxylic acid, lithium salt
x) 8-cyclopropyl-6-morpholinomethyl-7-(1-naphthylmethyl)-5-oxo-2,3-dihydro-5H-[1,3]thiazolo[3,2-a]pyridine-3-carboxylic acid, lithium salt, or
xi) 6-dimethylaminomethyl-7-methyl-5-oxo-8-phenyl-2,3-dihydro-5H-[1,3]thiazolo[3,2-a]pyridine-3-carboxylic acid, lithium salt.

In some embodiments, the mammal expresses one or more of T1D-susceptible HLA alleles.

In some embodiments, the T1D-susceptible HLA allele is a DR4-DQ8 haplotype, an HLA allele having a DR3-DQ2 haplotype, HLA allele DQB1*02/*0302-DRB1*0404, HLA allele DQB1*0302/*0501-DRB1*0401, and DQB1*0302/*04-DRB1*0401*.

In some embodiments, the method comprises (i) inactivating amyloid-producing bacteria within microbiota in the mammal, and wherein the microbiota is gut microbiota.

In some embodiments, the method comprises (iii) inactivating a T1D-associated microbial product (T1DAMP) that is released by microbiota of the mammal, and wherein the microbiota is gut microbiota.

In some embodiments, the method comprises (vi) inhibiting entry of T1DAMP to microbiota, the gastrointestinal tract, a bodily fluid or a tissue of the mammal, (vii) inhibiting the triggering of T1D by bacteria, T1DAMP derived from the bacteria, or a complex comprising the bacteria or the T1DAMP, and wherein the microbiota is gastrointestinal microbiota.

In another aspect is provided a method for determining susceptibility to T1D in a mammal, the method comprising
(a) detecting the expression in the mammal of at least one T1D susceptible HLA allele, and
(b) (i) detecting increased intestinal permeability in the mammal as compared to the intestinal permeability in one or more mammals from an age-matched and sex-matched reference population, and/or (ii) detecting an increased level of *E. coli* or *Salmonella* in gastrointestinal microbiota of the mammal, wherein the *E. coli* or *Salmonella* release a T1D-associated microbial product (T1DAMP) that enters the bloodstream of the mammal and binds to a β-cell or dendritic cells expressing a Toll-like 2 receptor or a Toll-like 9 receptor and promotes death of the β-cell to thereby increase susceptibility to T1D.

In some embodiments, the T1D susceptible HLA allele is selected from an HLA allele having a DR4-DQ8 haplotype, an HLA allele having a DR3-DQ2 haplotype, HLA allele DQB1*02/*0302-DRB1*0404, HLA allele DQB1*0302/*0501-DRB1*0401, and HLA allele DQB1*0302/*04-DRB1*0401*.

In some embodiments, the detection of an increased level of *E. coli* comprises performing one or more of the assays selected from i) analysis of 16S rRNA from the *E. coli*, ii) PCR of a nucleic acid from the *E. coli*, iii) sequencing of a gene from the *E. coli*, iv) a metagenomic assay, v) cultivation of the *E. coli*, and vi) biochemical identification of the *E. coli*.

In another aspect is provided a method for determining susceptibility to T1D in a mammal, said method comprising detecting the level of *E. coli* bacteriophages in the gastrointestinal microbiota of the mammal by performing one or more of assays selected from i) PCR of a nucleic acid from the *E. coli* bacteriophages, ii) sequencing of a gene from the *E. coli* bacteriophages, iii) a metagenomic assay, iv) cultural identification of the *E. coli* bacteriophages, and v) biochemical identification of the *E. coli* bacteriophages.

In some embodiments, the mammal is a human.

In some embodiments, the detecting of an increased level of *E. coli* and/or an increase or decrease in the level of *E. coli* bacteriophages and/or a microbial inducer of *E. coli* prophages in the gastrointestinal microbiota is conducted at 100-200 days after birth of the human.

In some embodiments, the detecting is conducted at 130-180 days after birth of the human.

In some embodiments, the method further comprises detecting a decrease in the level of *E. coli* and/or an increase or a decrease in the level of *E. coli* bacteriophages and/or microbial inducers of *E. coli* prophages subsequent to the detecting of the increased level of *E. coli*. In some embodiments, the mammal is a human and the detecting of a decrease in the level of *E. coli* is performed when the human is between 9 months of age and 30 months of age.

In another aspect is provided a method for detecting susceptibility to T1D in a mammal, said method comprising detecting the amount of T1DAMP in feces from the mammal, where an increased level of T1DAMP in the feces indicates an increased likelihood to T1DAMP binding to β-cell or dendritic cell expressing a Toll-like 2 receptor or a Toll-like 9 receptor and promotes death of the β cell to thereby increase susceptibility to T1D.

In some embodiments, the T1DAMP is an amyloid protein, a bacterial amyloid protein, an amyloid-like protein, a bacterial amyloid curli protein, an amyloid precursor, a bacterial curli, an amyloid-DNA complex, an amyloid-nucleic acid complex, or a bacterial DNA.

In some embodiments, the mammal is human.

In another aspect is provided a composition for preventing or treating Type 1 Diabetes, wherein the composition comprises one or more of a microorganism or a by-product of the microorganism, an anti-amyloid antibody, fosfomycin, Doxycycline, Ciprofloxacin, Trimethoprim/sulfamethoxazole, Levofloxacin, Amoxicillin, Aztreonam, Nitrofurantoin, Ceftriaxone, imipenem, and Rifaximin, a FimH antagonist, and a pilicide.

In some embodiments, the microorganism is from an order selected from Bacteroidales, Lactobacillales, Erysipelotrichales, Coriobacteriales, Clostridiales, Bacillales, and Bifidobacteriales.

In some embodiments, the FimH antagonist is an n-Heptyl α-D-mannose glycopolymer, methyl R-D-mannoside, or a thiazolylmannoside.

In some embodiments, the pilicide is selected from
i) 7-(1-naphthylmethyl)-5-oxo-8-phenyl-2,3,6,7-tetrahydro-5H-[1,3]thiazolo[3,2-a]pyridine-3-carboxylic acid
ii) 8-cyclopropyl-7-(1-naphthylmethyl)-5-oxo-2,3,6,7-tetrahydro-5H-[1,3]thiazolo[3,2-a]pyridine-3-carboxylic acid
iii) 7-(1-naphthylmethyl)-5-oxo-8-pentyl-2,3,6,7-tetrahydro-5H-[1,3]thiazolo[3,2-a]pyridine-3-carboxylic acid
iv) 8-(4-bromophenyl)-7-(1-naphthylmethyl)-5-oxo-2,3,6,7-tetrahydro-5H-[1,3]thiazolo[3,2-a]pyridine-3-carboxylic acid
v) 7-(1-naphthylmethyl)-5-oxo-8-phenyl-2,3-dihydro-5H-[1,3]thiazolo[3,2-a]pyridine-3-carboxylic acid, lithium salt
vi) 8-cyclopropyl-7-(1-naphthylmethyl)-5-oxo-2,3-dihydro-5H-[1,3]thiazolo[3,2-a]pyridine-3-carboxylic acid, lithium salt
vii) 7-methyl-5-oxo-8-phenyl-2,3-dihydro-5H-[1,3]thiazolo[3,2-a]pyridine-3-carboxylic acid, lithium salt
viii) 6-dimethylaminomethyl-7-(1-naphthylmethyl)-5-oxo-8-phenyl-2,3-dihydro-5H-[1,3]thiazolo[3,2-a]pyridine-3-carboxylic acid, lithium salt
ix) 6-morpholinomethyl-7-(1-naphthylmethyl)-5-oxo-8-phenyl-2,3-dihydro-5H-[1,3]thiazolo[3,2-a]pyridine-3-carboxylic acid, lithium salt
x) 8-cyclopropyl-6-morpholinomethyl-7-(1-naphthylmethyl)-5-oxo-2,3-dihydro-5H-[1,3]thiazolo[3,2-a]pyridine-3-carboxylic acid, lithium salt, and
xi) 6-dimethylaminomethyl-7-methyl-5-oxo-8-phenyl-2,3-dihydro-5H-[1,3]thiazolo[3,2-a]pyridine-3-carboxylic acid, lithium salt.

In another aspect is provided a composition comprising an antagonist of an amyloid-producing bacteria, the composition comprising a defined microbial consortia of amyloid-producing bacteria antagonists selected from the group consisting of Bacteroidetes, Firmicutes, Proteobacteria, Verrucomicrobiae, and Actinobacteria, and where the composition is formulated for oral administration, for parenteral administration by nasogastric tube, or administration by colonoscopy. In some embodiments, the amyloid-producing bacteria are Enterobacteriales bacteria or *E. coli*.

In another aspect is provided a composition comprising an antagonist of an amyloid-producing bacteria, the composition comprising a microorganism, an excipient, and a defined microbial consortia of non-amyloid producing strains selected from the group Enterobacteriales and/or *E. coli*, and where the composition is formulated for oral administration, for parenteral administration by nasogastric tube, or administration by colonoscopy. In some embodiments, the amyloid-producing bacteria are Enterobacteriales bacteria or *E. coli*.

In another aspect is provided a composition comprising a fecal or non-fecal microbiome transplantation material and an antagonist of an amyloid-producing bacteria, where the transplantation material comprises one or more microorganisms belong to any one of Actinomycetales, Bacteroidales, Flavobacteriales, Bacillales, Lactobacillales, Clostridiales, Erysipelotrichales, Selenomonadales, Fusobacteriales, Neisseriales, Campylobacterales or Pasteurellales. In some embodiments, the amyloid-producing bacteria are Enterobacteriales bacteria or *E. coli*.

In another aspect is provided a composition for the inactivating amyloid-producing bacteria within microbiota by inhibition of curli assembly and their effects on macroorganisms by Transthyretin, as anti-α-sheet inhibitors, parthenolides, benzoquinone derivatives, (2-(12-hydroxydodeca-5,10-diynyl)-3,5,6-trimethyl-p-benzoquinone, 2,3,5-trimethyl-6-(12-hydroxy-5,10-dodecadiynyl)-1,4-benzoquinone), or tafamidis, where the composition is formulated for oral administration, parenteral administration by nasogastric tube, or administration by colonoscopy, or IV.

In another aspect is provided a method of preventing a T1DAMP effect on macroorganisms, the method comprising administering an effective amount of deoxyribonuclease to a subject by oral administration, parenteral administration by nasogastric tube, or IV, or administration by colonoscopy, wherein the composition is administered once per day, more than once per day, once per week, multiple times per week, once per month, or multiple times per month for a year, for 2 years, 3 years, 4, years, 5 years, from 5 years to 20 years, or for a period exceeding 20 years.

In another aspect is provided a composition comprising one or more anti-amyloid-producing bacterial antibodies, where the composition is formulated for oral administration, for parenteral administration by nasogastric tube, or for administration by colonoscopy. In some embodiments, the composition is formulated for administration to a subject once, once per day, multiple times per day, once per week, multiple times per week, once per month, or multiple times per month for a year, for 2 years, 3 years, 4, years, 5 years, from 5 years to 20 years, or for a period exceeding 20 years, optionally wherein the composition is formulated for administration before or after the development of T1D autoimmunity.

In another aspect is provided a composition comprising one or more antibodies against bacterial amyloid protein and/or DNA-amyloid complexes and/or their components, where the composition is formulated for oral administration, for parenteral administration by nasogastric tube, or IV, or for administration by colonoscopy. In some embodiments, the composition is formulated for administration to a subject once, once per day, multiple times per day, once per week, multiple times per week, once per month, or multiple times per month for a year, for 2 years, 3 years, 4, years, 5 years, from 5 years to 20 years, optionally wherein the composition is formulated for administration before or after the development of T1D autoimmunity. In some embodiments, the composition is administered to the mammal before or after the development of T1D autoimmunity. In another aspect is provided a composition comprising siRNA effective against components of amyloid proteins, in the appropriate excipients and are administered before or after the development of T1D autoimmunity. In some embodiments, the siRNA is against CsgA and CsgB.

In another aspect is provided a composition comprising vaccine comprising conjugates of antigens to serotypes of an amyloid-producing bacterium within the microbiota of a patient, where the bacteria belongs to Bacteroidetes, Firmicutes, Proteobacteria, Verrucomicrobiae, and Actinobacteria, before or after the development of T1D autoimmunity.

In another aspect is provided a method for preventing, delaying or treating Type 1 Diabetes (T1D) or consequences thereof in a mammal in need thereof, said method comprising one or more of
  (i) inactivating amyloid-producing bacteria within microbiota in the mammal;
  (ii) preventing amyloid-producing bacteria from entering the microbiota, the gastrointestinal tract, a bodily fluid or a tissue of the mammal, from an environment outside the mammal;
  (iii) preventing amyloid-producing bacteria to release amyloid, DNA, a complex of an amyloid or DNA to microbiota, the gastrointestinal tract, bodily fluids or a tissue of the mammal;
  (iv) inactivating a T1D-associated microbial product (T1DAMP) that is released by microbiota of the mammal;
  (v) inactivating a T1DAMP present, a bodily fluid or a tissue of the mammal;
  (vi) inhibiting release of a T1DAMP from a biofilm and/or bacteria in the gastrointestinal tract, a bodily fluid or a tissue of the mammal;
  (vii) inhibiting entry of T1DAMP to microbiota, the gastrointestinal tract, a bodily fluid or a tissue of the mammal;
  (viii) inhibiting the triggering of T1D by bacteria, T1DAMP derived from the bacteria, or a complex comprising the bacteria or the T1DAMP;
  (ix) administering to the mammal *E. coli* that do not produce an amyloid protein;
  (x) administering to the mammal a pilocene or a curlicide; and
  (xi) inhibiting the activity of a bacteriophage (xii) inhibiting the prophage inductors.

In various embodiments of the above aspects, the T1DAMP is an amyloid protein, a bacterial amyloid protein, an amyloid-like protein, a bacterial amyloid curli protein, an amyloid precursor, a bacterial curli, an amyloid-DNA complex, an amyloid-nucleic acid complex, an amyloid-nuclei acid complex, or a bacterial DNA. In some embodiments, the bacterial DNA is either genomic DNA or extracellular DNA.

In another aspect is provided a method for preventing or treating Type 1 Diabetes in a subject, the method comprising administering to the subject a composition effective to inactivate bacterial amyloid-DNA complexes, extracellular nucleic acids, and/or extracellular amyloid, where the composition comprises one or more of an antibody, a nuclease, a protease, an intercalator, and an oligonucleotide.

In another aspect is provided a method for preventing or treating Type 1 Diabetes in a mammalian subject, the method comprising vaccinating the subject against amyloid-producing bacteria, amyloid-DNA complexes, amyloid, and/or extracellular nucleic acids. In some embodiments, the amyloid-producing bacteria are Enterobacteriales bacteria or *E. coli*.

In another aspect is provided a method for preventing or treating Type 1 Diabetes in a mammalian subject, the method comprising vaccinating the subject against bacteriophages of amyloid-producing bacteria.

BRIEF DESCRIPTION OF THE DRAWINGS

FIG. 2A is a bar graph of the comparison of the absolute abundance of E. coli across different samples depending on autoantibody development. In FIG. 2A, each row pair is an individual sample before and after appearance of autoantibodies. The white bars are median E. coli abundances before seroconversion. The black bars are median E. coli abundances after seroconversion. FIG. 2B shows a groupwise comparison, with white bars as median E. coli abundances before seroconversion, and black bars as median E. coli abundances after seroconversion. For the control group seroconversion time was determined as 540 days that reflected an artificial benchmark of the medium time to the appearance of autoantibodies in case groups. The significance of the comparison before versus after appearance of autoantibodies was determined by paired t test, Case (T1D and seroconverters groups) p=0.022; T1D p=0.068; Seroconvertors p=0.031; Control p=0.677. The amount of gut amyloid-producing E. coli shifts significantly after the seroconversion, in Seroconversion and T1D groups, whereas these microorganisms remain relatively stable in control groups throughout observation period.

DETAILED DESCRIPTION OF THE INVENTION

Definitions

Figure 1:
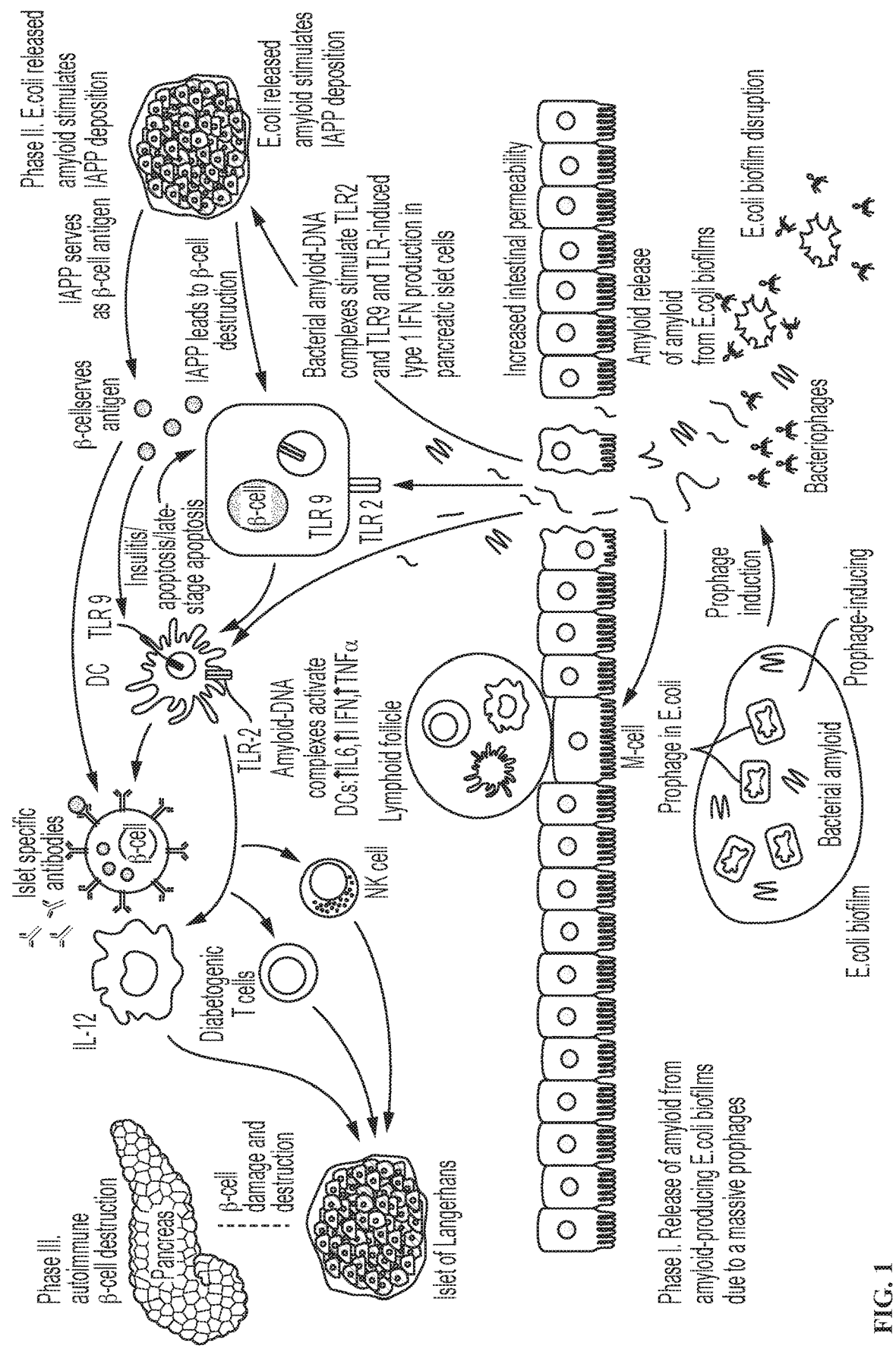
FIG. 1 shows a model of how in some mammals who have susceptibility to Type 1 Diabetes, such as by expressing certain HLA markers associated with development of Type 1 Diabetes, the induction of E. coli prophages lead to the death of E. coli populations, releasing curli from the destroyed biofilms and due to the increased intestinal permeability, by which curli complexes enter the blood stream and interplay with to pancreatic β-cells (triggering both Toll-like 2 and Toll-like 9 receptors). Such binding can lead to β-cell death. Such β-cell death is correlated with alteration of to the pancreas, such as amyloidosis of the pancreas and particularly amyloid formation in the Islet of Langerhans. Amyloidosis may be promoted by entry into the bloodstream of amyloid proteins from E. coli and other bacteria, such as *Salmonella*, present in the intestine.

Unless defined otherwise, technical and scientific terms used herein have the same meaning as commonly understood by one of ordinary skill in the art to which this invention belongs.

As used herein, the term "Type-1 Diabetes associated microbial product" or "T1DAMP" means a product from a microbe that is associated with increased risk in development of, or severity of, Type 1 Diabetes. Exemplary T1DAMPs include, but are not limited to, bacterial amyloid, an amyloid-like protein, a bacterial amyloid curli protein, an amyloid precursor, a bacterial curli, an amyloid-DNA complex, an amyloid-nucleic acid complex, or bacterial DNA.

As used herein, the term "amyloid precursor" means a protein that is a precursor of an amyloid formation.

As used herein, the term "bacterial curli" means a combination of amyloid proteins and one or more nucleic acids. The nucleic acids may be both intracellular and extracellular.

As used herein, the term "amyloid-nucleic acid complex" means a complex of amyloid protein and one or more nucleic acids. As used herein, the term "amyloid-DNA complex" means a complex of amyloid protein and DNA.

As used herein, the term "bacterial DNA" includes both intracellular bacterial DNA and extracellular bacterial DNA.

The term "microbiota" is used herein to refer to microorganisms (e.g., bacteria, archaea, fungi, protozoa) and viruses (e.g., phages and eukaryotic viruses) present in a host animal or human (e.g., in the gastrointestinal tract, skin, oral cavity, vagina, etc.). Microbiota exerts a significant influence on health and well-being of the host.

In one aspect, the invention provides a method for preventing or treating a microbiota disease or consequences thereof in a mammal in need thereof. The microbiota disease may be Type 1 diabetes (T1D). The method comprises one or more of (i) inactivation of amyloid-producing bacteria within microbiota, (ii) inactivation of amyloid-producing bacteria and/or prevention of amyloid-producing bacteria from getting to microbiota from the outer environment, gastrointestinal tract, bodily fluid(s) or tissue(s) of the mammal, (iii) inactivation of T1DAMP production/release by microbiota bacteria, (iv) inactivation of bacteria-derived T1DAMP present in microbiota, bodily fluid(s) or tissue(s) of the mammal, (v) inhibition of release of bacteria-derived T1DAMP from biofilm and/or bacteria to gastrointestinal tract, bodily fluid(s) or tissue(s) of the mammal, (vi) inhibition of entry of bacteria-derived T1DAMP to microbiota, gastrointestinal tract, bodily fluid(s) or tissue(s) of the mammal, and (vii) inhibition of the effect of bacteria-derived and/or its complexes to trigger T1D.

Inactivation of a T1DAMP can occur by one or more of modification of the T1DAMP, destruction of the T1DAMP, inhibition of the activity of the T1DAMP, and inhibition of the binding of the T1DAMP to its target.

Triggering of T1D can result in one or more of seroconversion (which is indicated by the appearance of autoantibodies), development of Type 1 diabetes, development of insulitis, and an increase in the severity of insulitis.

In another aspect, the invention provides a method for diagnosing a microbiota disease or consequences thereof in a mammal in need thereof, said method comprising detecting one or more of (i) whether the mammal expresses at least one T1D susceptible HLA allele having an HLA haplotype, (ii) increased intestinal permeability in the mammal relative to the intestinal permeability in a normal patient, or (iii) an increased level of $E.$ $coli$ in one or more portions of the gut of the mammal. In some embodiments, the HLA allele having an HLA haplotype is an HLA allele having a DR4-DQ8 haplotype, an HLA allele having a DR3-DQ2 haplotype, HLA allele DQB1*02/*0302-DRB1*0404, HLA allele DQB1*0302/*0501-DRB1*0401, or HLA allele DQB1*0302/*04-DRB1*0401*.

Without wishing to be bound by theory, the initiation phase of T1D occurs in the intestine, where in subjects predisposed to T1D, $E.$ $coli$ prophage induction leads to the disruption of the $E.$ $coli$ biofilms, and release of curli-DNA complexes. See FIG. 1. These amyloid complexes may pass through the intestinal barrier and can lead to the seroconversion and T1D by different ways. (Subjects with certain HLA alleles may have increased intestinal permeability.) Amyloid released by $E.$ $coli$ stimulates IAPP deposition in pancreas that leads to a beta-cell destruction caused by IAPP aggregation or acts as a β-cell autoantigen. Curli DNA complexes activate TLR2 and TLR9 in β-cells, triggering production of TI IFN and chemokines, thus contributing to local inflammatory reaction (insulitis) and triggering apoptotic pathway through proapoptotic protein BIM activation (not shown) and leading to the formation of β-cell autoantigens. The exposure of B cells to β-cell autoantigens derived due to islet cells apoptosis/late stage apoptosis may lead to the production of β-cell-targeting autoantibodies.

Bacterial amyloid forms curli fibers, which are highly ordered cross-beta amyloid β-sheets composed of CsgA, the major subunit of the fibril, and a minor subunit, CsgB. CsgA and CsgB are co-secreted across the plasma membrane. CsgB nucleates and attaches CsgA to the surface of bacterial cell. In turn, soluble CsgA polymerizes with the cell surface bound CsgA, forming the core of the amyloid β-sheet secondary structure. Bacterial amyloid can also form complexes with DNA ("curli DNA complexes").

Without wishing to be bound by theory, curli DNA complexes and β-cell autoantigens activate TLR2 and TLR9 in dendritic cells (DC) that produce high amounts of proinflammatory cytokines including IL-6, TNF-α and type I IFNs. DCs that are activated by amyloid and β-cell autoantigens promote presentation of the islet cells antigens to T cells. The DCs activate CD4+ T cells, diabetogenic cytotoxic CD8+ T cells, and macrophages. The DCs also activate natural killer cells (NK) which promote killing of β-cells through production of cytokines, cytolytic granules, TNF and reactive oxygen species.

This study revealed an association between the development of autoantibodies in children with HLA-conferred susceptibility and initially high gut $E.$ $coli$ abundance, followed by the disappearance of $E.$ $coli$ due to prophage induction. Further, these findings suggest that amyloid released from these amyloid-producing bacteria might be involved in the initiation of autoimmunity (see, e.g., FIG. 1).

The initial phase of T1D autoimmunity for the first time suggested to be triggered in the intestine in HLA-predisposed subjects with elevated $E.$ $coli$ abundance. $E.$ $coli$ prophage induction may lead to the disruption of the $E.$ $coli$ biofilm and release of curli-DNA complexes. These amyloid complexes can pass through the impaired intestinal barrier and/or act through the Peyer patches, and might lead to seroconversion and T1D in different ways.

Without wishing to be bound by theory, the amyloid released by $E.$ $coli$ might stimulate IAPP deposition in the pancreas, which could lead to β-cell destruction caused by IAPP aggregation, or the amyloid could act as a β-cell autoantigen.

Without wishing to be bound by theory, curli DNA complexes might activate TLR2 and TLR9 in β-cells, which could trigger the production of type I IFN and chemokines, thus contributing to local inflammatory reaction (insulitis) and triggering an apoptotic pathway through proapoptotic protein BIM activation and leading to the formation of β-cell autoantigens. The exposure of B cells to β-cell autoantigens derived from islet-cell apoptosis/late-stage apoptosis could lead to the production of β-cell-targeting autoantibodies.

Without wishing to be bound by theory, curli DNA complexes (with or without β-cell autoantigens) might activate TLR2 and TLR9 in dendritic cells (DCs), which produce large amounts of proinflammatory cytokines, including IL-6, TNF-α, and type I IFN. The DCs activated by amyloid and β-cell autoantigens could then promote the presentation of islet-cell antigens to T cells. The DCs could then activate CD4+T and diabetogenic cytotoxic CD8+ T cells, macrophages, and natural killer cells, which could promote the killing of β-cells through the production of cytokines, cytolytic granules, TNF, and reactive oxygen species.

The analysis described herein reveals a correlation between (i) an initially high level of amyloid-producing $E.$ $coli$ in the intestine, followed by their depletion, and (ii) the initiation of autoimmunity and T1D progression. The diabetogenic role of $E.$ $coli$ prophages was supported by the fact that the activation of $E.$ $coli$ prophages with mitomycin C resulted in pronounced amyloid release from preformed microbial biofilms in vitro. Together with the data from metagenomics analysis, these findings suggest the same process might occur in the gut of children who develop autoimmunity and T1D. The findings described herein for the first time suggest that curli released by $E.$ $coli$ might trigger autoimmunity in susceptible children, highlighting the need to pay specific attention to the relationships between amyloid-producing bacteria and their bacteriophages in genetically susceptible hosts. The present demonstration of the role of *E. coli*-derived amyloid in the progression of T1D allows development of novel diagnostics and interventional approaches.

In one embodiment of the above aspects relating to preventing or treating a microbiota disease, the inactivation of amyloid-producing bacteria within microbiota is performed in a patient having at least one T1D susceptible HLA allele having an HLA haplotype. In some embodiments, the HLA allele having an HLA haplotype is an HLA allele having a DR4-DQ8 haplotype, an HLA allele having a DR3-DQ2 haplotype, HLA allele DQB1*02/*0302-DRB1*0404, HLA allele DQB1*0302/*0501-DRB1*0401, or HLA allele DQB1*0302/*04-DRB1*0401*.

The amyloid-producing bacteria may be associated with curli biogenesis.

In one embodiment of the above methods for preventing or treating a microbiota disease or consequences thereof, prevention of colonization with amyloid-producing bacteria and/or inactivation of amyloid-producing bacteria within microbiota comprises colonizing the microbiota with modified strains of amyloid-producing bacteria, such as non-amyloid-producing strains or strains that synthesize reduced amounts of amyloid, for example those in which bacteria belong to Enterobacteriales.

In one embodiment of the above methods for preventing or treating a microbiota disease or consequences thereof, prevention of colonization with amyloid-producing bacteria and/or inactivation of amyloid-producing bacteria within microbiota comprises colonizing the microbiota with modified strains of amyloid-producing bacteria, such as non-amyloid-producing strains or strains that synthesize reduced amounts of amyloid, for example those in which bacteria belong to Bacillales.

In one embodiment of the above methods for preventing or treating a microbiota disease or consequences thereof, prevention of colonization with amyloid-producing bacteria and/or inactivation of amyloid-producing bacteria within microbiota comprises colonizing the microbiota with modified strains of amyloid-producing bacteria, such as non-amyloid-producing strains or strains that synthesize reduced amounts of amyloid, for example those in which bacteria belong to *E. coli*.

In one embodiment of the above methods for preventing or treating a microbiota disease or consequences thereof, prevention of colonization with amyloid-producing bacteria and/or inactivation of amyloid-producing bacteria within microbiota comprises colonizing the microbiota with modified strains of amyloid-producing bacteria, such as non-amyloid-producing strains or strains that synthesize reduced amounts of amyloid, for example those in which bacteria belong to *E. coli* of any of the four phylogenetic groups designated as "A," "B1," "B2," and "D."

In one embodiment of the above methods for preventing or treating a microbiota disease or consequences thereof, inactivation of amyloid-producing bacteria within microbiota comprises the prevention of colonization with amyloid-producing bacteria by the use of antagonistic microorganisms or their by-products, including antagonists of Enterobacteriaceae.

In one embodiment of the above methods for preventing or treating a microbiota disease or consequences thereof, inactivation of amyloid-producing bacteria within microbiota comprises the prevention of colonization with amyloid-producing bacteria by the use of antagonistic microorganisms or their by-products, including antagonists of amyloid-producing bacteria, such as members of Bifidobacteriaceae vs. Enterobacteriaceae; Lactobacillaceae vs. Enterobacteriaceae.

In one embodiment of the above methods for preventing or treating a microbiota disease or consequences thereof, inactivation of amyloid-producing bacteria within microbiota comprises decreasing colonization with amyloid-producing bacteria by the use of antagonistic microorganisms or their by-products including antagonists of amyloid-producing bacteria, such as: members of Bifidobacteriaceae vs. Enterobacteriaceae; Lactobacillaceae vs. Enterobacteriaceae.

In one embodiment of the above methods for preventing or treating a microbiota disease or consequences thereof, inactivation of amyloid-producing bacteria within microbiota comprises preventing or decreasing colonization with amyloid-producing bacteria by the use of antagonistic microorganisms (including those that were previously unculturable) or their by-products of amyloid-producing bacteria, of Bifidobacteriaceae vs. Enterobacteriaceae; Lactobacillaceae vs. Enterobacteriaceae.

In one embodiment of the above methods for preventing or treating a microbiota disease or consequences thereof, the method comprises inactivating amyloid-producing bacteria within microbiota by triggering mutations and editing bacterial genomes, which can lead to alterations in the transcription of and/or expression of amyloid associated genes and genes that affect curli production, including non-limiting examples of Bap, CsgA, CsgB, FabB, FapC, fapF, Fab E, hfq, nagA, TasA, TapAAgrd, PapD, WaaC, WaaA, WaaE, IpcA; Cell envelope biogenesis, outer membrane genes, e.g., csgE, csgF, csgG, cusB, galU, Lpp, mdoH, mltA, mltB, nlpD, ompC, ompF, rcsF, pal, rfe, rffA, rffT, slp, tolc, waaC, waaD, waaE, waaF, waaG, waaP, wzxE, ycgV; Cell motility and secretion genes, e.g., cpxP, flgM, fliI, tolA, ycbR;

Posttranslational modification, protein turnover, chaperone genes, e.g., ccmA, clpA, clpP, clpX, dnaK, lon, sspA, surA, yfgC, yjjW, yncG;

Inorganic ion transport and metabolism genes, e.g., cpxP, cysC, cysI, ddpD, dps, fepB, fepC, fepD, fepG, fes, mdfA, mdoG, nhaA, yoeE Signal transduction mechanism genes, e.g., arcA, clpX, cpxA, cpxP, cpxR, crp, cusR, dksA, envZ, fhlA, gmr, kdpD, narQ, ompR, qseC, rseA, rstA, rstB, uspE, ydaM, yedV, yeiL, zraR;

Translation, ribosome structure, and biogenesis genes, e.g., efp, miaA, pcnB, poxA, rbfA, rimK, rimM, rplA, rpsF, rpsT, rsgA, srmB, truB;

Transcription genes, e.g., aaeR, arcA, asnC, cpxR, crp, cra, csgD, cusR, cysB, cytR, dksA, fliT, fhlA, flgM, gcvA, greA, hdfR, hfq, ihfA, ihfB, mirA, mtlR, nagK, nanK, nusB, ompR, perR, purR, puuR, rcsB, rffC, rpoN, rpoS, rpoZ, rstA, sdiA, srlR, treR, waaH, xapR, ydcl, yieP, ynaK DNA replication, recombination, and repair genes, e.g., atl, dam, dnaG, dnaT, ihfA, ihfB, nudC, nudL, priA, rnhA, rppH;

Autotransporter genes, e.g., Ag43;

with different methods, including, but not limited to CRISPR.

In one embodiment of the above methods for preventing or treating a microbiota disease or consequences thereof, the method comprises inactivating amyloid-producing bacteria within microbiota by triggering mutations and editing of bacterial genomes leading to alterations of the activity of amyloid associated genes, with examples including but not limited to the regulation of csgDEFG operon, fapABCDEF operon, adrA, csgD, RpoS (σS), Crl, MlrA, H-NS, IHF, or tapA-sipW-tasA.

In one embodiment of the above methods for preventing or treating a microbiota disease or consequences thereof, the method comprises inactivating amyloid-producing bacteria within microbiota by triggering mutations and editing of bacterial genomes leading to alterations of the activity of amyloid associated genes, for example with siRNA administered orally (different formulations including protection from the negative effect of the gastrointestinal tract, e.g., nanoparticles having intraintestinal release), intravenously, intraperitoneally, intranasally etc.

In one embodiment of the above methods for preventing or treating a microbiota disease or consequences thereof, the method comprises inactivating bacterial-derived amyloids within microbiota by alteration of fibrillation nucleators (with nonlimiting examples including CsgB, FapB, TapA, and AgrD).

In one embodiment of the above methods for preventing or treating a microbiota disease or consequences thereof, the method comprises inactivating amyloid-producing bacteria within microbiota by inhibition of curli assembly within a biofilm.

In one embodiment of the above methods microbial-derived T1DAMP is derived from bacteria or fungi.

In one embodiment of the above methods for preventing or treating a microbiota disease or consequences thereof, the method comprises inactivating amyloid-producing bacteria within microbiota by induction of curli disassembly.

In one embodiment of the above methods for preventing or treating a microbiota disease or consequences thereof, the method comprises inactivating amyloid-producing bacteria within microbiota by the induction of proteasome-mediated degradation and autophagy.

In one embodiment of the above methods for preventing or treating a microbiota disease or consequences thereof, the method comprises inactivating amyloid-producing bacteria within microbiota by inhibition of curli assembly by Transthyretin, as anti-α-sheet inhibitors, parthenolides, benzoquinone derivatives, AA-861 (2-(12-hydroxydodeca-5,10-diynyl)-3,5,6-trimethyl-p-benzoquinone, 2,3,5-trimethyl6-(12-hydroxy-5,10-dodecadiynyl)-1,4-benzoquinone) (CAS registry number 80809-81-0), or tafamidis. AA-861 may be obtained from Sigma under product number A 3711.

In one embodiment of the above methods for preventing or treating a microbiota disease or consequences thereof, the method comprises replacing the microbiota with fecal microbiota transplantation (FMT) or non-fecal microbiota transplantation (non-FMT).

In one embodiment of the above methods for preventing or treating a microbiota disease or consequences thereof, the method comprises preventing seroconversion and T1D development in hosts with HLA alleles associated with T1D by the fecal microbiota transplantation (FMT) or non-fecal microbiota transplantation (non-FMT) with controlled and reduced numbers of amyloid-producing bacteria.

In one embodiment of the above methods for preventing or treating a microbiota disease or consequences thereof, the method comprises preventing T1DAMP (e.g., curli) formation by administering one or more nucleases, to the mammal. The nuclease may be a deoxyribonuclease.

In one embodiment of the above methods for preventing or treating Type 1 Diabetes by prevention of the effects of inactivation of amyloid-producing bacteria and/or T1DAMP on protein with prion-like properties misfolding and/or deposition.

In one embodiment of the above methods for preventing or treating Type 1 Diabetes by prevention of the effects of inactivation of amyloid-producing bacteria and/or T1DAMP on protein misfolding and/or deposition of Islet amyloid polypeptide.

In one embodiment of the above methods for preventing or treating a microbiota disease or consequences thereof, the method comprises amyloid and amyloid-DNA complex release to intestinal lamina propria, biological fluids and tissues is prevented. The release can lead to an increase of intestinal permeability, affecting for example, tight junction proteins, adherens junctions, Zonula occludens proteins, claudin, and occludin.

In one embodiment of the above methods for preventing or treating a microbiota disease or consequences thereof, the method comprises amyloid and amyloid-DNA complexes release to intestinal lamina propria, biological fluids and tissues is prevented by the regulation of an altered gut barrier with the use of agents, such as probiotics and nutritional formulas.

In one embodiment of the above methods for preventing or treating a microbiota disease or consequences thereof, the method comprises prevention of T1DAMP (e.g., amyloid and amyloid-DNA complexes) release to intestinal lamina propria, biological fluids and tissues is done by modification of barrier permeability such as mucosal permeability, intestinal permeability, to microbial-derived amyloid and its complexes by the modification of genes responsible for the intestinal permeability such as claudin-1, ZO-1, and occludin, LAMB1, HNF4α, GNA12, ECM-1, CARD15, FABP, Cldn1, Cldn8, Cldn14, Cldn15, Ocln, Gjb3, Il1b, Il18, Traf6, Casp3, Srd5a2, Gsta2, RT1Db1, RT1DMb, RT1Ba, RT1 Da, RT1 Da.

In one embodiment of the above methods for preventing or treating a microbiota disease or consequences thereof, the method comprises prevention of T1DAMP circulation by vaccinating a mammal against bacterial-amyloid and/or amyloid complexes, wherein the complexes are derived from Enterobacteriales.

In one embodiment of the above methods for preventing or treating a microbiota disease or consequences thereof, the method comprises prevention of amyloid circulation by vaccinating a mammal against bacterial-amyloid and/or amyloid complexes, wherein the complexes are derived from E. coli.

In one embodiment of the above methods for preventing or treating a microbiota disease as the combination of analysis and/or replacement therapy of amyloid-producing bacteria belonging or not-belonging to Enterobacteriales and/or E. coli with the treatments affecting immune components of the patients e.g. anti-CTLA4 Ig or a TGF-b neutralizing antibody or other methods, reducing the suppression by the CD4+ CD25+ Foxp3+ T cells and other components of the autoimmune response.

Also provided are methods for diagnosis, preventing and treatment of disease triggering and progression. In various embodiments, the disease is type 2 diabetes, metabolic syndrome, autism, amyotrophic lateral sclerosis, multiple sclerosis, Alzheimer's disease, Parkinson's disease, systemic lupus erythematodes, rheumatoid arthritis, Huntington disease, ataxias, bipolar disorder, schizophrenia, depressive disorder, chronic fatigue syndrome, atherosclerosis, obesity, Gout, Hashimoto's thyroiditis, dementias, amyloidosis, taupathias, demyelinating polyneuropathies, Grave's disease, thyroiditis, myasthenias, cardiomyopathy, atherosclerosis, polyneuropathy, and amyloidosis.

In another aspect is provided a method of diagnosis of seroconversion and T1D susceptible hosts with quantitative and/or qualitative analysis of amyloid-producing bacteria.

Non-limiting examples of the methods which can be used for the quantitative and/or qualitative analysis of amyloid-producing bacteria and/or component(s) thereof in any of the above methods for determining likelihood include, e.g., cultural microbiology methods (including those used for isolation and cultivation phages), Western blotting, ELISA, liquid biopsy methods, liquid chromatography and mass spectrometry (LC/MS) analysis, genetic methods (e.g., DNA or RNA sequencing, including high-throughput methods such as, e.g., Sanger sequencing, single-molecule real-time sequencing, ion semiconductor sequencing, sequencing by synthesis, sequencing by ligation, nanopore sequencing, pyrosequencing, large-scale sequencing, whole genome sequencing, DNA nanoball sequencing, Heliscope single molecule sequencing, single molecule real time (SMRT) sequencing, Tunnelling currents DNA sequencing, sequencing by hybridization, sequencing with mass spectrometry, microfluidic Sanger sequencing, microscopy-based techniques, RNAP sequencing, in vitro virus high-throughput sequencing), proteomic methods (e.g., determining amino acid composition, identification by mass spectrometry, predicting from DNA/RNA sequences, transcriptome analysis), metagenomic methods (e.g., Shotgun metagenomics, high-throughput sequencing, bioinformatics), computational modeling and simulation methods (e.g., metabolic modeling due to the availability of genome-scale metabolic models, software tools for automatically generating models from metagenomic data, flux balance analysis, dynamic modeling of the intestinal microbiota, Lotka-Volterra equations, multi-species modeling approaches, Computational Modeling of Intestinal Host-Microbiota Interactome), data analysis (e.g., principal coordinate analysis, community metabolism, meta-transcriptomics, analysis of microbiomes), simple simulation, and any combination thereof as well as mathematical models used to describe biological systems (e.g., Next-generation Sequencing Simulator for Metagenomics (NeSSM), combining complete genomes currently available, a community composition table, and sequencing parameters, [Jia, B., Xuan, L., Cai, K., Hu, Z., Ma, L., & Wei, C. (2013) PLoS One, 8(10), e75448]; SParse InversE Covariance Estimation for Ecological Association Inference [SPIEC-EASI]; R package dealing with microbiome association [OmiSA]; Parallel-META 3; MethaPlAn. In some embodiments, the computational modeling and simulation methods are those used for determining predisposition of the alterations of microbiota following a specific challenge.

In one embodiment of the above methods for preventing or treating a microbiota disease or consequences thereof, the prevention of colonization with amyloid-producing bacteria and/or inactivation of amyloid-producing bacteria within microbiota lead to a delayed seroconversion.

In one embodiment of the above methods for preventing or treating a microbiota disease or consequences thereof, the prevention of colonization with amyloid-producing bacteria and/or inactivation of amyloid-producing bacteria within microbiota lead to the prevention of seroconversion.

In one embodiment of the above methods for preventing or treating a microbiota disease or consequences thereof, the prevention of colonization with amyloid-producing bacteria and/or inactivation of amyloid-producing bacteria within microbiota lead to a prevention of T1D-associated islet alterations.

In one embodiment of the above methods for preventing or treating a microbiota disease or consequences thereof, the prevention of colonization with amyloid-producing bacteria and/or inactivation of amyloid-producing bacteria within microbiota lead to a prevention of T-cell mediated autoimmune response.

In one embodiment of the above methods for preventing or treating a microbiota disease or consequences thereof, the prevention of colonization with amyloid-producing bacteria and/or inactivation of amyloid-producing bacteria within microbiota lead to a prevention of Islet amyloid polypeptide deposition.

In one embodiment of the above methods for preventing or treating a microbiota disease or consequences thereof, bacterial-derived amyloid within microbiota is inactivated by altering activity (e.g., triggering mutations, editing of bacterial genomes leading to alterations of the activity, altering the number, increased expression) of proteins with anti-amyloid chaperoning activity, with CsgC as a non-limiting example.

In one embodiment of the above methods for preventing or treating a microbiota disease or consequences thereof, a bacterial-derived amyloid within microbiota is inactivated by prevention of T1DAMP polymerization.

In one embodiment of the above methods for preventing or treating a microbiota disease or consequences thereof, bacterial-derived amyloid within microbiota is inactivated by prevention CsgA polymerization.

In various embodiments of the above methods for preventing or treating a microbiota disease or consequences thereof, the bacterial-derived amyloid is an amyloid-like protein.

In various embodiments of the above methods for preventing or treating a microbiota disease or consequences thereof, the amyloid-complexes comprise a nucleic acid.

In various embodiments of the above methods for preventing or treating a microbiota disease or consequences thereof, alteration of amyloid-producing bacteria affects insulitis severity.

In another aspect, the invention provides a method for diagnosing risk of T1D in a mammal, said method comprising assessing the risk of T1D in the mammal.

In one embodiment of the above methods of diagnosis, assessing the risk of T1D is done by the evaluation of the abundance of amyloid-producing bacteria is done along with the analysis of high-risk HLA genes or other factors associated with an increased genetic risk.

In one embodiment of the above methods of diagnosis, assessing the risk of T1D is done by the evaluation of the abundance of amyloid-producing bacteria.

In one embodiment of the above methods of diagnosis, assessing the risk of T1D is done by the evaluation of the abundance of amyloid-producing bacteria together with increased genetic risk.

In one embodiment of the above methods of diagnosis, assessing the risk of T1D is done by the evaluation of the abundance of amyloid-producing bacteria together with evaluation of an altered immune and/or autoimmune response.

In one embodiment of the above methods for diagnosis of T1D is the identification of the antibodies against bacterial amyloid and/or curly and/or other microbial components, with the non-limiting example of anti-dsDNA and anti-chromatin autoantibody. In one embodiment of the above methods of diagnosis, assessing the risk of T1D is done by the evaluation of the abundance of amyloid-producing bacteria together with evaluation of an altered immune and/or autoimmune response and the presence of autoantibodies associated with T1D and destruction of pancreatic β-cells.

In one embodiment of the above methods of diagnosis, assessing the risk of seroconversion or T1D is done by the evaluation of the abundance of amyloid-producing bacteria including but not limited to Enterobacteriales and/or *E. coli* and is done with or without the analysis of the presence of high-risk HLA genes or other genetic or nongenetic factors associated with the triggering or development of seroconversion and T1D.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria_ and is done as a screening across general population or some part of it to assess risk for T1D in the general population before clinical onset of T1D. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population anytime starting from birth up to 20 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from birth up to 3 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from birth up to 6 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from birth up to 1 year. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from birth up to 2 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from birth up to 3 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from birth up to 5 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 1st month up to 3 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 1st month up to 6 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 1st month up to 1 year. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 1st month up to 2 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 1st month up to 3 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 1st month up to 5 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 3rd month up to 12 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 3rd month up to 24 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from third month up to 3 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 3rd month up to 5 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 6th month up to 12 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 6th month up to 24 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 6th month up to 3 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 6th month up to 5 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from the ninth month up to 12 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from the ninth month up to 24 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from the ninth month up to 3 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from ninth month up to 5 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 12th month up to 24 months. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or *E. coli* and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 12th month up to 3 years. The evaluation can be performed on a human subject from day 1 of birth up to 15 years of age. The analysis can be performed weekly, monthly, every two months, every three months, every four months, every six months, every nine months, or annually, for example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or E. coli and/or bacteriophages (e.g. prophages) associated with them and/or bacteria that are inducers of these prophages and/or bacteria that are antagonists of amyloid-producing bacteria and/or microbial synergists of amyloid-producing bacteria and is done as a screening across general population or some part of it to assess risk for T1D in the general population starting from 12th month up to 5 years. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain HLA alleles.

In one embodiment of the above methods of diagnosis, assessing the risk of seroconversion or T1D is done by the evaluation of the abundance of amyloid-producing bacteria belonging or not-belonging to Enterobacteriales and/or E. coli and is done in population having genetic susceptibility and/or certain HLA alleles to assess risk for T1D at any time and any frequency, starting from day 1 of birth up to 15 years.

In one embodiment of the above methods of diagnosis, assessing the risk of seroconversion or T1D is done by the evaluation of the presence of amyloid-producing bacteria belonging or not-belonging to Enterobacteriales and/or E. coli in biological fluids (blood, serum, cerebrospinal fluid, urine, saliva) and is done with other microbiological, genetic, immunological analysis (e.g. non-limiting examples of ILs, IFNs, antibodies levels), analysis of intestinal permeability to assess risk for T1D at any time and any frequency starting from day 1 of birth up to 15 years.

In one embodiment of the above methods of diagnosis, assessing the risk of seroconversion or T1D is done by the evaluation of the presence of genes associated with formation of microbial amyloid belonging or not-belonging to Enterobacteriales and/or E. coli in biological fluids (blood, serum, cerebrospinal fluid, urine, saliva) and is done with other microbiological, genetic or immunological analysis to assess risk for T1D at any time and any frequency starting from day 1 of birth up to 15 years.

In one embodiment of the above methods of diagnosis, assessing the risk of seroconversion or T1D by the evaluation of the amount of total bacterial amyloid in feces and/or in biological fluids (blood, serum, cerebrospinal fluid, urine, saliva) is done alone or in combination with other microbiological, genetic or immunological analysis to assess risk for T1D at any time and any frequency starting from day 1 of birth up to 15 years.

In one embodiment of the above methods of diagnosis, assessing the risk of seroconversion or T1D by the evaluation of the bacterial amyloid belonging to Enterobacteriales and/or E. coli bacteria amyloid in feces and/or in biological fluids (blood, serum, cerebrospinal fluid, urine, saliva) is done alone or in combination with other microbiological, genetic or immunological analysis to assess risk for T1D at any time and any frequency starting from day 1 of birth up to 15 years.

In one embodiment of the above methods of diagnosis, assessing the risk of seroconversion or T1D is done by the evaluation of the abundance of amyloid-producing bacteria belonging or not-belonging to Enterobacteriales and/or E. coli is done by evaluating the presence of anti-amyloid antibodies in human bodily fluids.

In one embodiment of the above methods of diagnosis, assessing the risk of seroconversion or T1D is done by the evaluation of the presence of amyloid-producing bacteria belonging or not-belonging to Enterobacteriales and/or E. coli in biological fluids (e.g., blood, serum, cerebrospinal fluid, urine, saliva) and tissues and is done with other microbiological, genetic, immune cells particularities (e.g., non-limiting examples of dendritic cells (DC), natural killer (NK) cells, NKT cells, lymphocytes, macrophages and their components) at any time and any frequency starting from day 1 of birth up to 15 years.

In some embodiments of the above methods of diagnosis, assessing the risk of seroconversion or T1D is performed by the evaluation of the abundance of amyloid-producing bacteria belonging or not-belonging to Enterobacteriales and/or E. coli and/or bacteriophages (e.g. prophages) associated with them, and/or bacteria that are inducers of these prophages and/or bacteria that are antagonists of amyloid-producing bacteria and/or microbial synergists of amyloid-producing bacteria. The method comprises screening across general population, or some part of the population, to assess risk for T1D in the general population before clinical onset of T1D. The evaluation can be performed on a human subject from day 1 of birth up to 15 years of age. The analysis can be performed weekly, monthly, every two months, every three months, every four months, every six months, every nine months, or annually, from example. The part of the general population may be a specific population, such as a population known or thought to be predisposed to T1D or a population whose members have certain T1D susceptible genes with the non-limiting examples of ERBB3, IFIH1, PTPN22, CLEC16A, CTLA4, SH2B3, IL18RAP, COBL, PTPN22. CTLA4, AIRE, FoxP3, STAT3, IFIH1, HIP14, ERBB3, Ins-VNTR, and IDDM 2.

In some embodiments of the above methods of diagnosis, assessing the risk of seroconversion or T1D, the diagnosis of amyloid-producing bacteria is done within microbiomes that include, but are not limited to the oral microbiome, skin microbiome, intestinal (small and large) microbiome, and the fecal microbiome.

In one embodiment of the above aspects relating to diagnosis, assessing the risk of seroconversion to autoimmunity and T1D is done by the evaluation of the abundance of amyloid-producing bacteria and/or T1DAMP, in a patient together with evaluation at least one T1D susceptible HLA allele having an HLA haplotype (with a non-limiting example of e.g. HLA-DRB1-HLA-DQA1-HLA-DQB1; DR3; DQB1*0201; DR4-DQ8; DR3-DQ2; DR4, DQB1*0302; DR3, DQB1*0201 DR4 DRB1*0301-DQA1*0501-DQB1*0201; DRB1*0405-DQA1*0301-DQB1*0302, DRB1*0401-DQA1*0301-DQB*0302, DRB1*0402-DQA1*0301-DQB1*0302; DRB1*0404-DQA1*0301-DQB1*0302; DRB1*0801-DQB1*0401-DQB1*0402 (OR 1.25); DRB1*1501-DQA1*0102-DQB1*0602; DRB1*1401-DQA1*0101-DQB1*0503; DRB1*0701-DQA1*0201-DQB1*0303; DRB1*03:01-DQB1*02:01-DQA1*05:01; DRB1*03:01-DQB1*02:01-DQA1*05:01/DRB1*04-DQB1*03:02-DQA1*03; HLA-DR3/HLA-DR4; HLA-DRB1*03:01-HLA-DQA1*05:01-HLA-DQB1*02:01 and HLADRB1*04:04-HLA-DQA1*03:01-HLA-DQB1*03:02; HLA-DRB1*04:01-

HLA-DQA1*03:01-HLA-DQB1*03:02 and HLA-DRB1*07:01-HLA-DQA1*02:01-HLA-DQB1*02:02) and/or other genes associated with T1D susceptibility (with a non-limiting example of e.g. ERBB3, IFIH1, PTPN22, CLEC16A, CTLA4, SH2B3, IL18RAP, COBL, HLA-DRB1, HLA-DQA2, INS, IL2RA, IFIH1, PPARG, KCNJ11, TCF7L2, PHTF1-PTPN22, ERBB3, C12orf30, SUOX-IKZF4, UBASH3A, PTPN2, EDG7, BACH2, GLIS3, RASGRP1, STAT4, STAT3, ERAP1, TNFAIP3, KIF5A/PIP4K2C, MHC, C10orf59, SH2B3, IL2RA, IL27, C6orf173, IL2, ORMDL3, CD69, IL10, IFIH1, BACH2, CTSH, PRKCQ, C1QTNF6, PGM1, KIAA0746, C6orf173, L2R, INS, Cl4orf181, PRKD2, HERC2, IFNG, IL26, DLK1, TYK2, IFIH1, SH2B3, ERBB3, CTSH, CENPW, SKAP2, PRKCQ, RNLS, SIRPG, CTRB2, LMO7, EFR3B, 6q27, TNFRSF11B, LOC100128081, FOSL2, HTR1A, RFN180, CUX2, AIRE, FoxP3, STAT3, IFIH1, HIP14, ERBB3, Ins-VNTR, IDDM 2.

Also provided is a method of treatment and prevention of seroconversion or T1D. The method comprises preventing the interaction of amyloid-producing bacteria belonging or not-belonging to Enterobacteriales and/or E. coli and their components in biological fluids and tissues with immune cells. Examples of immune cells include, but are not limited to, dendritic cells (DC), natural killer (NK) cells, NKT cells, lymphocytes, macrophages and their components.

In some embodiments, treatment and prevention of seroconversion or T1D comprises preventing the interaction of amyloid-producing bacteria belonging or not-belonging to Enterobacteriales and/or E. coli and their components and/or associated bacteriophages together with (i) drugs intended to affect immune cells that destroy the pancreatic beta-cells (e.g., eplizumab, teplizumab, otelixizumab); or (ii) that affect interferon alpha or its production; or (iii) immunotherapies that can arrest the decline in C-peptide; or (iv) immunotherapies that can decrease cytokines; or (v) stem cells therapies, or (vi) inhibiting T-cell activation and helper T-cell IL-2 production. Examples of immune cells include, but are not limited to, dendritic cells (DC), natural killer (NK) cells, NKT cells, lymphocytes, macrophages and their components).

In one embodiment of the above aspects relating to diagnosis or prevention, or treatment of seroconversion and T1D development, the method may be performed in a patient having specific alterations of amyloid-producing bacteria that belong or do not belong to Enterobacteriales and/or E. coli and/or bacteriophages (e.g. prophages) associated with them, together with evaluation at least one T1D susceptible HLA allele having an HLA haplotype with a specific SNPs with a non-limiting examples of SNP rs689, rs231775 in CTLA-4-AA, rs3757247 in BATCH2 T allele and a combination thereof.

In one embodiment of the above aspects relating to diagnosis or prevention, or treatment of seroconversion and T1D development, the method may be performed in a patient having specific alterations of amyloid-producing bacteria belonging or not-belonging to Enterobacteriales and/or E. coli and/or bacteriophages (e.g. prophages) associated with them together with evaluation of body weight index, first degree relatives having T1D, a high rate of weight gain per year, glucagon-like peptide 1 receptor ILs levels, dendric cells analysis, glucose tests, A1C analysis, C peptides levels and other phenotypic and physiological data.

In one embodiment of the above aspects relating to diagnosis, assessing the risk of seroconversion of the autoimmunity and T1D onset, the method comprises the evaluation of the abundance of amyloid-producing bacteria or their components within feces, saliva, urine, small intestine, large intestine, oral cavity, skin. In one embodiment of the above methods of diagnosis, assessing the risk of T1D comprises the evaluation of the absolute abundance of amyloid-producing bacteria belonging or not-belonging to Enterobacteriales and/or E. coli and/or bacteriophages. In one embodiment of the above methods of diagnosis, assessing the risk of T1D comprises the evaluation of the relative abundance of amyloid-producing bacteria belonging or not-belonging to Enterobacteriales and/or E. coli and/or bacteriophages. In one embodiment of the above methods of diagnosis, assessing the risk of T1D comprises the evaluation of the abundance of amyloid-producing bacteria that belong or do not belong to Enterobacteriales and/or E. coli and/or bacteriophages together with the analysis of other bacteria, fungi, viruses, archaea and protozoa in the gut. In one embodiment of the above methods of diagnosis, assessing the risk of T1D comprises the evaluation of the abundance of amyloid-producing bacteria belonging or not-belonging to Enterobacteriales and/or E. coli and/or bacteriophages together with (i) the analysis of other bacteria, and/or fungi, and/or viruses, and/or archaea and/or protozoa in the gut (ii) genomic methods and (iii) phenotypic analysis.

In one embodiment of the above aspects relating to diagnosis prevention and treatment, assessing the risk of seroconversion of the autoimmunity and T1D onset comprises the evaluation of the abundance of amyloid-producing bacteria or their components together with proteome, transciptome analysis and or other microbiome alterations (e.g. alterations of Actinomycetales, Bifidobacteriales). In one embodiment of the above aspects relating to diagnosis prevention and treatment, assessing the risk of seroconversion of the autoimmunity and T1D onset comprises the evaluation of the abundance of amyloid-producing bacteria by the presence of specific to these bacteria nucleic acid fragments, cell wall components, by genomic or microbiological analysis. In one embodiment of the above aspects relating to diagnosis, prevention and treatment, assessing the risk of seroconversion of the autoimmunity and T1D onset comprises the evaluation of the abundance of amyloid-producing bacteria by the presence of their bacteriophages by the evaluation of their nucleic acids by genomic methods or by evaluation of their titers microbiological analysis. In one embodiment of the above aspects relating to diagnosis, prevention and treatment, assessing the risk of seroconversion of the autoimmunity and T1D onset comprises the evaluation of the abundance of amyloid-producing bacteria and their components.

In various embodiments of the above aspects, T1D onset is delayed.

Prevention or inhibition of T1DAMP (e.g. amyloid) formation may be performed by inhibiting β-sheet transition of soluble amyloid. Prevention or inhibition of T1DAMP formation may be performed by using, modifying, and/or administering E. coli isolated from the patient. For example, E. coli can be sequenced. The cagA and cagB genes can be identified. An siRNA can be developed to target and inactivate cagA or cagB in the isolated E. coli. The isolated E. coli, for example with inactivated cagA or cagB, can be administered to the patient, e.g., in a manner effective to recolonize the gut with the isolated E. coli.

Prevention of T1D may comprise contacting E. coli with a CRISPR enzyme to prevent both lysogenic infection and induction of prophages.

Prevention of T1D may comprise introducing mutations to bacteria, e.g., *E. coli*, that inactivate the prophage induction.

Prevention of T1D may comprise introducing mutations that inactivate the *E. coli* prophage induction.

In various embodiments of the above methods relating to treatment or prevention of T1D, the method comprises a combination of any above described methods associated with modification of T1DAMP and/or amyloid-comprising complexes, to block TLRs (e.g. TLR2 and TLR9), with various known therapies for the prevention and treatment of T1D, including administration of insulin, antivirals, antibiotics. The methods may comprise producing bacteria belonging or not-belonging to Enterobacteriales and/or *E. coli*, and combining the produced bacteria with administration of the agents effective to decrease intestinal permeability.

In one embodiment of the above methods relating to treatment or prevention of T1D, the method comprises taking amyloid-producing bacteria belonging to Bacteroidetes, Firmicutes, Proteobacteria, Verrucomicrobiae, and Actinobacteria, taken from the microbiota of the patient, and modifying the bacteria ex vivo so as to prevent formation or release of bacterial amyloid and/or DNA-amyloid complexes.

In one embodiment of the above aspects relating to diagnosis, assessing the risk of seroconversion to autoimmunity and T1D is done by the evaluation of the abundance of amyloid-producing bacteria, in a patient together with evaluation at least one T1D susceptible HLA allele having an HLA haplotype (with a non-limiting example of e.g. HLA-DRB1-HLA-DQA1-HLA-DQB1; DR3; DQB1*0201; DR4-DQ8; DR3-DQ2; DR4, DQB1*0302; DR3; DQB1*0201; DR4 DRB1*0301-DQA1*0501-DQB1*0201; DRB1*0405-DQA1*0301-DQB1*0302, DRB1*0401-DQA1*0301-DQB*0302, DRB1*0402-DQA1*0301-DQB1*0302; DRB1*0404-DQA1*0301-DQB1*0302; DRB1*0801-DQB1*0401-DQB1*0402 (OR 1.25); DRB1*1501-DQA1*0102-DQB1*0602; DRB1*1401-DQA1*0101-DQB1*0503; DRB1*0701-DQA1*0201-DQB1*0303; DRB1*03:01-DQB1*02:01-DQA1*05:01; DRB1*03:01-DQB1*02:01-DQA1*05:01/DRB1*04-DQB1*03:02-DQA1*03; HLA-DR3/HLA-DR4; HLA-DRB1*03:01-HLA-DQA1*05:01-HLA-DQB1*02:01 and HLADRB1*04:04-HLA-DQA1*03:01-HLA-DQB1*03:02; HLA-DRB1*04:01-HLA-DQA1*03:01-HLA-DQB1*03:02 and HLA-DRB1*07:01-HLA-DQA1*02:01-HLA-DQB1*02:02) and/or other genes associated with T1D susceptibility (with a non-limiting example of ERBB3, IFIH1, PTPN22, CLEC16A, CTLA4, SH2B3, IL18RAP, COBL, HLA-DRB1, HLA-DQA2, INS, IL2RA, IFIH1, PPARG, KCNJ11, TCF7L2, PHTF1-PTPN22, ERBB3, C12orf30, SUOX-IKZF4, UBASH3A, PTPN2, EDG7, BACH2, GLIS3, RASGRP1, STAT4, STAT3, ERAP1, TNFAIP3, KIF5A/PIP4K2C, MHC, C10orf59, SH2B3, IL2RA, IL27, C6orf173, IL2, ORMDL3, CD69, IL10, IFIH1, BACH2, CTSH, PRKCQ, C1QTNF6, PGM1, KIAA0746, C6orf173, L2R, INS, Cl4orf181, PRKD2, HERC2, IFNG, IL26, DLK1, TYK2, IFIH1, SH2B3, ERBB3, CTSH, CENPW, SKAP2, PRKCQ, RNLS, SIRPG, CTRB2, LMO7, EFR3B, 6q27, TNFRSF11B, LOC100128081, FOSL2, HTR1A, RFN180, CUX2, AIRE, FoxP3, STAT3, IFIH1, HIP14, ERBB3, Ins-VNTR, and IDDM 2).

In one embodiment of the above aspects relating to diagnosis, assessing the risk of seroconversion of the autoimmunity and T1D onset is done by the evaluation of the abundance of amyloid-producing bacteria, within feces, saliva, urine, small intestine, large intestine.

In one embodiment of the above aspects relating to diagnosis, prevention and treatment, assessing the risk of seroconversion of the autoimmunity and T1D onset is done by the evaluation of the abundance of amyloid-producing bacteria together with proteome, transcriptome analysis and/or other microbiome alterations (e.g. alterations of Actinomycetales, Bifidobacteriales).

In one embodiment of the above aspects relating to diagnosis, prevention and treatment, assessing the risk of seroconversion of the autoimmunity and T1D onset is done by the evaluation of the abundance of amyloid-producing bacteria by the presence of specific to these bacteria DNA fragments, cell walls, by genetic or microbiological analysis.

In one embodiment of the above aspects relating to diagnosis, prevention and treatment, assessing the risk of seroconversion of the autoimmunity and T1D onset is done by the evaluation of the abundance of amyloid-producing bacteria by the presence of their bacteriophages by the evaluation of their nucleic acids by genetic or evaluation of their titers microbiological analysis.

In one embodiment of the above aspects relating to diagnosis, prevention and treatment, assessing the risk of seroconversion of the autoimmunity and T1D onset is done by the evaluation of the abundance of amyloid-producing bacteria In one embodiment of the above aspects relating to diagnosis of autism, amyotrophic lateral sclerosis, multiple sclerosis, systemic lupus erythematosus, Huntington disease, type 2 diabetes wherein the detecting an increased level of amyloid-producing bacteria including with a non-limiting example to Enterobacteriales and/or *E. coli* bacteria amyloid and/or their bacteriophages and/or microbial inducers of *E. coli* prophages in the gastrointestinal microbiota is conducted alone and in combination with other genetic, environmental, epigenetic factors. These include, but are not limited to Gout, Hashimoto's thyroiditis, dementias, amyloidosis, taupathias, demyelinating polyneuropathies, Grave's disease, thyroiditis, myasthenias, cardiomyopathy, atherosclerosis, polyneuropathy, amyloidosis.

In one embodiment of the above aspects relating to diagnosis and treatment of autism, amyotrophic lateral sclerosis, multiple sclerosis, systemic lupus erythematosus, Huntington disease, type 2 diabetes wherein the detecting an increased level of amyloid-producing bacteria and their components (e.g., to Enterobacteriales and/or *E. coli* bacteria amyloid and/or their bacteriophages and/or microbial inducers of their prophages in the gastrointestinal microbiota) is conducted alone and in combination with other genetic, environmental, epigenetic factors and viral infection (e.g., rubella, enteroviruses). These include, but are not limited to, Gout, Hashimoto's thyroiditis, dementias, amyloidosis, taupathias, demyelinating polyneuropathies, Grave's disease, thyroiditis, myasthenias, cardiomyopathy, atherosclerosis, polyneuropathy, amyloidosis.

In one embodiment of the above aspects relating to diagnosis of systemic lupus erythematosus wherein the detecting an increased level of amyloid-producing *E. coli* and/or their bacteriophages and/or microbial inducers of *E. coli* prophages in the gastrointestinal microbiota is conducted.

In one embodiment of the above aspects relating to prevention and treatment of autism, amyotrophic lateral sclerosis, multiple sclerosis, Huntington disease, type 2 diabetes wherein the decrease of amyloid-producing bacteria including with a non-limiting example to Enterobacteriales and/or *E. coli* bacteria and/or their bacteriophages and/or decrease of microbial inducers of *E. coli* prophages in the gastrointestinal microbiota is conducted.

In one embodiment of the above aspects relating to prevention and treatment of systemic lupus erythematosus, wherein the decrease of amyloid-producing *E. coli* in the gastrointestinal microbiota is conducted.

In one embodiment of the above methods for preventing seroconversion to autoimmunity and T1D development using anti-TLR antibodies against, with a non-limiting examples of TLR 2, 4, 7, 9 are used in individuals with an increased amount of amyloid-producing bacteria belonging or not-belonging to Enterobacteriales and/or *E. coli*.

In one embodiment of the above methods for preventing seroconversion to autoimmunity and T1D development using anti-TLR antibodies against, with a non-limiting examples of TLR 2, 4, 7, 9 are used in individuals with an increased amount of bacteriophage nucleic acids of amyloid-producing bacteria belonging or not-belonging to Enterobacteriales and/or *E. coli*.

In one embodiment of the above methods for preventing seroconversion to autoimmunity and T1D development using anti-TLR antibodies against, with a non-limiting examples of TLR 2, 4, 7, 9 are used in individuals according to a longitudinal analysis had an increased amyloid-producing bacteria belonging or not-belonging to Enterobacteriales and/or *E. coli*, followed by their decrease over 2 fold within the next 12 months.

In one embodiment of the above methods for preventing seroconversion to autoimmunity and T1D development using anti-TLR antibodies against, with a non-limiting examples of TLR 2, 4, 7, 9 are used in individuals with an increased amount of amyloid-producing bacteria belonging or not-belonging to Enterobacteriales and/or *E. coli*.

In one embodiment of the above methods for preventing seroconversion to autoimmunity and T1D development using anti-TLR antibodies against, with a non-limiting examples of TLR 2, 4, 7, 9 are used in individuals with an increased amount of amyloid-producing bacteria belonging or not-belonging to Enterobacteriales and/or *E. coli*.

In one embodiment of the above methods for preventing seroconversion to autoimmunity and T1D development using anti-TLR antibodies against, with a non-limiting examples of TLR 2, 4, 7, 9 are used in individuals with an increased amount of amyloid-producing bacteria belonging or not-belonging to Enterobacteriales and/or *E. coli*.

In one embodiment of the above methods for preventing seroconversion to autoimmunity and T1D development using anti-TLR antibodies against, with a non-limiting examples of TLR 2, 4, 7, 9 are used in individuals with an increased amount of bacteriophage nucleic acids of amyloid-producing bacteria belonging or not-belonging to Enterobacteriales and/or *E. coli*.

In one embodiment of the above methods for preventing seroconversion to autoimmunity and T1D development using anti-TLR antibodies against, with a non-limiting examples of TLR 2, 4, 7, 9 are used in individuals according to a longitudinal analysis had an increased amyloid-producing bacteria belonging or not-belonging to Enterobacteriales and/or *E. coli*, followed by their decrease over 1.5 fold within the next 12 months.

In one embodiment of the above methods for preventing seroconversion to autoimmunity and T1D development in individuals according to a longitudinal analysis had an increased amyloid-producing bacteria belonging or not-belonging to Enterobacteriales and/or *E. coli*, followed by their decrease over 2 fold within the next 12 months.

In one embodiment of the above methods for preventing seroconversion to autoimmunity and T1D development bacteriocins and/or colicins, and/or microcins against amyloid-producing bacteria belonging or not-belonging to Enterobacteriales and/or *E. coli* are used.

In one embodiment of the above methods for preventing seroconversion to autoimmunity and T1D development bacteria producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development bacteria producing bacteriocins and/or colicins, and/or microcins against amyloid-producing bacteria belonging or not-belonging to Enterobacteriales and/or *E. coli* are used for colonization of the gut following antibiotic usage to decrease bacterial intestinal growth.

In one embodiment of the above methods for preventing seroconversion to autoimmunity and T1D development bacteria producing bacteriocins and/or colicins, and/or microcins against amyloid-producing bacteria belonging or not-belonging to Enterobacteriales and/or *E. coli* are used for colonization of the gut following bacteriocins and/or colicins, and/or microcins usage to decrease Enterobacteriales intestinal growth.

In one embodiment of the above methods for preventing seroconversion to autoimmunity and T1D development genetically modified bacteria producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development synthetic bacteria producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development by administration of bacteria belonging to Enterobacteriales not producing amyloid, but producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development by administration genetically engineered *E. coli* lacking amyloid production (wherein the administration of genetically engineered *E. coli* is done once; two times; 1 time a week; two times a week; three times a week; for times a week; five times a week; six times a week; seven times a week; from 1 to 10 times daily; by intermittent courses; constantly; and *E. coli* is given by oral, IV, rectal administration).

In one embodiment of the above methods for preventing seroconversion to autoimmunity and T1D development, decrease of the abundance or elimination of amyloid-producing bacteria belonging or not-belonging to Enterobacteriales and/or *E. coli* is conducted by the method comprises replacing the microbiota with fecal microbiota transplantation (FMT) or non-fecal microbiota transplantation (non-FMT).

In one embodiment of the above methods for preventing seroconversion to autoimmunity and T1D development, decrease of the abundance or elimination of amyloid-producing bacteria, belonging or not-belonging to Enterobacteriales and/or *E. coli* is conducted by the composition comprising of bacterial spore population (wherein the spore population is in vegetative or spore form from natural sources including but not limited to feces, soil) or a subset of a microbial composition enriched with bacterial spores from 2-fold to 10,000-fold In one embodiment of the above methods for preventing seroconversion to autoimmunity and T1D development, decrease of the abundance or elimination of amyloid-producing bacteria belonging or not-belonging to Enterobacteriales and/or *E. coli* is conducted by regulation of amyloid-producing genes activity within gut *E. coli*.

In one embodiment of the above methods for preventing seroconversion to autoimmunity and T1D development, individuals according to a longitudinal analysis had an increased amyloid-producing bacteria belonging or not-belonging to Enterobacteriales and/or *E. coli*, followed by their decrease over 1.5-fold within the next 1 day, or 2 days, or 7 days, or 14 days, or 30 days, or any time up to 5 years.

In one embodiment of the above methods for preventing seroconversion to autoimmunity and T1D development, bacteriocins and/or colicins, and/or microcins against amyloid-producing bacteria belonging or not-belonging to Enterobacteriales and/or *E. coli* are used.

In one embodiment of the above methods for preventing seroconversion to autoimmunity and T1D development, bacteria-producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development, bacteria producing bacteriocins and/or colicins, and/or microcins against amyloid-producing bacteria belonging or not-belonging to Enterobacteriales and/or *E. coli* are used for colonization of the gut following antibiotic usage to decrease bacterial intestinal growth.

In one embodiment of the above methods for preventing seroconversion to autoimmunity and T1D development, genetically modified bacteria producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development, synthetic bacteria producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development, the methods comprise administration of bacteria belonging to Enterobacteriales not producing amyloid, but producing bacteriocins and/or colicins, and/or microcins against amyloid-producing bacteria belonging or not-belonging to Enterobacteriales and/or *E. coli* are used for colonization of the gut.

In one embodiment of the above methods for preventing seroconversion to autoimmunity and T1D development, the methods comprise administration of genetically engineered *E. coli* lacking amyloid production (wherein the administration of genetically engineered *E. coli* is done once; two times; 1 time a week; two times a week; three times a week; for times a week; five times a week; six times a week; seven times a week; from 1 to 10 times daily; by intermittent courses; constantly; and *E. coli* is given by oral, IV, rectal administration).

In one embodiment of the above methods for preventing seroconversion to autoimmunity and T1D development, the methods comprise administration of genetically engineered bacterial antagonists of *E. coli* (wherein the administration of genetically engineered microorganisms is done once; two times; 1 time a week; two times a week; three times a week; for times a week; five times a week; six times a week; seven times a week; from 1 to 10 times daily; by intermittent courses; constantly; and is given by oral, IV, rectal administration).

In one embodiment of the above methods for preventing seroconversion to autoimmunity and T1D development decrease of the abundance or elimination of amyloid-producing bacteria belonging or not-belonging to Enterobacteriales and/or *E. coli* is conducted by the method comprises replacing the microbiota with fecal microbiota transplantation (FMT) or non-fecal microbiota transplantation (non-FMT).

In one embodiment of the above methods for preventing seroconversion to autoimmunity and T1D development, decrease of the abundance or elimination of amyloid-producing bacteria belonging or not-belonging to Enterobacteriales and/or *E. coli* is conducted by replacing the microbiota with fecal microbiota transplantation (FMT) or non-fecal microbiota transplantation (non-FMT) enriched with *E. coli* antagonists such as *Bifidobacterium* with the non-limiting example of *Bifidobacterium* spp.

In one embodiment of the above methods for preventing seroconversion to autoimmunity and T1D by administration of *E. coli* antagonists such as *Bifidobacterium*. Examples of *Bifidobacterium* include, but are not limited to, *Bifidobacterium* spp.

In one embodiment of the above methods for preventing seroconversion to autoimmunity and T1D development, the method comprises administration of genetically engineered *E. coli* lacking amyloid production (wherein the administration of genetically engineered *E. coli* is done once; two times; 1 time a week; two times a week; three times a week; for times a week; five times a week; six times a week; seven times a week; from 1 to 10 times daily; by intermittent courses; constantly; and *E. coli* is given by oral, IV, rectal administration).

In one embodiment of the above methods for preventing seroconversion to autoimmunity and T1D development, the method comprises regulation of amyloidogenic and amyloid-associated genes activity within gut by Enterobacteriales bacteria and/or *E. coli*.

In one embodiment of the above methods for preventing seroconversion to autoimmunity and T1D development by elimination/knocking down of amyloidogenic and amyloid-associated genes activity within gut by Enterobacteriales bacteria and/or *E. coli*.

Also provided are methods for development of animal models to study T1D and other disease, the methods comprising the administration of bacterial amyloid or amyloid-producing bacteria belonging or not-belonging to Enterobacteriales and/or *E. coli* and/or their components to genetically relevant animals. Examples of such animals include, but are not limited to, NOD mice.

In various embodiments, the inhibition of the release is realized through prevention of prophages activation leading to the destruction of amyloid-producing bacteria biofilms, wherein prophages belong with a non-limiting examples to: Caudovirales—Myoviridae: Muvirus, Peduovirinae, Tevenvirinae, unclassified Myoviridae; Caudovirales—Podoviridae: Sepvirinae, Sepvirinae, unclassified Podoviridae; Caudovirales—Siphoviridae: Guernseyvirinae, Latnhdavirus, Latnhdavirus, Nonagvirus, unclassified Siphoviridae.

In one embodiment of the above aspects relating to preventing or treating sercoconversion to autoimmunity in T1D, the inactivation of amyloid-producing bacteria within microbiota is performed in a patient having at least one T1D susceptible HLA allele having an HLA haplotype (with a non-limiting example of e.g. HLA-DRB1-HLA-DQA1-HLA-DQB1; DR3; DR4; DQB1*0201; DR4-DQ8; DR3-DQ2; DR4, DQB1*0302; DR3, DQB1*0201; DRB1*0301-DQA1*0501-DQB1*0201; DRB1*0405-DQA1*0301-DQB1*0302, DRB1*0401-DQA1*0301-DQB*0302, DRB1*0402-DQA1*0301-DQB1*0302; DRB1*0404-DQA1*0301-DQB1*0302; DRB1*0801-DQB1*0401-DQB1*0402 (OR 1.25); DRB1*1501-DQA1*0102-DQB1*0602; DRB1*1401-DQA1*0101-DQB1*0503; DRB1*0701-DQA1*0201-DQB1*0303; DRB1*03:01-DQB1*02:01-DQA1*05:01; DRB1*03:01-DQB1*02:01-DQA1*05:01/DRB1*04-DQB1*03:02-DQA1*03; HLA-DR3/HLA-DR4; HLA-DRB1*03:01-HLA-DQA1*05:01-HLA-DQB1*02:01 and HLADRB1*04:04-HLA-DQA1*03:01-HLA-DQB1*03:02; HLA-DRB1*04:01-HLA-DQA1*03:01-HLA-DQB1*03:02 and HLA-DRB1*07:01-HLA-DQA1*02:01-HLA-DQB1*02:02) and/or other genes associated with T1D susceptibility (with a non-limiting example of e.g. ERBB3, IFIH1, PTPN22, CLEC16A, CTLA4, SH2B3, IL18RAP, COBL, HLA-DRB1, HLA-DQA2, INS, IL2RA, IFIH1, PPARG, KCNJ11, TCF7L2, PHTF1-PTPN22, ERBB3, C12orf30, SUOX-IKZF4, UBASH3A, PTPN2, EDG7, BACH2, GLIS3, RASGRP1, STAT4, STAT3, ERAP1, TNFAIP3, KIF5A/PIP4K2C, MHC, C10orf59, SH2B3, IL2RA, IL27, C6orf173, IL2, ORMDL3, CD69, IL10, IFIH1, BACH2, CTSH, PRKCQ, C1QTNF6, PGM1, KIAA0746, C6orf173, L2R, INS, C14orf181, PRKD2, HERC2, IFNG, IL26, DLK1, TYK2, IFIH1, SH2B3, ERBB3, CTSH, CENPW, SKAP2, PRKCQ, RNLS, SIRPG, CTRB2, LMO7, EFR3B, 6q27, TNFRSF11B, LOC100128081, FOSL2, HTR1A, RFN180, CUX2, AIRE, FoxP3, STAT3, IFIH1, HIP14, ERBB3, Ins-VNTR, and IDDM 2.

In one embodiment of the above aspects relating to preventing or treating sercoconversion to autoimmunity in T1D, the inactivation of amyloid-producing bacteria within microbiota is performed in a patient having at least one T1D susceptible HLA allele having an HLA haplotype (with a non-limiting example of e.g. HLA-DRB1-HLA-DQA1-HLA-DQB1; DR3; DQB1*0201; DR4-DQ8; DR3-DQ2; DR4, DQB1*0302; DR3, DQB1*0201 DR4 DRB1*0301-DQA1*0501-DQB1*0201; DRB1*0405-DQA1*0301-DQB1*0302, DRB1*0401-DQA1*0301-DQB*0302, DRB1*0402-DQA1*0301-DQB1*0302; DRB1*0404-DQA1*0301-DQB1*0302; DRB1*0801-DQB1*0401-DQB1*0402 (OR 1.25); DRB1*1501-DQA1*0102-DQB1*0602; DRB1*1401-DQA1*0101-DQB1*0503; DRB1*0701-DQA1*0201-DQB1*0303; DRB1*03:01-DQB1*02:01-DQA1*05:01; DRB1*03:01-DQB1*02:01-DQA1*05:01/DRB1*04-DQB1*03:02-DQA1*03; HLA-DR3/HLA-DR4; HLA-DRB1*03:01-HLA-DQA1*05:01-HLA-DQB1*02:01 and HLADRB1*04:04-HLA-DQA1*03:01-HLA-DQB1*03:02; HLA-DRB1*04:01-HLA-DQA1*03:01-HLA-DQB1*03:02 and HLA-DRB1*07:01-HLA-DQA1*02:01-HLA-DQB1*02:02) and/or other genes associated with T1D susceptibility (with a non-limiting example of e.g. ERBB3, IFIH1, PTPN22, CLEC16A, CTLA4, SH2B3, IL18RAP, COBL, HLA-DRB1, HLA-DQA2, INS, IL2RA, IFIH1, PPARG, KCNJ11, TCF7L2, PHTF1-PTPN22, ERBB3, C12orf30, SUOX-IKZF4, UBASH3A, PTPN2, EDG7, BACH2, GLIS3, RASGRP1, STAT4, STAT3, ERAP1, TNFAIP3, KIF5A/PIP4K2C, MHC, C10orf59, SH2B3, IL2RA, IL27, C6orf173, IL2, ORMDL3, CD69, IL10, IFIH1, BACH2, CTSH, PRKCQ, C1QTNF6, PGM1, KIAA0746, C6orf173, L2R, INS, C14orf181, PRKD2, HERC2, IFNG, IL26, DLK1, TYK2, IFIH1, SH2B3, ERBB3, CTSH, CENPW, SKAP2, PRKCQ, RNLS, SIRPG, CTRB2, LMO7, EFR3B, 6q27, TNFRSF11B, LOC100128081, FOSL2, HTR1A, RFN180, CUX2, AIRE, FoxP3, STAT3, IFIH1, HIP14, ERBB3, Ins-VNTR, and IDDM 2.

In one embodiment of the above aspects relating to prevention, or inhibition of T1DAMP (e.g. amyloid) formation may be performed in a patient together with evaluation at least one T1D susceptible HLA allele having an HLA haplotype (with a non-limiting example of e.g. HLA-DRB1-HLA-DQA1-HLA-DQB1; DR3; DQB1*0201; DR4-DQ8; DR3-DQ2; DR4, DQB1*0302; DR3, DQB1*0201; DR4; DRB1*0301-DQA1*0501-DQB1*0201; DRB1*0405-DQA1*0301-DQB1*0302, DRB1*0401-DQA1*0301-DQB*0302, DRB1*0402-DQA1*0301-DQB1*0302; DRB1*0404-DQA1*0301-DQB1*0302; DRB1*0801-DQB1*0401-DQB1*0402 (OR 1.25); DRB1*1501-DQA1*0102-DQB1*0602; DRB1*1401-DQA1*0101-DQB1*0503; DRB1*0701-DQA1*0201-DQB1*0303; DRB1*03:01-DQB1*02:01-DQA1*05:01; DRB1*03:01-DQB1*02:01-DQA1*05:01/DRB1*04-DQB1*03:02-DQA1*03; HLA-DR3/HLA-DR4; HLA-DRB1*03:01-HLA-DQA1*05:01-HLA-DQB1*02:01 and HLADRB1*04:04-HLA-DQA1*03:01-HLA-DQB1*03:02; HLA-DRB1*04:01-HLA-DQA1*03:01-HLA-DQB1*03:02 and HLA-DRB1*07:01-HLA-DQA1*02:01-HLA-DQB1*02:02) and/or other genes associated with T1D susceptibility (with a non-limiting example of e.g. ERBB3, IFIH1, PTPN22, CLEC16A, CTLA4, SH2B3, IL18RAP, COBL, HLA-DRB1, HLA-DQA2, INS, IL2RA, IFIH1, PPARG, KCNJ11, TCF7L2, PHTF1-PTPN22, ERBB3, C12orf30, SUOX-IKZF4, UBASH3A, PTPN2, EDG7, BACH2, GLIS3, RASGRP1, STAT4, STAT3, ERAP1, TNFAIP3, KIF5A/PIP4K2C, MHC, C10orf59, SH2B3, IL2RA, IL27, C6orf173, IL2, ORMDL3, CD69, IL10, IFIH1, BACH2, CTSH, PRKCQ, C1QTNF6, PGM1, KIAA0746, C6orf173, L2R, INS, C14orf181, PRKD2, HERC2, IFNG, IL26, DLK1, TYK2, IFIH1, SH2B3, ERBB3, CTSH, CENPW, SKAP2, PRKCQ, RNLS, SIRPG, CTRB2, LMO7, EFR3B, 6q27, TNFRSF11B, LOC100128081, FOSL2, HTR1A, RFN180, CUX2, AIRE, FoxP3, STAT3, IFIH1, HIP14, ERBB3, Ins-VNTR, and IDDM 2.

In one embodiment of the above aspects relating to prevention, or inhibition of T1DAMP (e.g. amyloid), formation may be performed in a patient together with evaluation at least one T1D susceptible HLA allele having an HLA haplotype (with a non-limiting example of e.g. HLA-DRB1-HLA-DQA1-HLA-DQB1; DR3; DQB1*0201; DR4-DQ8; DR3-DQ2; DR4, DQB1*0302; DR3, DQB1*0201 DR4 DRB1*0301-DQA1*0501-DQB1*0201; DRB1*0405-DQA1*0301-DQB1*0302, DRB1*0401-DQA1*0301-DQB*0302, DRB1*0402-DQA1*0301-DQB1*0302; DRB1*0404-DQA1*0301-DQB1*0302; DRB1*0801-DQB1*0401-DQB1*0402 (OR 1.25); DRB1*1501-DQA1*0102-DQB1*0602; DRB1*1401-DQA1*0101-DQB1*0503; DRB1*0701-DQA1*0201-DQB1*0303; DRB1*03:01-DQB1*02:01-DQA1*05:01; DRB1*03:01-DQB1*02:01-DQA1*05:01/DRB1*04-DQB1*03:02-DQA1*03; HLA-DR3/HLA-DR4; HLA-DRB1*03:01-HLA-DQA1*05:01-HLA-DQB1*02:01 and HLADRB1*04:04-HLA-DQA1*03:01-HLA-DQB1*03:02; HLA-DRB1*04:01-HLA-DQA1*03:01-HLA-DQB1*03:02 and HLA-DRB1*07:01-HLA-DQA1*02:01-HLA-DQB1*02:02) and/or other genes associated with T1D susceptibility (with a non-limiting example of e.g. ERBB3, IFIH1, PTPN22, CLEC16A, CTLA4, SH2B3, IL18RAP, COBL, HLA-DRB1, HLA-DQA2, INS, IL2RA, IFIH1, PPARG, KCNJ11, TCF7L2, PHTF1-PTPN22, ERBB3, C12orf30, SUOX-IKZF4, UBASH3A, PTPN2, EDG7, BACH2, GLIS3, RASGRP1, STAT4, STAT3, ERAP1, TNFAIP3, KIF5A/PIP4K2C, MHC, C10orf59, SH2B3, IL2RA, IL27, C6orf173, IL2, ORMDL3, CD69, IL10, IFIH1, BACH2, CTSH, PRKCQ, C1QTNF6, PGM1, KIAA0746, C6orf173, L2R, INS, Cl4orf181, PRKD2, HERC2, IFNG, IL26, DLK1, TYK2, IFIH1, SH2B3, ERBB3, CTSH, CENPW, SKAP2, PRKCQ, RNLS, SIRPG, CTRB2, LMO7, EFR3B, 6q27, TNFRSF11B, LOC100128081, FOSL2, HTR1A, RFN180, CUX2, AIRE, FoxP3, STAT3, IFIH1, HIP14, ERBB3, Ins-VNTR, IDDM 2.

Additional Embodiments

1. A method for diagnosing, preventing, treating or diagnosis seroconversion and/or T1D consequences thereof, said method comprised of (i) inactivation of amyloid-producing bacteria thereof within microbiota and/or (ii) inactivation of amyloid-producing bacteria getting from the outer environment to microbiota, gastrointestinal tract, bodily fluid(s) or tissue(s) of a mammal and/or (iii) inactivation of T1DAMP production by microbiota bacteria and/or (iv) inactivation of bacteria-derived T1DAMP present in microbiota, bodily fluid(s) or tissue(s) of the mammal and/or (v) inhibiting release of bacteria-derived T1DAMP from biofilm and/or bacteria to gastrointestinal tract, bodily fluid(s) or tissue(s) of the mammal and/or (vi) inhibiting entry of bacteria-derived T1DAMP to microbiota, gastrointestinal tract, bodily fluid(s) or tissue(s) of the mammal and/or (vii) inhibiting effect of bacteria-derived T1DAMP and/or its complexes to trigger T1D.
2. The method of embodiment 1, wherein the treatment or prevention of T1D is effective to prevent colonization of the mammal with amyloid-producing bacteria.
3. The method of embodiment 1 or 2, wherein the inactivation of amyloid-producing bacteria within microbiota comprises prevention of colonization with amyloid-producing bacteria starting from the birth up to 50 years old.
4. The method of embodiment 1 or 2, wherein the inactivation of amyloid-producing bacteria within microbiota is performed in a mammal expressing TID-susceptible HLA alleles.
5. The method of embodiment 1 or 2, wherein the inactivation of amyloid-producing bacteria within microbiota comprises prevention of transfer of amyloid-producing bacteria from parents, including those happening during childbirth and breastfeeding.
6. The method of embodiment 1 or 2, wherein the inactivation of amyloid-producing bacteria within microbiota comprises prevention of colonization with amyloid-producing bacteria by the use of microorganisms or their by-products including antagonists of amyloid-producing bacteria.
7. The composition of embodiment 6 wherein said strain(s) is from one or more of Bacteroidales, Lactobacillales, Erysipelotrichales, Coriobacteriales, Clostridiales, Bacillales, and Bifidobacteriales orders.
8. The composition of embodiment 6 wherein said strain(s) is from one or more of *B. infantis*, lactate and SCFAs.
9. The method of embodiment 1 or 2, wherein the inactivation of amyloid-producing bacteria within microbiota comprises prevention of colonization with amyloid-producing bacteria by the use for the colonization of modified strains of these microorganisms characterized by being non-amyloid-producing strains or synthesis of the reduced amounts of amyloid.
10. The method of embodiment 1 or 2, wherein the inactivation of amyloid-producing bacteria within microbiota comprises the prevention of colonization with amyloid-producing bacteria by the use of one or more chemical, physical, or biological agents.
11. The method of embodiment 1 or 2, wherein the inactivation of amyloid-producing bacteria within microbiota comprises the microbiota replacement.
12. The method of embodiment 1 or 2, wherein the inactivation of amyloid-producing bacteria within microbiota comprises the prevention of colonization with amyloid-producing bacteria by the alteration of bacterial adhesion.
13. The method of embodiment 1 or 2, wherein the inactivation of amyloid-producing bacteria within microbiota comprises the prevention of colonization with amyloid-producing bacteria by n-Heptyl such as α-D-mannose glycopolymers, thiazolylmannosides.
14. The method of embodiment 1 or 2, wherein the inactivation of amyloid-producing bacteria within microbiota comprises the prevention of colonization with amyloid-producing bacteria by transthyretin.
15. The method of embodiment 1 or 2, wherein the inactivation of amyloid-producing bacteria within microbiota comprises the prevention of colonization with amyloid-producing bacteria by human transthyretin and/or engineered nontetramer-forming monomer (M-TTR, F87M/L110M).
16. The method of embodiment 1, further comprising vaccination performed against amyloid-producing bacteria.
17. The method of embodiment 1 or 13, wherein the prevention, inactivating or colonization of gut with amyloid-producing bacteria within microbiota comprises the prevention of colonization with amyloid-producing bacteria by vaccination or immunization of the mammal against Enterobacteriales bacteria.
18. The method of embodiment 1 or 5, wherein the prevention, inactivating or colonization of gut with amyloid-producing bacteria within microbiota comprises the prevention of colonization with amyloid-producing bacteria by vaccination or immunization of the mammal against *E. coli*, wherein the vaccination is performed in a mammal comprising a T1D susceptible HLA allele or an increased amount of *E. coli* as compared to a mammal not susceptible to T1D.
19. The method of embodiment 1 wherein the prevention of amyloid, inactivating or colonization of gut with amyloid-producing bacteria within microbiota wherein the therapeutic agents are anti-amyloid-producing bacterial antibodies.
20. The method of embodiment 1 and 2, wherein the inactivation of amyloid-producing bacteria within microbiota comprises the prevention of colonization with amyloid-producing bacteria by the alteration of one or more receptors present on the surface of the amyloid-producing bacteria or the receptors of the macroorganisms or hormones and other mediators associated with higher colonization of amyloid-producing bacteria.
21. The method of embodiment 1, wherein the prevention of T1D is by alteration of prenatal immunity against amyloid-producing bacteria and T1DAMP.
22. The method of any one of embodiments 1 to 20, wherein the inactivation of gut with amyloid-producing bacteria within microbiota is performed in a mammal comprising a T1D susceptible HLA allele or an increased amount of E. coli as compared to a mammal not susceptible to T1D.
23. The method of embodiment 1, wherein the treatment or prevention of T1D comprises decrease of colonization with amyloid-producing bacteria.
24. The method of embodiment 1 or 21, wherein the inactivation of amyloid-producing bacteria within microbiota comprises the decrease of colonization with amyloid-producing bacteria by the use of chemical, physical, biological agents, the use of microorganisms or their by-products including antagonists of amyloid-producing bacteria.
25. The method of embodiment 1 or 21, wherein the comprises the use of antimicrobials active against amyloid-producing bacteria.
26. The method of embodiment 1 or 21, wherein the inactivation of amyloid-producing bacteria within microbiota comprises the alteration of bacterial adhesion.
27. The method of embodiment 1 or 21, wherein the inactivation of amyloid-producing bacteria within microbiota by genome editing, triggering mutations and editing of bacterial genomes leading to alterations of bacterial adhesion, including, but limited to those associated with E. coli pili, with the methods not limited to CRISPR.
28. The method of embodiment 1 or 21, wherein the inactivation of amyloid-producing bacteria within microbiota comprises triggering mutations and editing in a bacterial genome one or more of afa-dra, daaD, tsh, vat, ibeA, fyuA, mat, sfa-foc, malX, pic, irp2, papC, fimH; PapAH papEF, bmaE, sfa/focDE, papC, focG, sfaI, sfa II, sfaS, aah, aidA, fasA, faeG, bfpA, eaeA, Paa, fasA, faeG, fedA, fanC, genes; sfaY; Cpx pathway, wherein the inactivation is effective to alter bacterial adhesion.
29. The method of embodiment 1 or 19, wherein the inactivation of amyloid-producing bacteria within microbiota comprises triggering mutations and editing of bacterial genomes leading to alterations of bacterial adhesion, including, but limited to those associated with E. coli pili, with the methods not limited to CRISPR.
30. The method of any one of embodiments 21 to 29, wherein the inactivation of amyloid-producing bacteria within microbiota comprises vaccinating a mammal against Enterobacteriales, wherein the mammal comprises a T1D-susceptible HLA allele, or an increased amount of E. coli as compared to a mammal not susceptible to T1D.
31. The method of embodiment 1 or 21, wherein the inactivation of amyloid-producing bacteria within microbiota by the use of compounds that regulate pilus biogenesis.
32. A composition for the decrease of colonization with amyloid-producing bacteria, the composition comprising one or more of fosfomycin, Doxycycline, Ciprofloxacin, Trimethoprim/sulfamethoxazole, Levofloxacin, Amoxicillin, Aztreonam, Nitrofurantoin, Ceftriaxone, imipenem, and Rifaximin.
33. A composition comprising FimH antagonists, such as n-Heptyl α-D-mannose glycopolymers, methyl R-D-mannoside, thiazolylmannosides leading to an alteration of amyloid-producing bacteria adhesion.
34. The composition of embodiment 32, further comprising FimH antagonists, such as n-Heptyl α-D-mannose glycopolymers, methyl R-D-mannoside, thiazolylmannosides leading to an alteration of amyloid-producing bacteria adhesion.
35. The composition of embodiment 1 wherein the inactivation of amyloid-producing bacteria within microbiota wherein the therapeutic agents are anti-amyloid-producing bacterial antibodies.
36. A composition comprising a pilicide, such as n-Heptyl α-D-mannose glycopolymers, thiazolylmannosides leading to an alteration of amyloid-producing bacteria adhesion.
37. The composition of any one of embodiments 33-35, further comprising a pilicide, such as n-Heptyl α-D-mannose glycopolymers, thiazolylmannosides leading to an alteration of amyloid-producing bacteria adhesion.
38. A composition comprising one or more pilicides effective to alter amyloid-producing bacteria adhesion, such as but not limited to one or more of the following exemplary ring-fused 2-pyridones:
7-(1-naphthylmethyl)-5-oxo-8-phenyl-2,3,6,7-tetrahydro-5H-[1,3]thiazolo[3,2-a]pyridine-3-carboxylic acid
8-cyclopropyl-7-(1-naphthylmethyl)-5-oxo-2,3,6,7-tetrahydro-5H-[1,3]thiazolo[3,2-a]pyridine-3-carboxylic acid
7-(1-naphthylmethyl)-5-oxo-8-pentyl-2,3,6,7-tetrahydro-5H-[1,3]thiazolo[3,2-a]pyridine-3-carboxylic acid
8-(4-bromophenyl)-7-(1-naphthylmethyl)-5-oxo-2,3,6,7-tetrahydro-5H-[1,3]thiazolo[3,2-a]pyridine-3-carboxylic acid
7-(1-naphthylmethyl)-5-oxo-8-phenyl-2,3-dihydro-5H-[1,3]thiazolo[3,2-a]pyridine-3-carboxylic acid, lithium salt
8-cyclopropyl-7-(1-naphthylmethyl)-5-oxo-2,3-dihydro-5H-[1,3]thiazolo[3,2-a]pyridine-3-carboxylic acid, lithium salt
7-methyl-5-oxo-8-phenyl-2,3-dihydro-5H-[1,3]thiazolo[3,2-a]pyridine-3-carboxylic acid, lithium salt
6-dimethylaminomethyl-7-(1-naphthylmethyl)-5-oxo-8-phenyl-2,3-dihydro-5H-[1,3]thiazolo[3,2-a]pyridine-3-carboxylic acid, lithium salt
6-morpholinomethyl-7-(1-naphthylmethyl)-5-oxo-8-phenyl-2,3-dihydro-5H-[1,3]thiazolo[3,2-a]pyridine-3-carboxylic acid, lithium salt
8-cyclopropyl-6-morpholinomethyl-7-(1-naphthylmethyl)-5-oxo-2,3-dihydro-5H-[1,3]thiazolo[3,2-a]pyridine-3-carboxylic acid, lithium salt
6-dimethylaminomethyl-7-methyl-5-oxo-8-phenyl-2,3-dihydro-5H-[1,3]thiazolo[3,2-a]pyridine-3-carboxylic acid, lithium salt.
39. The method of any one of embodiments 21 to 31, wherein the prevention, inactivating or colonization of gut with amyloid-producing bacteria within microbiota is performed in a mammal comprising T1D susceptible HLA alleles or an increased amount of E. coli as compared to a mammal not susceptible to T1D.

40. The method of embodiment 1, wherein the treatment or prevention of T1D comprises inactivation of amyloid and amyloid-associated complexes production by microbiota bacteria within a human.
41. The method of embodiment 1 or 40, wherein the inactivation of bacterial-derived amyloid within microbiota comprises triggering mutations and editing of bacterial genomes leading to alterations of amyloid-associated genes.
42. The method of embodiment 1 or 40, wherein the inactivation of bacterial-derived amyloid within microbiota by triggering mutations and editing of bacterial genomes leading to alterations of the activity of amyloid associated genes and decrease of amyloid synthesis and/or formation.
43. The method of embodiment 1 or 40, wherein the inactivation of bacterial-derived amyloid within microbiota by triggering mutations and editing of bacterial genomes leading to alterations of the activity of amyloid associated genes and decrease of amyloid synthesis and/or formation is done ex vivo in E. coli isolated from patient and then, modified strains are used for the recolonization.
44. The method of embodiment 1 or 40, wherein the inactivation of bacterial-derived amyloid within microbiota by altering activity (e.g. triggering mutations, editing of bacterial genomes leading to alterations of the activity, regulating gene activity, altering the number) of proteins with anti-amyloid chaperoning activity.
45. The method of any one of embodiments 40 to 44, wherein the inactivation of amyloid and T1DAMP is performed within microbiota of the human, and wherein the human comprises a T1D-susceptible HLA allele or an increased amount of E. coli as compared to a mammal not susceptible to T1D.
46. The method of embodiment 1, wherein the inactivation of T1DAMP and/or amyloid biogenesis present in microbiota, body fluid(s) or tissue(s) of the mammal.
47. The method of embodiment 1, wherein the inactivation of bacterial-derived T1DAMP within microbiota by inhibition of amyloid and/or curli assembly.
48. The method of embodiment 1 or 45, wherein the inactivation of bacterial-derived T1DAMP within microbiota by induction of T1DAMP (e.g., amyloid and/or curli) disassembly and/or dissociation.
49. The method of embodiment 1 or 45, wherein the inactivation of bacterial-derived T1DAMP within microbiota by prevention of amyloid aggregation including formation of b-structure.
50. The method of embodiment 1 or 45, wherein the inactivation of bacterial-derived amyloid within microbiota by prevention of amyloid and/or its complexes release from the biofilms.
51. The method of embodiment 1 or 45, wherein the inactivation of bacterial-derived T1DAMP within microbiota by binding amyloid and/or its complexes.
52. The method of embodiment 1 or 45, wherein the inactivation of bacterial-derived T1DAMP within microbiota by preventing curli formation by prevention formation of amyloid-DNA complexes.
53. The method of embodiment 1 or 45, wherein the inactivation of bacterial-derived T1DAMP within microbiota by destruction of curli, affecting components of amyloid-DNA complexes.
54. The method of embodiment 1 or 42, wherein the prevention of bacterial-derived T1DAMP is achieved by vaccination.
55. A composition for use in the method of any one of embodiments 1, 45, and 50, the composition comprising one or more sorbents, such as Diosmectite, Di-Tri Octahedral Smectite, coals, colloidal dioxide silica, polymethylsiloxane polyhydrate, leading to an adhesion of amyloid and amyloid-DNA complexes.
56. A composition for use in the method of embodiment 1 or 45, wherein the composition is effective for inactivation of bacterial-derived T1DAMP within microbiota, and wherein the composition comprises deoxyribonuclease for prevention of amyloid-DNA complex formation.
57. A composition for use in the method of embodiment 1 or 45, wherein the composition is effective for inactivation of bacterial-derived T1DAMP within microbiota, and wherein the composition is comprised a nuclease for prevention of amyloid-DNA complex formation, e.g., T7 Endonuclease I, Mung Bean Nuclease, Nuclease BAL-31, Nuclease P, Deoxyribonuclease IV, Deoxyribonuclease I, Deoxyribonuclease II, frequently cutting restriction enzymes, e.g. EcoRI, HindIII, HaeIII, endonucleases with no proteolytic activity, e.g. Benzonase nuclease and the like.
58. A composition for use in the method of embodiment 1, further comprising an anti-amyloid antibody, an anti-amyloid-DNA complex antibody, or an anti-bacterial-DNA antibody.
59. A composition for use in the method of embodiment 1 or 42, wherein the composition is effective for inactivation of bacterial-derived T1DAMP within microbiota, and wherein the composition comprises an antibody that specifically reacts against any part and/or component of bacterial curli.
60. A composition for use in the method of embodiment 1 or 42, wherein the composition is effective for inactivation of bacterial-derived T1DAMP within microbiota and inhibition of amyloid biogenesis of the bacterial-derived T1DAMP within the microbiota, wherein the composition comprises a curlicide, such as one or more of the following non-limiting examples of curlicides: ring-fused 2-pyridone, bicyclic 2-pyridones, AA-861 (2-(12-hydroxydodeca-5,10-diynyl)-3,5,6-trimethyl-p-benzoquinone, 2,3,5-trimethyl6-(12-hydroxy-5,10-dodecadiynyl)-1,4-benzoquinone), tafamidis, epi-gallocatechine gallate, rifapentine, Vitisin B, 8-cyclopropyl-7-(1-naphthylmethyl)-5-oxo-2,3-dihydro-5H-[1,3]thiazolo[3,2-a]pyridine-3-carboxylic acid 7-(1-naphthylmethyl)-5-oxo-8-(3-trifluoromethylphenyl)-2,3-dihydro-5H-[1,3]thiazolo[3,2-a]pyridine-3-carboxylic acid, lithium salt 7-(1-naphthylmethyl)-5-oxo-8-phenyl-2,3-dihydro-5H-[1,3]thiazolo[3,2-a]pyridine-3-carboxylic acid N3-phenyl-8-cyclopropyl-7-(1-naphthylmethyl)-5-oxo-2,3-dihydro-5H-[1,3]thiazolo[3,2-a]pyridine-3-carboxamide 8-cyclopropyl-7-[3-(3,5-dimethyl-1H-2-pyrrolyl)-3-(3,5-dimethyl-2H-2-pyrrolyliden)propyl]-5-oxo-2,3-dihydro-5H-[1,3]thiazolo[3,2-a]pyridine-3-carboxylic acid, N,N'-difluoroboronium 8-(3,4-difluorophenyl)-7-(1-naphthylmethyl)-5-oxo-2,3-dihydro-5H-[1,3]thiazolo[3,2-a]pyridine-3-carboxylic acid 8-(4-bromophenyl)-7-(1-naphthylmethyl)-5-oxo-2,3-dihydro-5H-[1,3]thiazolo[3,2-a]pyridine-3-carboxylic acid 7-(1-naphthylmethyl)-5-oxo-8-phenyl-2,3,6,7-tetrahydro-5H-[1,3]thiazolo[3,2-a]pyridine-3-carboxylic acid 8-cyclopropyl-7-(1-naphthylmethyl)-5-oxo-2,3,6,7-tetrahydro-5H-[1,3]thiazolo[3,2-a]pyridine-3-carboxylic acid 7-(1-naphthylmethyl)-5-oxo-8-pentyl-2,3,6,7-tetrahydro-5H-[1,3]thiazolo[3,2-a]pyridine-3-carboxylic acid 8-(4-bromophenyl)-7-(1-naphthylmethyl)-5-oxo-2,3,6,7-tetrahydro-5H-[1,3]thiazolo[3,2-a]pyridine-3-carboxylic acid 7-(1-naphthylmethyl)-5-oxo-8-phenyl-2,3-dihydro-5H-[1,3]thiazolo[3,2-a]pyridine-3-carboxylic acid, lithium salt 8-cyclopropyl-7-(1-naphthylmethyl)-5-oxo-2,3-dihydro-5H-[1,3]thiazolo[3,2-a]pyridine-3-carboxylic acid, lithium salt 7-methyl-5-oxo-8-phenyl-2,3-dihydro-5H-[1,3]thiazolo[3,2-a]pyridine-3-carboxylic acid, lithium salt 6-dimethylaminomethyl-7-(1-naphthylmethyl)-5-oxo-8-phenyl-2,3-dihydro-5H-[1,3]thiazolo[3,2-a]pyridine-3-carboxylic acid, lithium salt 6-morpholinomethyl-7-(1-naphthylmethyl)-5-oxo-8-phenyl-2,3-dihydro-5H-[1,3]thiazolo[3,2-a]pyridine-3-carboxylic acid, lithium salt 8-cyclopropyl-6-morpholinomethyl-7-(1-naphthylmethyl)-5-oxo-2,3-dihydro-5H-[1,3]thiazolo[3,2-a]pyridine-3-carboxylic acid, lithium salt 6-dimethylaminomethyl-7-methyl-5-oxo-8-phenyl-2,3-dihydro-5H-[1,3]thiazolo[3,2-a]pyridine-3-carboxylic acid, lithium salt.

61. The method of any one of embodiments 46 to 54, wherein the method is performed in a mammal comprising a T1D susceptible HLA allele or an increased amount of *E. coli* as compared to a mammal not susceptible to T1D.

62. The method of embodiment 1, wherein the inhibiting release of bacteria-derived T1DAMP to microbiota, gastrointestinal tract, body fluid(s) or tissue(s) of the mammal.

63. The method of embodiment 1 or 61, wherein the inhibition of the release is realized through the prevention of bacteriophages-induced destruction of amyloid-producing bacteria biofilms.

64. The method of embodiment 1 or 61, wherein the inhibition of the release is realized through prevention of prophages activation leading to the destruction of amyloid-producing bacteria biofilms.

65. The method of embodiment 1 or 61, wherein the inhibition of the release happens in biofilms formed by Enterobacteriales.

66. The method of embodiment 1 or 61, wherein the inhibition of the release happens in biofilms formed by *E. coli*.

67. The method of embodiment 1 or 61, wherein the inhibition of the release comprises prevention of prophage activation, wherein prevention of prophage activation is effective to destroy amyloid-producing bacteria biofilms, optionally wherein the prophage is Caudovirales Myoviridae (such as Muvirus, Peduovirinae, Tevenvirinae, unclassified Myoviridae), Caudovirales Podoviridae (such as Sepvirinae, Sepvirinae, unclassified Podoviridae), Caudovirales Siphoviridae (such as Guernseyvirinae, Lambdavirus, Lambdavirus, Nonagvirus, or unclassified Siphoviridae).

68. The method of any one of embodiments 61 to 66, wherein is performed in a mammal comprising a T1D susceptible HLA allele or an increased amount of *E. coli* as compared to a mammal not susceptible to T1D.

69. The method of embodiment 1, wherein the inhibiting entry of bacteria-derived T1DAMP to microbiota, gastrointestinal tract, body fluid(s) or tissue(s) of the mammal comprises modification of barrier permeability such as mucosal permeability, intestinal permeability, induction of a mucin synthesis to microbial-derived amyloid and its complexes.

70. A composition for use in the method of embodiment 1, 68, or 69, wherein the composition comprises one or more members of *Clostridium, Eubacterium, Staphylococcus, Coprococcus, Lactobacillus, Faecalibacterium, Catenibacterium, Collinsella, Blautia, Bifidobacterium, Dorea,* and *Prevotella* genera.

71. The composition for embodiment 1, 68, or 69, wherein the composition comprises one or more of glycylglycyl-L-valyl-L-leucyl-L-valyl-L-glutaminyl-L-prolyl-glycine ("Larazotide"); methyl 7-[(1R,2R,3R)-3-hydroxy-2-[(E)-4-hydroxy-4-methyloct-1-enyl]-5-oxocyclopentyl]heptanoate; L-Glutamine; fructooligosaccharides; Vitamin D; lipoic acid; polyphenolic compounds; and tryptophan indoles to reduce the intestinal permeability to bacterial amyloid.

72. The method of embodiment 1, wherein the inhibiting effect of bacteria-derived T1DAMP to trigger T1D.

73. The method of embodiment 1 or 71, wherein TLR are blocked to bacterial amyloid and/or their complexes.

74. The method of embodiment 1 or 71, wherein TLR are TR2 and TLR9.

75. The composition for use in the method of embodiment 1 or 71, wherein the composition comprises oligonucleotides/suppressive oligonucleotides (non-limiting example: 5'-TGCTTGCAAGCTTGCAAGCA-3') are used, and/or gene-editing tools (CRISPR) to inactivate TLR from the effect of bacterial amyloids and/or their complexes.

76. The method of embodiment 1 or 71, wherein the composition of embodiment 75 is used for vaccinating a mammal against bacterial-amyloid and/or amyloid complexes.

77. The method of embodiment 1 wherein the evaluation of predisposable to seroconversion and T1D comprises quantitative and/or qualitative analysis of amyloid-producing bacteria in microbiota.

78. The method of embodiment 1 wherein the evaluation of predisposable to seroconversion and T1D comprises quantitative and/or qualitative analysis of bacterial-amyloid and/or amyloid complexes in microbiota and/or biological fluids and tissues.

79. The method of embodiment 1 wherein the evaluation of predisposable to seroconversion and T1D comprises quantitative and/or qualitative analysis of bacterial-amyloid and/or amyloid complexes in microbiota and/or biological fluids and tissues.

80. The method of embodiment 1 wherein the evaluation of predisposable to seroconversion and T1D comprises quantitative and/or qualitative analysis of Enterobacteriales components thereof in microbiota and/or biological fluids and tissues.

81. The method of embodiment 1 wherein the evaluation of predisposable to seroconversion and T1D comprises quantitative and/or qualitative analysis of *E. coli* components thereof in microbiota and/or biological fluids and tissues.

82. The method of embodiment 1 wherein the evaluation of predisposable to seroconversion and T1D comprises quantitative and/or qualitative analysis of *E. coli* components thereof and alteration of microbiota associated with *E. coli* abundance alterations in microbiota and/or biological fluids and tissues.

83. The method of embodiment 1 wherein the evaluation of predisposable to seroconversion and T1D is done by the quantitative and/or qualitative analysis of bacterial amyloid in microbiota and/or biological fluids and tissues.
84. The method of any one of embodiments 1 and 76-83, comprising analyzing T1D susceptible HLA alleles.
85. The method of any one of embodiments 1 and 76-83, comprising evaluating in addition to Genetic Risk Scores for Type 1 Diabetes Prediction and Diagnosis; to Composite T1D prediction scores and or accurate T1D predictive model.
86. The method of any one of embodiments 1 and 76-83, wherein the method is performed as a screening across all or part of a general population.
87. The method of any one of embodiments 1 and 76-83, wherein the method is performed as a screening across all or part of a general population comprising members from birth up to 20 years of age.
88. The method of any one of embodiments 1 and 76-83, wherein the method is performed to evaluate in connection with an endpoint in a clinical trial.
89. The method of any one of embodiments 1 and 76-83, wherein the method is performed to evaluate in connection with a patient population to be enrolled in a clinical trial.
90. The method of any one of embodiments 1 and 76-83, wherein the method is performed to evaluate in connection with the development of preventive medicines.
91. The method of embodiment 1, wherein the method is used together with administration of one or more immunosuppressants to the mammal.
92. The method of embodiment 1, wherein the method is used together with interventions with autoimmunity prior to T1D development.
93. The method of embodiment 1, wherein the method is used together with the use of insulin for the prevention of T1D.
94. The method of embodiment 1, wherein the prevention of T1D is by alteration of human receptors to T1DAMP.
95. The method of embodiment 1, wherein the quantitative and/or qualitative analysis of amyloid-producing bacteria in microbiota and/or phages and components thereof associated with amyloid-producing bacteria and/or HLA alleles and/or PTPNN2 are used for the diagnosis and to determine the time onset of seroconversion, T1D or its severity.
96. The method of embodiment 1, wherein the evaluation of predisposable to seroconversion and T1D is done by the quantitative and/or qualitative analysis of bacteriophages amyloid-producing bacteria in microbiota and/or phages and components thereof and/or HLA alleles and/or antibodies are used for the diagnosis as biomarkers and can be used as an endpoint in clinical trials as a surrogate marker for the high risk of type 1 diabetes, and prevention of T1D development.
97. The method of embodiment 1, wherein the quantitative and/or qualitative analysis of amyloid-producing bacteria in microbiota and/or phages and components thereof associated with amyloid-producing bacteria and/or HLA alleles are used for the diagnosis as biomarkers and can be used in clinical trials as a surrogate marker preventive endpoint for t1d and seroconversion.
98. The method of embodiment 1, wherein the quantitative and/or qualitative analysis of amyloid-producing bacteria in microbiota and/or ages associated with amyloid-producing bacteria and/or HLA alleles are used for the diagnosis as biomarkers and can be used as an endpoint in clinical trials as a surrogate marker prognostic endpoint for T1D.
99. The method of embodiment 1, wherein the quantitative and/or qualitative analysis of amyloid-producing bacteria in microbiota and/or ages associated with amyloid-producing bacteria and/or HLA alleles are used for the diagnosis as biomarkers and can be used in for Mechanism of Action; Drug Target Selection; Stratification; Patient Selection; Enrichment; Dose Selection; Safety Assessment; Efficacy Assessment; Molecular Pathways Leading to Disease; Preclinical Safety Assessment; Mechanism of Action; Dose Selection.
100. The method of embodiment 1, wherein the prevention of T1D is by prevention of Enterobacteriales and/or E. coli prophages induction.
101. The method of embodiment 1, wherein the prevention of T1D is by prevention of Enterobacteriales and/or E. coli prophages induction is done by the prevention of the appearance of elevated levels of mitomycin-C, H202, streptonigrin, alcohols, alterations of the pH, Isopropyl β-D-1-thiogalactopyranoside, or Tod in the gut.
102. The method of embodiment 1, wherein the prevention of T1D is by prevention of Enterobacteriales and/or E. coli prophages induction is done by the prevention of the appearance of bacteria producing mitomycin-C, H202, streptonigrin, alcohols, alterations of pH and other SOS-induction stress inductors with a non-limiting example of bacteria belonging to Actinomycetales/Actinomycetaceae.

In various of the above aspects and embodiments, the evaluation of predisposable to seroconversion and T1D is done by the quantitative and/or qualitative analysis of bacteriophages of amyloid-producing bacteria in microbiota. In various of the above aspects and embodiments, the evaluation of predisposable to seroconversion and T1D is done by the quantitative and/or qualitative analysis of bacteriophages of amyloid-producing bacteria in microbiota and quantitative and/or qualitative analysis of amyloid-producing bacteria. In various of the above aspects and embodiments, the evaluation of predisposable to seroconversion and T1D is done by the quantitative and/or qualitative analysis of bacteriophages of amyloid-producing bacteria in microbiota and quantitative and/or qualitative analysis of bacteria. In various of the above aspects and embodiments, the evaluation of predisposable to seroconversion and T1D is done by the quantitative and/or qualitative analysis of bacteriophages of amyloid-producing bacteria in microbiota and quantitative and/or qualitative analysis of bacteria and/or HLA alleles. In various of the above aspects and embodiments, the evaluation of predisposable to seroconversion and T1D is done by the quantitative and/or qualitative analysis of bacteriophages of Enterobacteriales and/or E. coli. In various of the above aspects and embodiments, the evaluation of predisposable to seroconversion and T1D is done by the quantitative and/or qualitative analysis of bacteriophages of Enterobacteriales and/or E. coli and quantitative and/or qualitative analysis of Enterobacteriales and/or E. coli. In various of the above aspects and embodiments, the evaluation of predisposable to seroconversion and T1D is done by the quantitative and/or qualitative analysis of bacteriophages of Enterobacteriales and/or E. coli and quantitative and/or qualitative analysis of bacteria. In various of the above aspects and embodiments, the evaluation of predisposable to seroconversion and T1D is done by the quantitative and/or qualitative analysis of bacteriophages of Enterobacteriales and/or *E. coli* and quantitative and/or qualitative analysis of bacteria and/or HLA alleles. In various embodiments of methods of treatment described herein, the therapeutic agent is administered according to a dosage regimen. Each therapeutic agent may be administered daily, every two days, every three days, every four days, every five days, every week, every two weeks, every three weeks, and every month. Therapeutic agents may be administered together or separately. When multiple therapeutic agents are administered, each may be administered according to a separate dosage regimen. For example, one agent is administered daily and another administered weekly.

In some embodiments, the bacteria are added to drinking water and administered once to the mammal. In some embodiments, bacteria in drinking water is administered daily to the mammal, every two days to the mammal, every three days to the mammal, every four days to the mammal, every week to the mammal, every two weeks to the mammal, every three weeks to the mammal, or every four weeks to the mammal. In various embodiments, the bacteria are from Lactobacillales, e.g., *L. plantarum*. In various embodiments, the bacteria are from *Bifidobacterium*, e.g., *Bifidobacterium breve*. In various embodiments, the bacteria are *E. coli*, such as but not limited to, *E. coli* strain VT-58-mut and *E. coli* strain VT-55. In various embodiments, oral administration of n-Heptyl α-D-mannose or Doxycycline is undertaken after four days, after one week, after 10 days, after two weeks, or after three weeks from administration of the bacteria. In various embodiments, one or more of silicate of aluminum, a nuclease (e.g., DNAse I or T7 Endonuclease I), Larazotide, an antibody against amyloid protein, and transthyretin are administered to the mammal. In some embodiments, siRNA is administered to the mammal. The siRNA may be against CsgA or against CsgB. An siRNA against CsgA may be administered in combination with an siRNA against CsgB. In various embodiments, the siRNA is administered weekly, every 10 days, every two weeks, or every three weeks.

In various of the above aspects and embodiments, the quantitative and/or qualitative analysis of amyloid-producing bacteria in microbiota and/or agents associated with amyloid-producing bacteria and/or HLA alleles are used for the diagnosis and the presence of particular autoantibodies, with non-limiting examples of IAA, GADA, IA2A, ZNT8A or ICA used to determine patient population who will develop T1D or ketoacidosis.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Colonization with Amyloid-Producing Bacteria or the Administration of Bacterial Curli Leads to Seroconversion and T1D Development in Animal Model Or this experiment, bacterial amyloid and curli-DNA complexes were isolated and purified from wild-type, amyloid-producing *E. coli* strain VT-55 as follows. *E. coli* VT-55 overnight cultures were grown in LB with shaking (200 rpm) at 37° C. The overnight cultures were then diluted 1:100 in YESCA broth with 2% (v/v) DMSO to enhance curli formation [86], and grown in a water bath at 26° C. for 24 hours with shaking (200 rpm). Bacterial pellets were collected and resuspended in 10 mM Tris-HCl at pH 8.0 and treated with 0.1 mg/mL RNase A and 0.1 mg/mL DNase I (all from Sigma). 1 mM MgCl2 was added for 20 minutes at 37° C. Then, bacterial cells were broken by two sets of freezing and sonication (30% amplification for 30 seconds, repeated in triplicate). Lysozyme (1 mg/mL; Sigma) was added following incubation at 37° C. for 60 minutes. 1% SDS was added, and samples were incubated for 25 minutes at 37° C. with shaking (200 rpm). Then the fibers were pelleted by centrifugation at 10000 rpm for 10 minutes (Eppendorf). The supernatant was discharged, and the pellet was resuspended in 10 mL Tris-HCL, pH 8 with boiling for 10 minutes at 100° C. Digestion with RNase A, DNase I, and lysozyme was then performed, followed by boiling. Fibers were pelleted 10000 rpm for 10 minutes (Eppendorf), and boiled in 2×SDS-PAGE buffer and run on a 12% running stacking gel for 6 hours at 20 mA. The curli fibers that accumulated at the top of the gel were collected and washed three times with sterile water and then extracted by washing twice with 95% ethanol. The fibers were sonicated at 30% amplitude for 30 seconds to disrupt any large aggregates. The amount and concentration of the curli fibers was determined using BCA reagent according to the manufacturer's protocol (Novagen).

Obtained curli were then used in an animal study. In this experiment, 4-week-old non-obese diabetic (NOD/ShiLtJ) mice (Jackson Laboratory, Bar Harbor, Me., USA) were housed and bred under specific pathogen-free conditions. Mice were maintained in a temperature controlled (22±2° C.) animal facility with a 12 hour light/dark cycle. Mice were allowed free access to food and acidified drinking water.

Mice were injected i.p. with PBS (vehicle), or 25 µg or 50 µg isolated bacterial amyloid once a week. Acceleration of T1D development was accessed by measuring blood glucose in a manner consistent with diabetes monitoring, using a FreeStyle Lite meter and test strips (Abbott). Blood glucose was evaluated weekly via a tail vein. T1D development was defined as occurring after two consecutive blood glucose measurements of at least 250 mg/dL.

The groups tested were as follows:
Control group 1: received vehicle
Experimental group 25: 25 µg curli-DNA *E. coli* VT-55
Experimental group 50: 50 µg curli-DNA *E. coli* VT-55

Administration of bacterial amyloid-DNA complexes had a significant effect on T1D development, as shown in Table 1.

TABLE 1

| | T1D incidence | |
|---|---|---|
| | | T1D incidence (weeks) |
| Group | 20% | 50% |
| Control 1 | 16 | 24 |
| Experimental 25 | 12 | 16 |
| Experimental 50 | 10 | 14 |

The earliest time of disease onset was evaluated, as shown in Table 2.

TABLE 2

Earliest time of disease onset

| Group | T1D incidence (weeks) |
|---|---|
| Control 1 | 14 |
| Experimental 25 | 10 |
| Experimental 50 | 9 |

The data presented herein indicate that animals from the "Experimental group 25" and "Experimental group 50" had a higher incidence of T1D as compared to the control group. Bacterial curli-DNA complexes promoted T1D development in a dose dependent manner. Control groups demonstrated a T1D incidence approximating 20% by 16 weeks of age, with an incidence of 50% by 24 weeks of age.

Example 2: Colonization with Amyloid-Producing Bacteria Lead to Seroconversion and T1D Development in Animal Model For this study non-obese diabetic mice (NOD/ShiLtJ) 4 weeks old (females) (Jackson Laboratory, Bar Harbor, Me., USA) were housed and bred under specific pathogen-free conditions. Mice were maintained in a temperature controlled (22±2° C.) animal facility with a 12 hour light/dark cycle and were allowed free access to food and acidified drinking water. To increase the efficacy of E. coli transfer, all animals were exposed to antibiotic treatment before the transfer of E. coli starting at three weeks of age and the mice receiving bacteria were treated with ampicillin (1 g/L) in the drinking water for the next 4 weeks.

Bacterial Strains that were transferred include: E. coli strain VT-55—a wild-type, amyloid-producing strain.

E. coli strain VT-58-mut (mutant, not producing amyloid) had an unmarked deletion of csgBA, was used as a negative control.

E. coli VT-55 and E. coli VT-58-mut were administered with oropharyngeal gavage to 8 weeks old mice at $10^8$ CFU, 2 times a week. Acceleration of T1D development was accessed by measuring blood glucose in a manner consistent with diabetes monitoring, using a FreeStyle Lite meter and test strips (Abbott). Blood glucose was evaluated weekly via a tail vein. T1D development was defined as occurring after two consecutive blood glucose measurements of at least 250 mg/dL.

The groups tested were as follows:
Control group 1: received vehicle
Control group 2: E. coli VT-58-mut
Experimental group: E. coli VT-55

TABLE 1

T1D incidence

| Group | T1D incidence (weeks) | |
|---|---|---|
| | 20% | 50% |
| Control 1 | 16 | 24 |
| Control 2 | 15 | 26 |
| Experimental | 12 | 16 |

We also evaluated the earliest time of disease onset (Table 2).

TABLE 2

Earliest time of disease onset

| Group | T1D incidence (weeks) |
|---|---|
| Control 1 | 14 |
| Control 2 | 14 |
| Experimental | 10 |

The data demonstrate that colonization with amyloid-producing bacteria promote T1D development, while colonization with mutated non-amyloid-producing bacteria do not affect the disease state. Animals from the experimental group developed higher T1D compared to Control groups. Both Control 1 and Control 2 groups demonstrated a T1D incidence approximating 20% by 16 weeks of age, with an incidence of 50% by 24 weeks of age. Colonization of the gut with amyloid-producing E. coli had a significant effect on T1D development: 20% had T1D by 12 weeks of age, with an incidence of 50% by 16 weeks of age. Moreover, animals from the Experimental group had an earlier time of disease onset as compared to the Control groups.

Example 3: Effect of Different Factors to Prevent T1D Development in Animal Model Following Colonization with Amyloid-Producing Bacteria For this study non-obese diabetic mice (NOD/ShiLtJ) 8 weeks old (Jackson Laboratory, Bar Harbor, Me., USA) were housed and bred under specific pathogen-free conditions. Mice were maintained in a temperature controlled (22±2° C.) animal facility with a 12 hour light/dark cycle and were allowed free access to food and acidified drinking water. To increase the efficacy of E. coli transfer, all animals were exposed to antibiotic treatment before the transfer of E. coli. Starting at three weeks of age, recipient mice were treated with ampicillin (1 g/L) in the drinking water for the next 4 weeks. The bacterial strains used: E. coli strain VT-55—a wild-type, amyloid-producing strain. E. coli VT-55 bacteria were administered with oropharyngeal gavage to 8 week old female mice at $10^8$ CFU, 2 times a week. Acceleration of T1D development was accessed by measuring blood glucose in a manner consistent with diabetes monitoring, using a FreeStyle Lite meter and test strips (Abbott). Blood glucose was evaluated weekly via a tail vein. T1D development was defined as occurring after two consecutive blood glucose measurements of at least 250 mg/dL.

Details for the experiments are listed in Table 3, if not stated below.

Transthyretin

To obtain mouse Transthyretin (TTR), a cDNA mouse TTR clone was subcloned into pMMHa vector at the NdeI and KpnI restriction sites.

(>NC_000084.6: 20665250-20674326 *Mus musculus* strain C57BL/6J
chromosome 18.GRCm38.p4 C57BL/6J)

(SEQ ID NO: 1)

CTAATCTCCCTAGGCAAGGTTCATATTTGTGTAGGTTACTTATTCTCCTTTTGTTG

ACTAAGTCAATAATCAGAATCAGCAGGTTTGGAGTCAGCTTGGCAGGGATCAGC

AGCCTGGGTTGGAAGGAGGGGGTATAAAAGCCCCTTCACCAGGAGAAGCCGTCA

CACAGATCCACAAGCTCCTGACAGGATGGCTTCCCTTCGACTCTTCCTCCTTTGCC

TCGCTGGACTGGTATTTGTGTCTGAAGCTGGCCCCGCGGTGAGTGATCCTGTGAG

CGATCCAGACATGGCAGTTAGACCTTAGATAAAGAAGAAGTGCCTTCTTCCAGA

TGTGAGAACTAGAGTACTCAGACTCTATATTTACCATTAGACTCCAAAGAGAAG

AGCTGGAGTGCCTCTGGCTCTTCCTTCTATTGCTTTAGCGCATTGGGTCTGTAGTG

CTCAGTCTCTGGTGTCCTTAGATAATAAAGATATGAGATTAACATAGAAATAAAG

ATATAAAAGGGCTGGATGTATAGTTTAGTGGTCCAGTGTATGCCTAGTATGTGAA

AAGCCTTCTGTTCAACCTCTAGCAATAGAAAAACAAGATATATTCTCGGTGGGGC

TGTTAATATTGAATTCTCATAAAATCTTTAATATATTTAGTATGCCTATTATGTTG

TTATATTTTAGTTCTTTAGCTAATCAAATGCATTATTGATCTTTCTTTGTCTTTTT

TTGGCCAACACTCTATTCCAGTCTTTGAAAAAGTCCTTTAAAAGAGTTAATCAGT

ATAATTAAATGAGTCAGGAAGTATGTGAGGGTTATTTTACAACCAGAGGGAATT

ACTATAGCAACAGCTGATTAGAATGATCTCAAGAAAAAGCCCATTCTGTCTTTTT

GCACCATGCACCTTTCAGTGGCTCCATTCAGATGGAGAGGCAAACAGAGCAATG

GCTCTCAGAGGGCCTATTTTCCCTTTGAACATTCATTATCCATATCCCTGGTGCAC

AGCAGTGCATCTGGGGGCAGAAACTGTTCTTGCTTTGGAAACAATGCTGTCTATG

TCATACTGGATAAAGAAGCTCATTAATTGTCAACACTTATGTTATCATAATGGGA

TCAGCATGTACTTTTGGTTTTGTTCCAGAGTCTATCACCGGAAAGAACAAGCCGG

TTTACTCTGACCCATTTCACTGACATTTCTCTTGTCTCCTCTGTGCCCAGGGTGCT

GGAGAATCCAAATGTCCTCTGATGGTCAAAGTCCTGGATGCTGTCCGAGGCAGC

CCTGCTGTAGACGTGGCTGTAAAAGTGTTCAAAAAGACCTCTGAGGGATCCTGG

GAGCCCTTTGCCTCTGGGTAAGCTTGTAGAAAGCCCACCATGGGACCGGTTCCAG

GTTCCCATTTGCTCTTATTCGTGTTAGATTCAGACACACACAACTTACCAGCTAG

AGGGCTCAGAGAGAGGGCTCAGGGGCGAAGGGCACGTATTGCTCTTGTAAGAGA

CACAGGTTTAATTCCTAGCACCAGAATGGCAGCTCATAACCATCTGAAACTCACA

GTCTTAGGAGATCTGGGTATCTGACATTCTCTTCTACCCACCATGTGTGTGGTGC

ACAAATTCACATGCAGGCATCAAATCTTATAAACAACAACAAAAAACCAACAAA

CCTGGTAGCAAAAGAAGATTAGAAGGTTAAACATATGAGCCGAGAGCTTTTGTT

TTGTTTTGTTTTGTTTTGTTTACATTTCAAATGTTATCCCCTTTCTCGGTCCC

CCTCCCCAAACCCTCTACCCCATTCTCTCCTCCCCTTCTTCTATGAGGGTGTTCCC

CACCAACCCACTCCCACCTTCCTGCTCTCGAATTCCCCTATACTGGGACATCAAG

CCTTCACAGAATCAAGGGCCTCTCCTCCCATTGATGCCCGACAATGTCATCCTCT

GCTACCTATGTGGCTGGAGCCATGGGTCCCTTCATGTATCCTCCTTGGTTGGTGGT

TTAGTCTCTGGGAGGTCTGGGGGATCTGGTTGATTGATATTATTGTTCTTCCTATG

AGATTGCAAACCCCTTCAGCTCCTTCGGTCCTTTAACTCCTCCACTGGGGACCCC

GAGCTCAGTCCAATGGTTGGCTGTGAGCATCCACCAGCAGAGGCCTTTTTTTTTT

-continued

```
TTTTTAACAAAGCTGCTTTATTATGTTGCTTAGAGCATGACCAGGAACCAGAGCA

CAGTCCAAGACTGAAGGGAGGAAAAGGGGGGAGTCAATAACCCCACTGTTTCA

TAGTGGTTTGCAACCCTTTTATATCACAGCCCACTTTAGGCAAATAATGAAAATT

ATAGTCTCCAGGGACAGAGAAGATGGTGCAGGAAGTGAAGTGCCTGCTCAGAAA

ATGGGGGCTTGAATGTGAGTTCCCAGACTCTGTGTAAGATGCCCAGCATCGAAGT

GCATGCTTATAACACCAGCCTGGAGGTAGAAGCTTAGAAACAGGGGTACCCTGA

AGTTGCTTGTTCACCAGTGTCCCTGAATGGGTAGGTGCATGTTTGGTGAGAGACC

CTGTCTCAAAAATCAAGGTGTAGGATAATTGAAAATACCTAGCTTTGAGCTTAGA

TCATGCAAATGTGTACACACACTCACACACACCACACACACAAAAAAATGCAGA

GACAGAGAGATACAGAGAGACAGAGAGATACAGAGACAGAGACAGAGAGAAA

AGGAGAAAGTAAAAAACAAATAATTTAAAGACCCATGGCCACAAAGAGGCTCA

AAGACAAGCACGTATAAAACCATACACATGTAATTTTAGGAGTTTTCAGATTCCC

TGGTACCCGTGGGTGATGCACAAGCTTTGAATCCCAGTCTTAAAATCTTACGAAG

AACGTGTTCGTGTGTGCTAATTTATTGATGAGAGGAAAGGAATTGACAAAGTGCC

CTTCCGGAGCTTCCTGCATTACCCAGACTCAGGGTTTTTTTAAATGTACACTCAG

AACAGAGTAGCTCTGTGCAAGGGTAGCAACCACGAAGCTTAATAAGAAACATAT

CGTGAGAGATCTGCAAGGCAAATCTAGGGGCTGACCAATCTCACAGTCACCCAC

TAGCATGTCAACACAACTTCCCACCTGTGCTAGCCACTTAGCAATTTTGTGTTGTT

CTGTTTTGTTTTTGTTTTTAACAAAGCAATTTCAAAGAGATTTCTAATTCATCTAA

ACAAACAAACCAAAAGGAAAACAGCAAAGACGCCCTGAGCACTTAGCAGAGCA

GCTATGCAGTTATGACTCCTGGGTGGAGACTTTATATCAGGCTTCAACTGAATAC

CTAGAACCTACTAGTGCTCTTCATCAATCCTTGGGAAGGTCATTTTCTTTTGGTGC

TGTTTTGAGTTTCTATTTGTTAATGTCTTCATAATTATACACGTGTTGAGCACAGC

ATGCAAAGTGATTAGGGGAATCTAGTTGGAGTGGAATGGATACCCAAATATTCA

GACTTTCTTGTGACTCTTCTTTCTTGTACCCACATCAAAAAAAAAAAAAATGGAG

ATGAGACATGGTCAGAGTCACTAAAACCAGCTGCTACTTTTAATTACGTGGGGA

GCAGTTTCTAACATTGCCATTATTGAACTGATGCTGCCTGGGTGGAAATGGAAAT

CACTTAGTATTTCTTGTTGGCAAAGAATTACTGAATGGATTAAATTTCCAAAGGG

AGAAGTCAGTTACAAGTCTTTTCTTTGTTTATTAGGCTTTCTGCTATGATAAATTA

CACTACTTCCAGAAGTTACCCTTAGGCCATGGGACACTGGACTATCACTCTGCTG

TCACAAGAGATTACAGAGTTAGTCAAGGCAGCTTGTGACACCTTCAGGGACTGT

CATAAACTTCCAGCAAGTCATTAATCCTGAATGCAATACTGTGTGTGTGTCTA

TGTGTGTTTGTATGTCTGTGTGTGTCTTATGTCTGTGTCTCTGTGTGTGTGTGTT

TGTGTGTGTGTGTATGTATGCCTGTGTGTGTCTTATGTCTGTGTTTGTGTGTCT

GTGTGTGTCTTATGTCTGTGTTTGTATGTCTGTGTGTGTCTGTGTGTGTCTTATGTC

TGTGTCTCTGTGTGTGTGTGTGTATGTATGTATGTATGTATGTATGTGTATGTG

TTTGCATCTCTCTGTGTGTCTGCGCTTATATATTTGTGTATGTGTTTATGTGTTCGC

CTTTGTGCGTTGTTGGGGATTGAATCCAGGGGAATACAAATGTTAAGAAAGAAC

GTTACCACTAAGCTTCACCTGTAGGCCTTAAAGCTTTTCTTTCTTTTAAAAATTGT

AATTAATTCATTTTCAGTCAGGATCTCCACACCTCGTCCCTGCTGCTCTAGAACTC

ACTATTTAAACACAATCGCCCTCAAACCTGCAGCAACCCTCCCGCCTCTACCCTG
```

-continued

```
CGAGCACTAGAATAATAACAGGTGACCCCACACGCCTAGATTAAGACCTTTAAG

GTAAACATTTTACTATATTTTAGTCTCATAAGACAAGATGCTACAATAAAGCTGT

ACATAAAGTTCCCTCGAATTTCTTGCTATTTTAACTCAAACATAAGGATTTCCTCC

TTTTTGATTCAGGTAACAGAAAAAATACACAGGTACATACATGTACACACATGA

ACACACACGCATCACAACCACATATGCGCACGCTTGTGTGATCTATCATTTACCA

TGCCACTGAACTCTTCTTTCCCCATAAATTCCTCTGGACTTGTGTGCCCTCCAGGA

AGACCGCGGAGTCTGGAGAGCTGCACGGGCTCACCACAGATGAGAAGTTTGTAG

AAGGAGTGTACAGAGTAGAACTGGACACCAAATCGTACTGGAAGACACTTGGCA

TTTCCCCGTTCCATGAATTCGCGGATGTAAGTGGACACACCAAGTTGTTTGGATT

TTGTTTTTAGTCTCAGGAAATTCCCTTCGCTCTTGCTGTACGATGGGCATGAGTGG

AAAGTAGATTCCACAGCCAGAATCCACAGTGCTGGGAAAGCAAGCCTTCTGAAT

TTTTCTAAAACTCATTTAGCAACATGGCCTGAACCTGTTCACACTGCTTATGGTCA

GCTAACTATATTTATGTAAATATTCATTTCTCTGTTGAGGAAATGTTAGTATTTGC

TTTTGAGGCAACCTCCAGATACCATGGAGGGCATGTCATAGTCAAAGAGAGGGC

TCCCTATGGTATTTCTCTAAATTCTGGCATTTCCTTTATTCCAAAGCACATCTAGT

GTCCCCAGAAGTTTGGGTAGACAATTCTTGGCAACACAGAGAATTACAACATGTT

CAAAACCCAACAGCTTAATATCTAAATCATCAAGCAAACATCACATGGCAAAGG

GATTTCTGAATCAAAACTGTTTCATCCTTATGATCAACCTATGGAGGTCTAGCCT

CGACTTACACCCATTTTACCAATAAGCTAAGAGAAGCTAAGTTCCTCATCAAGGA

CACAAGGCTAGCATGTGTGAGCAAGTGACAGAGTTGCCCTCTATGTTGGTTAGTG

TGCCTTAGCCAGTGTCTCAGTAAGAAATGGAGCTAAATCAAAACCCAAGGCCAA

CAGCCAAAGGCACATGAGTAACCTTTGCTTGGCACTGGGCTCAGTTTCCCTGGCT

CCTCTCAGTCCTCAGTTCACAGAGGCAGCTGTCATGCAAATAGAATCCAAGCTTG

TTGGTCAGACCTGGAGATAACAAATTCCATCAAAAATAGCTCCTCATGTGACCTA

GTTTGCTGTCTGTTGCTATGATACACACCATGACCGAAAAGCAACCCTGGGGAGA

GAAGGGTTTATTTCATCTTACAGCTTACAGTTCACCATGGAGGAAAGCCAGGTGG

GAACCTGGAAGTGGAAATTGAAGCAGAGACCAGAAAGGAATGCTGTTTACTGGC

TGGCTTAGCTCCTTTTCTTATACAGCTTAGGTCTATGTGCCCAGGGGATGGTACTG

CCGAGCATAGGCTGAGCCCGCCTACATCAACCATTAGTCAAAAAAAGGTCCATA

GACTTGCCTACAGGCCAATCTCATGGAGGCAATACCCCAGTGGAGGGTCCCTCTT

CGCAGGTTACTCTAGTTTGTGTCAAGTTGACAAAACCTAACCACAAAGCACAAA

CAGGGTCTGCCCTTGTGGCTTAGCCATGGATGACACTCTCAGATGATGGTGTTAC

CAGACAAACCAGAGGGGCTCACCAAGAGTCTGCCACCTACCAAGGTAGTACTCT

ACTCCTCACTGGGCACCAACACCCATATTAGCTGGGCCAGTACAGGACCCTTGCT

GTTTCCTGCATGAATTGTCCATAGACCCTGGGTCTCAGCCTGCCGGGAGTACCTG

TAAGTAGTCGCCTCAAACACATTATTCCTGTTGGAAGACTTGTCTGATTCTCTTTT

AGAACTCAATCAACAAACGTTTTTATTTTGTTTTGGCTTTTTGGAGACAAGATCTC

TCATAGGCCAGCCTGACTTGAATGTAGCTGAGGATGACCTGTGCTGCTAATCTTC

TCGCCTCTTCCTCCCAAGTGGTAGGATAATAGGCATAAGACACCACAGCAGTTTT

ACTCCATACCAGGGCTCTGAACCCAGACTTTAAACACTCTATCAACTGATTCACA
```

-continued

```
TTCCCACCCCATCATTCAACAAACATTTGAAAAATAAAACCCTTCTGCCTTGAGC
ACTCTGCTAAATACAGCCTTTGAGTGCGGAGTATTTCCTCACAACCAGGGTCCAA
GATGACCCCATCATACATACCACGGAAAATTAGGAGATGTTTTTAGGTCTCTTTG
CTTGGGGTAATTTTTATGTGTGTGTACACAGCCCTGTGCGTGTGTGTGTGTGTG
TGTGTGTGTGTGTACAGGCACACACGTGTATGCATGTAGAGGCTACATAAAAAC
CTTAGGTGTCATTCTCAGGCACTCTGTTCACCCCTTCACACAGCCCGAACACACA
AAATTTGAGGCATTAGCCTGGAGCTCACCAGTTAGGCTAGACTGACTTGCCAGCA
GACCCCAGGCTGTCTCCATCTCCCCAGCTCTGGGATTACAAACTCTATCATACCA
GACATTTTTATACATATTCTGAGCATAAAATTCATGTCTTCAGGCTAACAAGTCA
AGAGCTTAAATGACTGAGCTCTCTTACGTGGTGGATTTTTTTAAAACTACATAA
TATCTTTTTTTTTTTTTCACTTCTGGGGAAGAAACAAATGAGCCTGAGTGACAAT
GCGACAGAAAAGAAATTTTGAGGAGTGTGTGTGTCTGTGTGTGTGGTGGCACAT
GCCTCTCATCTAATGCTAGAGGCTACAGTAGAATGCTCCTGAATTAGTGGCCAGC
CAAGGCCAAGGGCTAGGGTTGTAACTCAGTGGCAGAGGGCTTGCCTAGCATTCG
CAGGATTTGATCCATAGCGCTATAAATAATAATAAATAAATACAACAGTCTAAG
ATGATTCTCCCTTTCATTTATCTGGATGTTATTTTTGTGTTAGTTTTACTCTGTCAT
CCAATCATTGTTTGCCCTATATTTGGACATTTAAAAAAAATCTTTATTCCAAGTGT
GTTCAAAGCTGTATCCAAAACCTGTCCACCAAATGAGTCCAATGACATACATCTT
CTATATTACCATCTGTTCCAGATTTGGCTGACTCCCGGCACCTGGGCTGTTGCTGC
ACCCATGTCTCAGATAGTCTAGTGATTTGAGAAGTGACTAGTAATTGCAAAATCC
AGACTTTGTCCAGAAACTTCTATGAGCTCCAAAACTTTCATTTACATTTCTGCCAG
CCACAAACCGCTTGTGTTGTGGAGAGAACCCTGTGATGTCTTCCCACAGCATCTC
AGCCTTGTTTCTTCCCTTAAAATATTCATCTTTTCACATTAGAACATGCAAAGGGA
CAGTGGGAGCGAAACCCCTGGACTGGGACGCACGAAGCCTTCCTTTCTGGTCAG
GCTCTCACTGTAGAAACTTAGGCCGGTTTCAGCATGCAGTCTGCTGGAGAATGGC
TCCTGCCAACATTCCAGGTCTGGAAGTTTGTAGTGGAGTTGTTGATAACCACTGT
TCGCCACAGGTCTTTTGTT
TGTGGGTGTCAGTGTTTCTACTCTCCTGACTTTTATCTGAACCCAAGAAAGGGAA
CAATAGCCTTCAAGCTCTCTGTGACTCTGATCTGACCAGGGCCACCCACACTGCA
GAAGGAAACTTGCAAAGAGAGACCTGCAATTCTCTAAGAGCTCCACACAGCTCC
AAAGACTTAGGCAGCATATTTTAATCTAATTATTCGTCCCCCAACCCCACCCCAG
AGGACAGTTAGACAATAAAAGGAAGATTACCAGCTTAGCATCCTGTGAACACTT
TGTCTGCAGCTCCTACCTCTGGGCTCTGTTAGAACTAGCTGTCTCTCCTCTCTCCT
AGGTGGTTTTCACAGCCAACGACTCTGGCCATCGCCACTACACCATCGCAGCCCT
GCTCAGCCCATACTCCTACAGCACCACGGCTGTCGTCAGCAACCCCCAGAATTGA
GAGACTCAGCCCAGGAGGACCAGGATCTTGCCAAAGCAGTAGCATCCCATTTGT
ACCAAAACAGTGTTCTTGCTCTATAAACCGTGTTAGCAGCTCAGGAAGATGCCGT
GAAGCATTCTTATTAAACCACCTGCTATTTCATTCAAACTGTGTTTCTTTTTTATTT
CCTCATTTTTCTCCCCTGCTCCTAAAACCCAAAATCTTCTAAAGAATTCTAGAAG
GTATGCGATCAAACTTTTTAAAGAAAGAAAATACTTTTTGACTCATGGTTTAAAG
GCATCCTTTCCATCTTGGGGAGGTCATGGGTGCTCCTGGCAACTTGCTTGAGGAA
```

```
GATAGGTCAGAAAGCAGAGTGGACCAACCGTTCAATGTTTTACAAGCAAAACAT

ACACTAAGCATGGTCTGTAGCTATTAAAAGCACACAATCTGAAGGGCTGTAGAT

GCACAGTAGTGTTTTCCCAGAGCATGTTCAAAAGCCCTGGGTTCAATCACAATAC

TGAAAAGTAGGCCAAAAAACATTCTGAAAATGAAATATTTGGGTTTTTTTTATA

ACCTTTAGTGACTAAATAAAGACAAATCTAAGAGACTAA
```

TTR was expressed in E. coli VT-243. The TTR protein was precipitated from the supernatant of a 48 hour culture of E. coli VT-243 after centrifugation (12,000×g, 20 minutes 4° C.) of the lysed cells in the gradient 40-90% ammonium sulfate fraction (1.8-3.6 M). The precipitate that contained TTR was dialyzed overnight against 10 mM sodium phosphate buffer, pH 7.5, 100 mM KCl, 1 mM EDTA. The same volume of 200 mM sodium acetate buffer (pH 4.4, 100 mM KCl, 1 mM EDTA) was added to achieve a final pH of 4.5, and the mixture was then incubated for 18 hours at 37° C. Following centrifugation (45 min, 30,000×g, 4° C.), the supernatant was gel filtrated (Superdex 75) to elute phosphate buffer.

siRNA Against CsgA and CsgB

SiRNA were developed against CsgA and CsgB using an online tool (https://www.invivogen.com/simawizard/).

E. coli CsgA sequence (>NC_000913.3: 1104447-1104902 Escherichia coli str.)

(SEQ ID NO: 2)
```
ATGAAACTTTTAAAAGTAGCAGCAATTGCAGCAATCGTATTCTCCGGTAG

CGCTCTGGCAGGTGTTGTTCCTCAGTACGGCGGCGGCGGTAACCACGGTG

GTGGCGGTAATAATAGCGGCCCAAATTCTGAGCTGAACATTTACCAGTAC

GGTGGCGGTAACTCTGCACTTGCTCTGCAAACTGATGCCCGTAACTCTGA

CTTGACTATTACCCAGCATGGCGGCGGTAATGGTGCAGATGTTGGTCAGG

GCTCAGATGACAGCTCAATCGATCTGACCCAACGTGGCTTCGGTAACAGC

GCTACTCTTGATCAGTGGAACGGCAAAAATTCTGAAATGACGGTTAAACA

GTTCGGTGGTGGCAACGGTGCTGCAGTTGACCAGACTGCATCTAACTCCT

CCGTCAACGTGACTCAGGTTGGCTTTGGTAACAACGCGACCGCTCATCAG

TACTAAATGAAACTTTTAAAAGTAGCAGCAATTGCAGCAATCGTATTCTC

CGGTAGCGCTCTGGCAGGTGTTGTTCCTCAGTACGGCGGCGGCGGTAACC

ACGGTGGTGGCGGTAATAATAGCGGCCCAAATTCTGAGCTGAACATTTAC

CAGTACGGTGGCGGTAACTCTGCACTTGCTCTGCAAACTGATGCCCGTAA

CTCTGACTTGACTATTACCCAGCATGGCGGCGGTAATGGTGCAGATGTTG

GTCAGGGCTCAGATGACAGCTCAATCGATCTGACCCAACGTGGCTTCGGT

AACAGCGCTACTCTTGATCAGTGGAACGGCAAAAATTCTGAAATGACGGT

TAAACAGTTCGGTGGTGGCAACGGTGCTGCAGTTGACCAGACTGCATCTA

ACTCCTCCGTCAACGTGACTCAGGTTGGCTTTGGTAACAACGCGACCGCT

CATCAGTACTAA
```

| siRNA | | |
|---|---|---|
| Sequence | Start | GC % |
| GCCCAAATTCTGAGCTGAACA (SEQ ID NO: 3) | 119 | 47.62 |
| GCCCGTAACTCTGACTTGACT (SEQ ID NO: 4) | 187 | 52.38 |
| GTAACTCTGACTTGACTATTA (SEQ ID NO: 5) | 191 | 33.33 |
| GGCGGTAATGGTGCAGATGTT (SEQ ID NO: 6) | 223 | 52.38 |
| GCGCTACTCTTGATCAGTGGA (SEQ ID NO: 7) | 299 | 52.38 |
| GCGACCGCTCATCAGTACTAA (SEQ ID NO: 8) | 436 | 52.38 |

E. coli CsgB sequence (>NC_000913.3: 1103951-1104406 Escherichia coli)

(SEQ ID NO: 9)
```
ATGAAAAACAAATTGTTATTTATGATGTTAACAATACTGGGTGCGCCTGG

GATTGCAGCCGCAGCAGGTTATGATTTAGCTAATTCAGAATATAACTTCG

CGGTAAATGAATTGAGTAAGTCTTCATTTAATCAGGCAGCCATAATTGGT

CAAGCTGGGACTAATAATAGTGCTCAGTTACGGCAGGGAGGCTCAAAACT

GTTTGGCGGTTGTTGCGCAAAAGGTAGTAGCAACCGGGCAAAGATTGACC

AGACAGGAGATTATAACCTTGCATATATTGATCAGGCGGGCAGTGCCAAC

GATGCCAGTATTTCGCAAGGTGCTTATGGTAATACTGCGATGATTATCCA

GAAAGGTTCTGGTAATAAAGCAAATATTACACAGTATGGTACTCAAAAAA

CGGCAATTGTAGTGCAGAGACAGTCGCAAATGGCTATTCGCGTGACACAA

CGTTAA
```

| siRNA | | |
|---|---|---|
| Sequence | Start | GC % |
| GCAGCAGGTTATGATTTAGCT (SEQ ID NO: 10) | 61 | 42.86 |
| GGTCAAGCTGGGACTAATAAT (SEQ ID NO: 11) | 148 | 42.86 |
| GATTGACCAGACAGGAGATTA (SEQ ID NO: 12) | 243 | 42.86 |
| GTGCCAACGATGCCAGTATTT (SEQ ID NO: 13) | 293 | 47.62 |
| GGCAATTGTAGTGCAGAGACA (SEQ ID NO: 14) | 402 | 47.62 |

The sequence GATTGACCAGACAGGAGATTA (SEQ ID NO: 15) was used for siRNA.

To develop nanoparticles with siRNA, we used cholesterol, distearoyl-sn-glycerol-3-phosphocholine (DSPC) and PEG2000-DMG (all Sigma). Nanoparticles were prepared by dissolving the 306013 lipidoid, cholesterol, DSPC, and PEG2000-DMG with final molar ratio of 50:38.5:10:1.5 in a 90% ethanol enriched with 10% 10 nM sodium citrate. Particles were formed following vortexing of equal volumes of siRNA solution with the lipid solution and subsequent dilution in PBS. Mice were orally gavaged with nanoparticles loaded with siRNA at a dose of 5 mg/kg.

Vaccination Against Amyloid-Producing *E. coli*

The EcVac vaccine consisted of conjugates containing the O-antigens of serotypes 06 of *E. coli* VT-55. O-antigen surface polysaccharide was conjugated to detoxified *P. aeruginosa* exotoxin A carrier protein as described previously [Riddle M S, Kaminski R W, Di Paolo C, et al., Safety and immunogenicity of a candidate bioconjugate vaccine against *Shigella flexneri* 2a administered to healthy adults: a single-blind, randomized phase I study. Clin. Vaccine Immunol., 2016, 23: 908-17]. The suspension for iv administration was made in TBS, (pH 7.4; 25 mmol Tris, 137 mmol NaCl, 2.8 mmol KCl).

Antibodies to *E. coli* Amyloid

Balb/c mice were immunized (10 μg) intraperitoneally and boosted (1 μg) subcutaneously with the *E. coli* amyloid isolated as previously described. Splenocytes were removed under sterile conditions, washed and hybridized to murine plasmacytoma parent cell line SP2/OAg14 using 40% polyethylene glycol and a spleen cell to plasmacytoma cell ratio of 5:1. Cells were plated in 96-well microtiter (Sarstedt) plates at 100,000 cells/per well with DMEM supplemented with 10% fetal bovine serum. Following 48h, cells were supplemented with hypoxanthine (100 PM) containing medium. After three washes with PBS-1% BSA, the presence of specific antibody binding was detected by ELISA. Serotype specific wells were cloned. Pristine-primed BALB/c mice were IP injected with $1 \times 10^7$ hybridoma cells. Ascites fluid was collected 14 days later, centrifuged (5000 g, 20 min, Eppendorf) and stored at −80° C. before use. Ascites fluid was filtered with affi-Gel protein A column (BioRad Laboratories) and fractions with antibodies were dialyzed against PBS and filtered through a 0.2 μm filter (Milipore). Antibodies were concentrated by ammonium sulfate with subsequent dialysis against PBS.

The groups used in the experiments are listed in Table 3.

TABLE 3

Effect of different factors to prevent T1D development in animal model

| Group | T1D provoking agent | Therapeutic Agent | Concentration of the active compound |
|---|---|---|---|
| Negative control 1 | None | Vehicle with drinking water | N/A |
| Negative control 2 | None | PBS gavaged | N/A |
| Positive control group | *E. coli* VT-55 | None | N/A |
| Exmperimental group 1 | *E. coli* VT-55 | Lactobacillies + Bifidobacterium | Daily administrations of the bacteria in drinking water<br>*L. plantarum* - $5 \times 10^9$ cfu/day<br>*Bifidobacterium breve* - $5 \times 10^9$ cfu/day |
| Exmperimental group 2 | *E. coli* VT-55 | *E. coli* VT-55 + Lactobacillies + Bifidobacterium | One time a week administration of the bacteria in drinking water at week 8<br>*L. plantarum* - $2 \times 10^9$ cfu/day<br>*Bifidobacterium breve* - $2 \times 10^9$ cfu/day |
| Exmperimental group 3 | *E. coli* VT-55 | Lactobacillies + Bifidobacterium | One time administration of the bacteria in drinking water at week 8<br>*L. plantarum* - $5 \times 10^{10}$ cfu/day<br>*Bifidobacterium breve* - $5 \times 10^{10}$ cfu/day |
| Exmperimental group 4 | *E. coli* VT-55 | n-Heptyl α-D-mannose | Mice were treated orally 2 weeks after *E. coli* colonization with n-Heptyl α-D-mannose (in house modified from Sigma) at 50 mg/kg dose |
| Exmperimental group 5 | *E. coli* VT-55 | Doxycycline | Doxycycline (Sigma) - 3 mg/ml was added to the drinking water, supplemented with 4% sucrose to mask the bitter taste |
| Exmperimental group 6 | *E. coli* VT-55 | *E. coli* strain VT-58-mut | *E. coli* strain VT-58-mut - Non-amyloid-producing *E. coli* strain with deletion of csgBA, was added in drinking water and administered $5 \times 10^8$ cfu/day |
| Exmperimental group 7 | *E. coli* VT-55 | siRNA against CsgA | p/o 5 mg/kg, 1 time in 2 weeks |
| Exmperimental group 8 | *E. coli* VT-55 | siRNA against CsgB | p/o 5 mg/kg, 1 time in 2 weeks |
| Exmperimental group 9 | *E. coli* VT-55 | 8-cyclopropyl-7-(1-naphthylmethyl)-5-oxo-2,3,6,7-tetrahydro-5H-[1,3]thiazolo[3,2-a]pyridine-3-carboxylic acid | 8-cyclopropyl-7-(1-naphthylmethyl)-5-oxo-2,3,6,7-tetrahydro-5H-[1,3]thiazolo[3,2-a]pyridine-3-carboxylic acid (in house synthesis) was given to mice 1 week after the colonization with *E. coli* with gavage at the final concentration in the intestine up to 2.5 mM |
| Exmperimental group 10 | *E. coli* VT-55 | Silicate of aluminium | silicate of aluminium (Smecta, IPSEN) was administered 2 times a week 1000 mg/kg, with gavage |
| Exmperimental group 11 | *E. coli* VT-55 | Deoxiribonuclease I | Deoxyribonuclease I (Sigma) was administered 1 time a day, with drinking water at final concentration of 2000 Kunitz units/daily |
| Exmperimental group 12 | *E. coli* VT-55 | T7 Endonuclease I | T7 Endonuclease I (New England Biolabs) was administered 1 time a day, with drinking water at final concentration of 10000 units/daily |
| Exmperimental group 13 | *E. coli* VT-55 | Vaccination against *E. coli* | 2 mcl intramuscularly at week 8 |
| Exmperimental group 14 | *E. coli* VT-55 | Vaccination against *E. coli* | 50 mcl iv at week 8 |
| Exmperimental group 15 | *E. coli* VT-55 | Larazotide (Glycylglycyl-L-valyl-L-leucyl-L-valyl-L-glutaminyl-L-prolyl-glycine) | Larazotide - 250 μg/mouse × 14 days, PO |

TABLE 3-continued

Effect of different factors to prevent T1D development in animal model

| Group | T1D provoking agent | Therapeutic Agent | Concentration of the active compound |
|---|---|---|---|
| Exmperimental group 16 | E. coli VT-55 | Antibodies to E. coli amyloid | 50 mcl iv at weeks 8 and 10 |
| Exmperimental group 17 | E. coli VT-55 | Transthyretin | p.o. 10 μg/mouse, 1 time a week |

Results for the effect of different factors one the prevention of T1D triggered by bacterial amyloid represented in Table 4.

TABLE 4

T1D incidence

| Group | Therapeutic Agent | Median T1D incidence 50% (weeks) |
|---|---|---|
| Negative control 1 | Vehicle with drinking water | 24 |
| Negative control 2 | PBS gavaged | 26 |
| Positive control group | No | 16 |
| Experimental group 1 | Lactobacillus + Bifidobacterium | 22 |
| Experimental group 2 | Lactobacillus + Bifidobacterium (daily) | 23 |
| Experimental group 3 | Lactobacillus + Bifidobacterium (once a week) | 23 |
| Experimental group 4 | n-Heptyl α-D-mannose | 22 |
| Experimental group 5 | Doxycycline | 25 |
| Experimental group 6 | E. coli strain VT-58-mut | 22 |
| Experimental group 7 | siRNA against CsgA | 21 |
| Experimental group 8 | siRNA against CsgB | 24 |
| Experimental group 9 | 8-cyclopropyl-7-(1-naphthylmethyl)-5-oxo-2,3,6,7-tetrahydro-5H-[1,3]thiazolo[3,2-a]pyridine-3-carboxylic acid | 21 |
| Experimental group 10 | Silicate of aluminium | 20 |
| Experimental group 11 | Deoxiribonuclease I | 20 |
| Experimental group 12 | T7 Endonuclease I | 22 |
| Experimental group 13 | Vaccination against E. coli (2 mcl intramuscularly at week 8) | 24 |
| Experimental group 14 | Vaccination against E. coli (50 mcl iv at week 8) | 25 |
| Experimental group 15 | Larazotide (glycylglycyl-L-valyl-L-leucyl-L-valyl-L-glutaminyl-L-prolyl-glycine) | 24 |
| Experimental group 16 | Antibodies against amyloid | 20 |
| Experimental group 17 | Transthyretin | 24 |

The data demonstrate that proposed therapeutic methods can prevent triggering of T1D by amyloid-bacteria.

Example 4: Effect of Different Factors to Prevent T1D Development in Animal Model Before Colonization with Amyloid-Producing Bacteria For this study, 8 week old non-obese diabetic mice (NOD/ShiLtJ; Jackson Laboratory, Bar Harbor, Me., USA) were housed and bred under specific pathogen-free conditions. Mice were maintained in a temperature controlled (22±2° C.) animal facility with a 12 h light/dark cycle and were allowed free access to food and acidified drinking water. To increase the efficacy of E. coli transfer, all animals were exposed to antibiotic treatment before the transfer of E. coli. Starting at three weeks of age, recipient mice were treated with ampicillin (1 g/L) in the drinking water for the next 4 weeks.
Bacterial Strain:
E. coli strain VT-55 is a wild-type, amyloid-producing strain—was used for the colonization of mice following their exposure to different factors. E. coli VT-55 were administered with oropharyngeal gavage to 9 week old NOD mice at $10^8$ CFU, 2 times a week.

Acceleration of T1D development was accessed by measuring blood glucose in a manner consistent with diabetes monitoring, using a FreeStyle Lite meter and test strips (Abbott). Blood glucose was evaluated weekly via a tail vein. T1D development was defined as occurring after two consecutive blood glucose measurements of at least 250 mg/dL.

Details for the experiments are listed in Table 5 if not stated below. All compositions were administered to 8 weeks animals, 1 week prior to colonization with E. coli VT-55.

TABLE 5

Effect of different factors to prevent T1D development in animal model before colonization with amyloid-producing E. coli

| Group | Therapeutic agent | Concentration of the active compound |
|---|---|---|
| Negative control 1 | Vehicle with drinking water | N/A |
| Negative control 2 | PBS gavaged | N/A |
| Positive control group | E. coli VT-55 | N/A |
| Experimental group 1 | Lactobacillies + Bifidobacterium | Administrations of the bacteria in drinking water L. plantarum - $5 \times 10^9$ cfu/day - for 5 days Bifidobacterium breve - $5 \times 10^9$ cfu/day - for 5 days |
| Experimental group 2 | E. coli strain VT-58-mut | E. coli strain VT-58-mut - Non-amyloid-producing E. coli strain with deletion of csgBA, was added in drinking water and administered $5 \times 10^8$ cfu/day for 5 days |
| Experimental group 3 | E. coli strain VT-55-mut, was administered to animals at week 9, | E. coli strain VT-55-mut - Non-amyloid-producing E. coli strain with deletion of csgBA from the E. coli strain VT-55. Animals were colonized with E. coli strain VT-55 - at week 9, at week 10, E. coli were isolated from their intestine, and modified in order to obtain E. coli strain VT-55-mut. E. coli strain VT-55-mut, was administered starting from week 11, by once time gavage ($5 \times 10^9$ cfu) added in drinking water and administered $5 \times 10^8$ cfu/day for 5 days |
| Experimental group 4 | Vaccination against E. coli | 1 mcl intramuscularly at week 8 |

Results are presented in Table 6.

TABLE 6

| | | |
|---|---|---|
| | T1D incidence | |
| Group | Composition | Median T1D incidence 50% (weeks) |
| Negative control 1 | Vehicle with drinking water | 26 |
| Negative control 2 | PBS gavaged | 26 |
| Positive control group | E. coli VT-55 | 17 |
| Experimental group 1 | Lactobacillales + Bifidobacterium | 23 |
| Experimental group 2 | E. coli strain VT-58-mut | 25 |
| Experimental group 3 | E. coli strain VT-55-mut, was administered to animals at week 9, | 24 |
| Experimental group 4 | Vaccination against E. coli | 22 |

The data demonstrate that the use of listed agents allowed to prevent the triggering of T1D by amyloid-producing *E. coli* colonization.

Example 5: Amyloid-Producing Bacteria Community Composition in T1D and Seroconversion To explore the amyloid-producing bacteria and phagobiota community structure associated with T1D, shotgun metagenomics sequencing data of the faecal microbiome from 11 children who exhibited autoantibodies (seven who developed autoantibodies with no progression to T1D, i.e. the "seroconverter" cohort), and the other four who were seroconverted and developed T1D (the "T1D" cohort). Both groups were named "Case", and 8 non-seroconverted control individuals were used. The patients were all carrying HLA types associated with diabetes. Microbiome analysis was performed at different timepoints of life.

Samples of the microbiota from each patient were subjected to sequencing and processing. DNA sequencing data were generated by Illumina Hiseq2500 paired-end shotgun mediated sequencing, which was used with an average of ~2.5 Gb per sample. Short sequence reads were retrieved from NCBI SRA. Sequences were quality-filtered to remove adaptor contamination, low-quality reads with minimum quality score cut-off of 20, sequences with <45 nucleotides, and human DNA. In the analysis of bacteria, sequences were grouped into OTUs with a 97% threshold of pairwise identity (Edgar, R. et al., 2010).

All reads were assembled de novo in each SRA file. The assembled contigs were tested against MetaPhlAn, which operates by mapping sequence reads to a database of pre-defined Glade-specific marker genes, and a custom method (Segata, N. et al., 2012; Hao, Yuhan, 2017). The resulting counts were normalized for total marker gene length and outliers, yielding profiles of the presence/absence and abundance of marker genes, and clade-relative abundance (Franzosa, E. et al., 2014).

The QIIME pipeline was used for quality filtering of bacterial DNA sequences, chimera removal (by the USE-ARCH software), taxonomic assignment, and calculation of α-diversity, as previously described (Caporaso, J. et al., 2010; Cox, L. et al., 2014). Downstream data analysis and calculation of diversity metrics were performed in R3.3.2 using gggplot2 and phyloseq libraries; DESeq2 was used to calculate logarithm of fold change (Love, M. et al., 2014).

All fecal analysis at the first sampling date had *E. coli* in their feces (Table 6). The association of disappearance of *E. coli* and development of seroconversion and/or T1D is shown in Table 7.

TABLE 6

| | | | | |
|---|---|---|---|---|
| | | Escherichia coli | | |
| Patient # | Gender | Case | Age at collection | s_Escherichia_coli |
| T025418 | female | T1D | 264 | 8.7569 |
| T025418 | female | T1D | 399 | 0.933322 |
| T025418 | female | T1D | 477 | 1.00E-04 |
| T025418 | female | T1D | 527 | 0.0164514 |
| T025418 | female | T1D | 568 | 0.235165 |
| T025418 | female | T1D | 629 | 1.00E-04 |
| T025418 | female | T1D | 1025 | 1.00E-04 |
| E010937 | female | T1D | 237 | 8.04615 |
| E010937 | female | T1D | 385 | 0.735695 |
| E010937 | female | T1D | 509 | 1.73319 |
| E010937 | female | T1D | 630 | 0.13326 |
| E010937 | female | T1D | 661 | 0.187955 |
| E010937 | female | T1D | 692 | 0.234004 |
| E010937 | female | T1D | 938 | 1.54843 |
| E010937 | female | T1D | 964 | 0.0167001 |
| E010937 | female | T1D | 1027 | 1.00E-04 |
| E006574 | male | T1D | 237 | 10.7947 |
| E006574 | male | T1D | 366 | 7.77439 |
| E006574 | male | T1D | 430 | 0.0895765 |
| E006574 | male | T1D | 520 | 1.00E-04 |
| E006574 | male | T1D | 562 | 0.224528 |
| E006574 | male | T1D | 616 | 0.172295 |
| E006574 | male | T1D | 683 | 1.00E-04 |
| E006574 | male | T1D | 788 | 1.00E-04 |
| E006574 | male | T1D | 844 | 1.00E-04 |
| E006574 | male | T1D | 918 | 1.00E-04 |
| E006574 | male | T1D | 1049 | 1.00E-04 |
| E003251 | female | T1D | 208 | 2.59238 |
| E003251 | female | T1D | 249 | 0.0326451 |
| E003251 | female | T1D | 355 | 0.201526 |
| E003251 | female | T1D | 474 | 1.00E-04 |
| E003251 | female | T1D | 508 | 1.00E-04 |
| E003989 | male | Seroconverted | 208 | 15.9866 |
| E003989 | male | Seroconverted | 303 | 2.163 |
| E003989 | male | Seroconverted | 474 | 2.31428 |
| E003989 | male | Seroconverted | 531 | 0.199124 |
| E003989 | male | Seroconverted | 659 | 1.00E-04 |
| E003989 | male | Seroconverted | 750 | 0.103283 |
| E003989 | male | Seroconverted | 1028 | 1.00E-04 |
| E010629 | male | Seroconverted | 164 | 12.0551 |
| E010629 | male | Seroconverted | 389 | 6.34123 |
| E010629 | male | Seroconverted | 1089 | 1.00E-04 |
| E017751 | female | Seroconverted | 179 | 0.120901 |
| E017751 | female | Seroconverted | 333 | 3.97529 |
| E017751 | female | Seroconverted | 502 | 1.09591 |
| E017751 | female | Seroconverted | 692 | 0.562454 |
| E017751 | female | Seroconverted | 722 | 3 |
| E017751 | female | Seroconverted | 778 | 0.0795315 |
| E017751 | female | Seroconverted | 998 | 0.221782 |
| E018113 | female | Seroconverted | 337 | 71.3864 |
| E018113 | female | Seroconverted | 434 | 0.246012 |
| E018113 | female | Seroconverted | 527 | 0.0157109 |
| E018113 | female | Seroconverted | 558 | 0.397849 |
| E018113 | female | Seroconverted | 584 | 4.39699 |
| E018113 | female | Seroconverted | 687 | 0.0263899 |
| E018113 | female | Seroconverted | 747 | 0.0157704 |
| E018113 | female | Seroconverted | 804 | 0.308717 |
| E018113 | female | Seroconverted | 1053 | 0.0310126 |
| E022137 | male | Seroconverted | 281 | 2.65466 |
| E022137 | male | Seroconverted | 397 | 0.0716974 |
| E022137 | male | Seroconverted | 612 | 1.00E-04 |
| E022137 | male | Seroconverted | 767 | 0.0547559 |
| E022137 | male | Seroconverted | 899 | 8.64364 |
| E026079 | male | Seroconverted | 227 | 39.519 |
| E026079 | male | Seroconverted | 369 | 0.70791 |
| E026079 | male | Seroconverted | 582 | 0.0353732 |
| E026079 | male | Seroconverted | 760 | 1.00E-04 |
| T013815 | female | Seroconverted | 42 | 6.25095 |
| T013815 | female | Seroconverted | 155 | 77.8702 |

TABLE 6-continued

Escherichia coli

| Patient # | Gender | Case | Age at collection | s_Escherichia_coli |
|---|---|---|---|---|
| T013815 | female | Seroconverted | 421 | 31.41 |
| T013815 | female | Seroconverted | 481 | 2.11968 |
| T013815 | female | Seroconverted | 485 | 7.78579 |
| T013815 | female | Seroconverted | 587 | 0.0724579 |
| T013815 | female | Seroconverted | 643 | 0.0397456 |
| T013815 | female | Seroconverted | 727 | 0.123386 |
| E001463 | male | Control | 303 | 13.8675 |
| E001463 | male | Control | 457 | 18.4476 |
| E001463 | male | Control | 638 | 13.1991 |
| E001463 | male | Control | 853 | 6.13739 |
| E001463 | male | Control | 1062 | 24.7321 |
| E001463 | male | Control | 943 | 18.4143 |
| E006547 | male | Control | 369 | 1.90878 |
| E006547 | male | Control | 465 | 1.00E−04 |
| E006547 | male | Control | 600 | 1.00E−04 |
| E006547 | male | Control | 785 | 2.47628 |
| E006547 | male | Control | 1040 | 0.158538 |
| E006673 | female | Control | 207 | 0.929969 |
| E006673 | female | Control | 339 | 1.40756 |
| E006673 | female | Control | 431 | 0.702923 |
| E006673 | female | Control | 536 | 1.00E−04 |
| E006673 | female | Control | 705 | 1.09332 |
| E010590 | male | Control | 227 | 0.943272 |
| E010590 | male | Control | 322 | 0.0171365 |
| E010590 | male | Control | 423 | 1.00E−04 |
| E010590 | male | Control | 525 | 1.00E−04 |
| E010590 | male | Control | 576 | 0.174626 |
| E010590 | male | Control | 626 | 0.382715 |
| E010590 | male | Control | 709 | 1.62622 |
| E010590 | male | Control | 804 | 0.121178 |
| E010590 | male | Control | 919 | 0.0321958 |
| E010590 | male | Control | 1045 | 0.053525 |
| E018268 | female | Control | 352 | 0.843772 |
| E018268 | female | Control | 504 | 0.438027 |
| E018268 | female | Control | 606 | 0.413332 |
| E018268 | female | Control | 747 | 0.197308 |
| E018268 | female | Control | 910 | 0.468278 |
| E018268 | female | Control | 1017 | 1.00E−04 |
| E018268 | female | Control | 1233 | 3.89111 |
| E022852 | male | Control | 362 | 2.74176 |
| E022852 | male | Control | 518 | 1.35695 |
| E022852 | male | Control | 681 | 0.237769 |
| E022852 | male | Control | 973 | 0.210955 |
| T014292 | female | Control | 249 | 7.95871 |
| T014292 | female | Control | 310 | 2.43492 |
| T014292 | female | Control | 471 | 2.46097 |
| T014292 | female | Control | 562 | 6.17588 |
| T014292 | female | Control | 652 | 0.13233 |
| T014292 | female | Control | 736 | 0.174175 |
| E016924 | female | Control | 164 | 0.167034 |
| E016924 | female | Control | 505 | 1.04181 |
| E016924 | female | Control | 769 | 2.71096 |
| E016924 | female | Control | 911 | 0.6683 |
| E016924 | female | Control | 1131 | 4.38507 |

TABLE 7

Association of disappearance of E. coli and development of seroconversion and/or T1D

| Patient # | Case | Presence or Disappearance of E. coli | Age at which E. coli disappears (if happens so) (days)* | Age of seroconversion (days) | Age of T1D (days) | HLA allele | Presence of E. coli |
|---|---|---|---|---|---|---|---|
| T025418 | T1D | disappearance | 477 | 540 | 880 | DQA1*05/*03-DQB1*02/*0302-DRB1*0401 | disappearance |
| E010937 | T1D | disappearance | 964 | 905 | 960 | DQB1*0302/*0501-DRB1*0401 | disappearance |
| E006574 | T1D | disappearance | 520 | 533 | 1340 | DQB1*0302/*0501-DRB1*0401 | disappearance |
| E003251 | T1D | disappearance | 249 | 358 | 1168 | DQA1*0201/*03-DQB1*02/*0302-DRB1*0404 | disappearance |
| E003989 | seroconverter | presence | 659 | 347 | N/A | DQB1*0302/*04-DRB1*0401 | presence |
| E010629 | seroconverter | disappearance* | 1089 | 945 | N/A | DQB1*0302/*0501-DRB1*0401 | disappearance* |
| E017751 | Seroconverter | presence | N/A | 175 | N/A | DQA1*05-DQB1*02/*0604 | presence |
| E018113 | seroconverter | presence | 434 | 588 | N/A | DQB1*0302/*04-DRB1*0401 | disappearance |
| E022137 | seroconverter | disappearance* | 612 | 562 | N/A | DQB1*0302/*0501-DRB1*0401 | disappearance* |
| E026079 | seroconverter | disappearance* | 582 | 580 | N/A | DQB1*0302/*04-DRB1*0401* | disappearance* |
| T013815 | seroconverter | presence | 587 | 350 | N/A | DQA1*05/*0201-DQB1*02/*02 IAA, | presence |
| E001463 | control | presence | N/A | N/A | N/A | DQB1*0302/*04-DRB1*0401 | presence |
| E006547 | control | presence | N/A | N/A | N/A | DQB1*0302/*0501-DRB1*0404 | presence |

TABLE 7-continued

Association of disappearance of E. coli and development of seroconversion and/or T1D

| Patient # | Case | Presence or Disappearance of E. coli | Age at which E. coli disappears (if happens so) (days)* | Age of seroconversion (days) | Age of T1D (days) | HLA allele | Presence of E. coli |
|---|---|---|---|---|---|---|---|
| E006673 | control | presence | N/A | N/A | N/A | DQA1*05/*03-DQB1*02/*0302-DRB1*0401 | presence |
| E010590 | control | presence | N/A | N/A | N/A | DQB1*0302/*04-DRB1*0401 | presence |
| E018268 | control | presence | N/A | N/A | N/A | DQB1*0302/*06 04-DRB1*0404 | presence |
| E022852 | control | presence | N/A | N/A | N/A | DQB1*0302/*05 01-DRB1*0404 | presence |
| T014292 | control | presence | N/A | N/A | N/A | DQA1*05/*03-DQB1*02/*0301 | presence |
| E016924 | control | presence | N/A | N/A | N/A | DQA1*05-DQB1*02/*04 | presence |

*Age at which E. coli disappeared means the day when in case groups for the first time E. coli abundance declined by ≥2 log compared with previous maximum abundance in this patient and reflects eradication (complete disappearance) or presumable eradication.

TABLE 8

Association of E. coli presence and disappearance with seroconversion

| Sample ID | T1D status | Age at collection | Number of Serum Autoantibodies | Escherichia coli presence/ disappearance |
|---|---|---|---|---|
| T025418 | T1D | 264 | 0 | Presence |
| T025418 | T1D | 399 | 0 | Presence |
| T025418 | T1D | 477 | 0 | Disappearance |
| T025418 | T1D | 527 | 1 | Disappearance |
| T025418 | T1D | 568 | 1 | Disappearance |
| T025418 | T1D | 629 | 1 | Disappearance |
| T025418 | T1D | 1025 | 3 | Disappearance |
| E010937 | T1D | 237 | 0 | Presence |
| E010937 | T1D | 385 | 0 | Presence |
| E010937 | T1D | 509 | 0 | Presence |
| E010937 | T1D | 630 | 0 | Presence |
| E010937 | T1D | 661 | 0 | Presence |
| E010937 | T1D | 692 | 0 | Presence |
| E010937 | T1D | 938 | 4 | Presence |
| E010937 | T1D | 964 | 4 | Disappearance |
| E010937 | T1D | 1027 | 4 | Disappearance |
| E006574 | T1D | 237 | 0 | Presence |
| E006574 | T1D | 366 | 0 | Presence |
| E006574 | T1D | 430 | 0 | Presence |
| E006574 | T1D | 520 | 0 | Disappearance |
| E006574 | T1D | 562 | 2 | Disappearance |
| E006574 | T1D | 616 | 2 | Disappearance |
| E006574 | T1D | 683 | 2 | Disappearance |
| E006574 | T1D | 788 | 2 | Disappearance |
| E006574 | T1D | 844 | 2 | Disappearance |
| E006574 | T1D | 918 | 2 | Disappearance |
| E006574 | T1D | 1049 | 5 | Disappearance |
| E003251 | T1D | 208 | 0 | Presence |
| E003251 | T1D | 249 | 0 | Disappearance |
| E003251 | T1D | 355 | 0 | Disappearance |
| E003251 | T1D | 474 | 2 | Disappearance |
| E003251 | T1D | 508 | 2 | Disappearance |
| E003989 | Seroconverted | 208 | 0 | Presence |
| E003989 | Seroconverted | 303 | 0 | Presence |
| E003989 | Seroconverted | 474 | 1 | Presence |
| E003989 | Seroconverted | 531 | 1 | Presence |
| E003989 | Seroconverted | 659 | 2 | Disappearance |
| E003989 | Seroconverted | 750 | 2 | Disappearance |
| E003989 | Seroconverted | 1028 | 2 | Disappearance |
| E010629* | Seroconverted | 164 | 0 | Presence |
| E010629 | Seroconverted | 389 | 0 | Presence |
| E010629 | Seroconverted | 1089 | 4 | Disappearance |
| E017751 | Seroconverted | 179 | 0 | Presence |
| E017751 | Seroconverted | 333 | 1 | Presence |
| E017751 | Seroconverted | 502 | 1 | Presence |
| E017751 | Seroconverted | 692 | 1 | Presence |
| E017751 | Seroconverted | 722 | 1 | Presence |
| E017751 | Seroconverted | 778 | 2 | Presence |
| E017751 | Seroconverted | 998 | 2 | Presence |
| E018113 | Seroconverted | 337 | 0 | Presence |
| E018113 | Seroconverted | 434 | 0 | Disappearance |
| E018113 | Seroconverted | 527 | 0 | Disappearance |
| E018113 | Seroconverted | 558 | 0 | Disappearance |
| E018113 | Seroconverted | 584 | 3 | Disappearance |
| E018113 | Seroconverted | 687 | 3 | Disappearance |
| E018113 | Seroconverted | 747 | 3 | Disappearance |
| E018113 | Seroconverted | 804 | 5 | Disappearance |
| E018113 | Seroconverted | 1053 | 5 | Disappearance |
| E022137* | Seroconverted | 281 | 0 | Presence |
| E022137 | Seroconverted | 397 | 0 | Presence |
| E022137 | Seroconverted | 612 | 1 | Disappearance |
| E022137 | Seroconverted | 767 | 2 | Disappearance |
| E022137 | Seroconverted | 899 | 2 | Disappearance |
| E026079* | Seroconverted | 227 | 0 | Presence |
| E026079 | Seroconverted | 369 | 0 | Disappearance |
| E026079 | Seroconverted | 582 | 3 | Disappearance |
| E026079 | Seroconverted | 760 | 3 | Disappearance |
| T013815 | Seroconverted | 42 | 0 | Presence |
| T013815 | Seroconverted | 155 | 0 | Presence |
| T013815 | Seroconverted | 421 | 2 | Presence |
| T013815 | Seroconverted | 481 | 2 | Presence |
| T013815 | Seroconverted | 485 | 2 | Presence |
| T013815 | Seroconverted | 587 | 1 | Disappearance |
| T013815 | Seroconverted | 643 | 2 | Disappearance |
| T013815 | Seroconverted | 727 | 1 | Disappearance |
| E001463 | Control | 303 | 0 | Presence |
| E001463 | Control | 457 | 0 | Presence |
| E001463 | Control | 638 | 0 | Presence |
| E001463 | Control | 853 | 0 | Presence |
| E001463 | Control | 943 | 0 | Presence |
| E001463 | Control | 1062 | 0 | Presence |
| E006547 | Control | 369 | 0 | Presence |
| E006547 | Control | 465 | 0 | Disappearance |
| E006547 | Control | 600 | 0 | Disappearance |

TABLE 8-continued

Association of E. coli presence and disappearance with seroconversion

| Sample ID | T1D status | Age at collection | Number of Serum Autoantibodies | Escherichia coli presence/ disappearance |
|---|---|---|---|---|
| E006547 | Control | 785 | 0 | Presence |
| E006547 | Control | 1040 | 0 | Presence |
| E006673 | Control | 207 | 0 | Presence |
| E006673 | Control | 339 | 0 | Presence |
| E006673 | Control | 431 | 0 | Presence |
| E006673 | Control | 536 | 0 | Disappearance |
| E006673 | Control | 705 | 0 | Presence |
| E010590 | Control | 227 | 0 | Presence |
| E010590 | Control | 322 | 0 | Presence |
| E010590 | Control | 423 | 0 | Presence |
| E010590 | Control | 525 | 0 | Presence |
| E010590 | Control | 576 | 0 | Presence |
| E010590 | Control | 626 | 0 | Presence |
| E010590 | Control | 709 | 0 | Presence |
| E010590 | Control | 804 | 0 | Presence |
| E010590 | Control | 919 | 0 | Presence |
| E010590 | Control | 1045 | 0 | Presence |
| E018268 | Control | 352 | 0 | Presence |
| E018268 | Control | 504 | 0 | Presence |
| E018268 | Control | 606 | 0 | Presence |
| E018268 | Control | 747 | 0 | Presence |
| E018268 | Control | 910 | 0 | Presence |
| E018268 | Control | 1017 | 0 | Disappearance |
| E018268 | Control | 1233 | 0 | Presence |
| E022852 | Control | 362 | 0 | Presence |
| E022852 | Control | 518 | 0 | Presence |
| E022852 | Control | 681 | 0 | Presence |
| E022852 | Control | 973 | 0 | Presence |
| T014292 | Control | 249 | 0 | Presence |
| T014292 | Control | 310 | 0 | Presence |
| T014292 | Control | 471 | 0 | Presence |
| T014292 | Control | 562 | 0 | Presence |
| T014292 | Control | 652 | 0 | Presence |
| T014292 | Control | 736 | 0 | Presence |
| E016924 | Control | 164 | 0 | Presence |
| E016924 | Control | 290 | 0 | Presence |
| E016924 | Control | 505 | 0 | Presence |
| E016924 | Control | 769 | 0 | Presence |
| E016924 | Control | 911 | 0 | Presence |
| E016924 | Control | 1131 | 0 | Presence |

The data demonstrate correlations between the depletion of E. coli and seroconversion. A positive correlation was detected between the appearance of autoantibodies and eradication of E. coli in T1D group, and majority of seroconverters; but no such a correlation was detected in control group. Three of four T1D patients displayed an eradication (or an episode of eradication) of E. coli prior to the detection of autoantibodies. Moreover, all patients within this group had an eradication of E. coli prior to the diabetes diagnosis. Data received suggest that the alterations of amyloid-producing bacteria abundance in T1D group that happened before seroconversion was a signature associated with diseases able to distinguish T1D disease state. The observed alterations in intestinal E. coli population might lead to the release of curli fibers and DNA-amyloid complexes that act as a pro-diabetic factor triggering the seroconversion.

Example 6: Role of Bacteriophages in the Depletion of Amyloid-Producing Bacteria Community in T1D and Seroconversion The same fecal material was used from the patients listed in Example 5. Samples of the microbiota from each patient were subjected to sequencing and processing. DNA sequencing data were generated by Illumina Hiseq2500 paired-end shotgun sequencing with an average of ~2.5 Gb per sample. Sequences were quality-filtered to remove adaptor contamination and low-quality reads by using a minimum quality score cut-off of 20, sequences with <45 nucleotides, and human DNA. In the analysis of bacteria, sequences were grouped into OTUs with a 97% threshold of pairwise identity (Edgar, R. et al., 2010). The following phages were identified across studied population.

TABLE 9

List of Bacteriophages with non-zero Signaling Values

| | |
|---|---|
| Escherichia Stx1-converting recombinant phage HUN/2013 | Escherichia phage N15 |
| Escherichia phage Pollock | Escherichia phage T, |
| Escherichia phage phi191 | Escherichia phage D108, |
| Escherichia phage TL-2011b | Escherichia phage K1H, |
| Escherichia phage TL-2011c | Escherichia phage K1ind1 |
| Escherichia phage HK639 | Escherichia phage K1ind2 |
| Escherichia phage HK75 | Escherichia phage K1ind3 |
| Escherichia phage TL-2011b | Escherichia phage TL-2011c |
| Escherichia phage D108 | Escherichia phage K1G |
| Escherichia phage K1H | Escherichia phage K1ind1 |
| Escherichia phage K1ind2 | Escherichia phage K1ind3 |
| Escherichia phage EC6 | Escherichia phage 1720a-02 |
| Enterobacteria phage cdtI | Enterobacteria phage P2 |
| Enterobacteria phage HK97 | Enterobacteria phage Mu |
| Enterobacteria phage 933W | Enterobacteria phage P7 |
| Enterobacteria phage VT2-Sakai proviral | Enterobacteria phage AR1 |
| Enterobacteria phage phiP27 | Enterobacteria phage BP-4795 |
| Enterobacteria phage RB10 | Enterobacteria phage P88 |
| Enterobacteria phage JenP1 | Enterobacteria phage 9g |
| Enterobacteria phage P2 | Enterobacteria phage mEpX1 |
| Enterobacteria phage mEp460 | Enterobacterial phage mEp390 |
| Enterobacteria phage mEp237 | Enterobacteria phage mEp235 |
| Enterobacterial phage mEp234 | Enterobacteria phage HK225 |
| Enterobacterial phage mEp213 | Enterobacteria phage HK446 |
| Enterobacteria phage mEp043 c-1 | Enterobacteria phage HK542 |
| Enterobacteria phage HK106 | Enterobacteria phage HK544, |
| Enterobacteria phage HK630 | Enterobacteria phage HK633 |
| Enterobacteria phage mEpX2 | Enterobacteria phage IME10 |
| Enterobacteria phage lambda | Enterobacteria phage 2851 |
| Enterobacteria phage YYZ-2008 | Enterobacteria phage DE3 |
| Enterobacteria phage phi80 | Bacteriophage P4 |
| Bacteriophage 186 | Bacteriophage If1 |
| Stx2-converting phage 86 | Stx2 converting phage I |
| Stx2 converting phage II | Stx2-converting phage 1717 |
| Stx2 converting phage vB_EcoP 24B | |

Association between E. coli bacteriophages abundance and the depletion of E. coli is presented in Table 10.

TABLE 10

Association of E. coli phages with the disappearance of E. coli in studied population.

| Patient # | Phenotype | Age at collection | Escherichia coli | Phages sum |
|---|---|---|---|---|
| T025418 | T1D | 264 | 8.7569 | 357.6545 |
| T025418 | T1D | 399 | 0.933322 | 64.9898 |
| T025418 | T1D | 477 | 1.00E−04 | 0 |
| T025418 | T1D | 527 | 0.0164514 | 0 |
| T025418 | T1D | 568 | 0.235165 | 10.0395 |
| T025418 | T1D | 629 | 1.00E−04 | 0 |
| T025418 | T1D | 1025 | 1.00E−04 | 0 |
| E010937 | T1D | 237 | 8.04615 | 158.0469 |
| E010937 | T1D | 385 | 0.735695 | 38.0832 |
| E010937 | T1D | 509 | 1.73319 | 63.6175 |
| E010937 | T1D | 630 | 0.13326 | 3.8409 |
| E010937 | T1D | 661 | 0.187955 | 9.0267 |
| E010937 | T1D | 692 | 0.234004 | 7.2974 |
| E010937 | T1D | 938 | 1.54843 | 65.4289 |
| E010937 | T1D | 964 | 0.0167001 | 0 |
| E010937 | T1D | 1027 | 1.00E−04 | 0 |
| E006574 | T1D | 237 | 10.7947 | 147.5383 |
| E006574 | T1D | 366 | 7.77439 | 82.5151 |
| E006574 | T1D | 430 | 0.0895765 | 106.4728 |

TABLE 10-continued

Association of *E. coli* phages with the disappearance of *E. coli* in studied population.

| Patient # | Phenotype | Age at collection | *Escherichia coli* | Phages sum |
|---|---|---|---|---|
| E006574 | T1D | 520 | 1.00E−04 | 1.7191 |
| E006574 | T1D | 562 | 0.224528 | 17.4468 |
| E006574 | T1D | 616 | 0.172295 | 5.6679 |
| E006574 | T1D | 683 | 1.00E−04 | 0 |
| E006574 | T1D | 788 | 1.00E−04 | 0 |
| E006574 | T1D | 844 | 1.00E−04 | 0 |
| E006574 | T1D | 918 | 1.00E−04 | 0 |
| E006574 | T1D | 1049 | 1.00E−04 | 0 |
| E003251 | T1D | 208 | 2.59238 | 125.5202 |
| E003251 | T1D | 249 | 0.0326451 | 4.3547 |
| E003251 | T1D | 355 | 0.201526 | 21.8077 |
| E003251 | T1D | 474 | 1.00E−04 | 0 |
| E003251 | T1D | 508 | 1.00E−04 | 0 |
| E003989 | Seroconverted | 208 | 15.9866 | 189.9389 |
| E003989 | Seroconverted | 303 | 2.163 | 200.3695 |
| E003989 | Seroconverted | 474 | 2.31428 | 78.5426 |
| E003989 | Seroconverted | 531 | 0.199124 | 43.0176 |
| E003989 | Seroconverted | 659 | 1.00E−04 | 7.4868 |
| E003989 | Seroconverted | 750 | 0.103283 | 9.1552 |
| E003989 | Seroconverted | 1028 | 1.00E−04 | 6.4364 |
| E010629 | Seroconverted | 164 | 12.0551 | 68.8856 |
| E010629 | Seroconverted | 389 | 6.34123 | 83.3344 |
| E010629 | Seroconverted | 1089 | 1.00E−04 | 0 |
| E017751 | Seroconverted | 179 | 0.120901 | 12.527 |
| E017751 | Seroconverted | 333 | 3.97529 | 100.7157 |
| E017751 | Seroconverted | 502 | 1.09591 | 44.4256 |
| E017751 | Seroconverted | 692 | 0.562454 | 20.6353 |
| E017751 | Seroconverted | 722 | 3 | 143.9888 |
| E017751 | Seroconverted | 778 | 0.0795315 | 6.5562 |
| E017751 | Seroconverted | 998 | 0.221782 | 11.6884 |
| E018113 | Seroconverted | 337 | 71.3864 | 827.8967 |
| E018113 | Seroconverted | 434 | 0.246012 | 13.5068 |
| E018113 | Seroconverted | 527 | 0.0157109 | 0 |
| E018113 | Seroconverted | 558 | 0.397849 | 15.1289 |
| E018113 | Seroconverted | 584 | 4.39699 | 98.5375 |
| E018113 | Seroconverted | 687 | 0.0263899 | 1.5781 |
| E018113 | Seroconverted | 747 | 0.0157704 | 1.572 |
| E018113 | Seroconverted | 804 | 0.308717 | 16.2798 |
| E018113 | NA | 1053 | 0.0310126 | 1.8198 |
| E022137 | Seroconverted | 281 | 2.65466 | 134.5099 |
| E022137 | Seroconverted | 397 | 0.0716974 | 3.044 |
| E022137 | Seroconverted | 612 | 1.00E−04 | 1.2367 |
| E022137 | Seroconverted | 767 | 0.0547559 | 0 |
| E022137 | Seroconverted | 899 | 8.64364 | 97.1654 |
| E026079 | Seroconverted | 227 | 39.519 | 416.3901 |
| E026079 | Seroconverted | 369 | 0.70791 | 29.592 |
| E026079 | Seroconverted | 582 | 0.0353732 | 0 |
| E026079 | Seroconverted | 760 | 1.00E−04 | 0 |
| T013815 | Seroconverted | 42 | 6.25095 | 96.0234 |
| T013815 | Seroconverted | 155 | 77.8702 | 652.3165 |
| T013815 | Seroconverted | 421 | 31.41 | 2674.2485 |
| T013815 | Seroconverted | 481 | 2.11968 | 129.1526 |
| T013815 | Seroconverted | 485 | 7.78579 | 57.7222 |
| T013815 | Seroconverted | 587 | 0.0724579 | 1.6764 |
| T013815 | Seroconverted | 643 | 0.0397456 | 1.371 |
| T013815 | Seroconverted | 727 | 0.123386 | 9.4891 |
| E001463 | Control | 303 | 13.8675 | 129.9089 |
| E001463 | Control | 457 | 18.4476 | 158.1158 |
| E001463 | Control | 638 | 13.1991 | 168.7815 |
| E001463 | Control | 853 | 6.13739 | 144.7664 |
| E001463 | Control | 1062 | 24.7321 | 237.5444 |
| E001463 | Control | 943 | 18.4143 | 228.9923 |
| E006547 | Control | 369 | 1.90878 | 65.0304 |
| E006547 | Control | 465 | 1.00E−04 | 69.8786 |
| E006547 | Control | 600 | 1.00E−04 | 62.4282 |
| E006547 | Control | 785 | 2.47628 | 128.6199 |
| E006547 | Control | 1040 | 0.158538 | 9.7865 |
| E006673 | Control | 207 | 0.929969 | 112.9593 |
| E006673 | Control | 339 | 1.40756 | 50.4738 |
| E006673 | Control | 431 | 0.702923 | 30.8944 |
| E006673 | Control | 536 | 1.00E−04 | 11.1907 |
| E006673 | Control | 705 | 1.09332 | 65.3403 |
| E010590 | Control | 227 | 0.943272 | 21.3611 |
| E010590 | Control | 322 | 0.0171365 | 0 |
| E010590 | Control | 423 | 1.00E−04 | 0 |
| E010590 | Control | 525 | 1.00E−04 | 0 |
| E010590 | Control | 576 | 0.174626 | 8.0515 |
| E010590 | Control | 626 | 0.382715 | 20.5393 |
| E010590 | Control | 709 | 1.62622 | 60.1574 |
| E010590 | Control | 804 | 0.121178 | 8.8609 |
| E010590 | Control | 919 | 0.0321958 | 9.8915 |
| E010590 | Control | 1045 | 0.053525 | 3.3678 |
| E018268 | Control | 352 | 0.843772 | 22.6724 |
| E018268 | Control | 504 | 0.438027 | 15.8211 |
| E018268 | Control | 606 | 0.413332 | 23.4269 |
| E018268 | Control | 747 | 0.197308 | 6.3116 |
| E018268 | Control | 910 | 0.468278 | 24.6769 |
| E018268 | Control | 1017 | 1.00E−04 | 1.8704 |
| E018268 | Control | 1233 | 3.89111 | 147.8895 |
| E022852 | Control | 362 | 2.74176 | 117.4477 |
| E022852 | Control | 518 | 1.35695 | 77.973 |
| E022852 | Control | 681 | 0.237769 | 24.0465 |
| E022852 | Control | 973 | 0.210955 | 3.7993 |
| T014292 | Control | 249 | 7.95871 | 174.9478 |
| T014292 | Control | 310 | 2.43492 | 109.5884 |
| T014292 | Control | 471 | 2.46097 | 56.8019 |
| T014292 | Control | 562 | 6.17588 | 207.652 |
| T014292 | Control | 652 | 0.13233 | 6.1765 |
| T014292 | Control | 736 | 0.174175 | 5.8594 |
| E016924 | Control | 164 | 0.167034 | 5.6364 |
| E016924 | Control | 290 | 0.328866 | 40.6502 |
| E016924 | Control | 505 | 1.04181 | 44.1978 |
| E016924 | Control | 769 | 2.71096 | 52.3656 |
| E016924 | Control | 911 | 0.6683 | 35.682 |
| E016924 | Control | 1131 | 4.38507 | 127.3354 |

The above data demonstrate the reverse correlation of *E. coli* phages and *E. coli*, suggesting that the depletion of *E. coli* was a result of *E. coli* prophage induction.

The obtained data revealed previously overlooked particularities of phagobiota in T1D, suggesting the primary role of prophages induction in *E. coli* depletion and association with seroconversion in patients who would develop T1D.

Example 7: Role of Prophage Induction in the Release of Amyloid from *E. coli* Biofilms This example demonstrates that the death of *E. coli* populations could be due to prophage induction that leads to T1DAMP production. We used 48h old *E. coli* biofilms formed by amyloid-producing *E. coli* VT-55. Bacteriophages λ (from our collection) were employed. *E. coli* lysogenic strains were obtained by infection of host bacteria with phage. Prophages were induced with 1 µg/ml mitomycin C (Sigma). To confirm lytic development of bacteriophage we measured an increase in the number of plaque forming units (PFU) and the reduction of bacterial colony-forming units CFU numbers, throughout the 4 h to 10 h period (Table 2). The PFU number in *E. coli* biofilm was determined by the production of plaques on control *E. coli* culture.

TABLE 11A

Effect of prophage induction in MG1655 wild-type
lysogenic strain on PFU numbers.

| Probe | PFU/ml | | | |
|---|---|---|---|---|
| | 4 h | 6 h | 8 h | 10 h |
| E. coli Control | 0 | 0 | 0 | 0 |
| E. coli + Mytomicin C | 2.3log10 +/− 0.2log10 | 9.3log10 +/− 0.5log10 | 10.4log10 +/− 0.6log10 | 11.2log10 +/− 0.5log10 |

TABLE 11B

Effect of prophage induction in MG1655 wild-type lysogenic
strain on CFU numbers.

| Probe | CFU/ml | | | |
|---|---|---|---|---|
| | 4 h | 6 h | 8 h | 10 h |
| E. coli Control | 9.3log10 +/− 0.6log10 | 8.9log10 +/− 0.5log10 | 9.1log10 +/− 0.6log10 | 9.5log10 +/− 0.6log10 |
| E. coli + Mytomicin C | 8.8log10 +/− 0.4log10 | 8.2log10 +/− 0.7log10 | 7.6log10 +/− 0.7log10 | 7.4log10 +/− 0.7log10 |

The data demonstrate the appearance of phages in the biofilm starting from 4h following prophage induction and with the maximum number of PFU at 10h that coincides with the decrease of CFU.

Next, the effect of prophage induction on E. coli biofilm to amyloid release was evaluated. The amount of amyloid fibers in the biofilm supernatant was determined following prophage induction. Biofilm supernatant was collected and centrifuged at 5000 rpm (Eppendorf 5113) to sediment cells. Supernatant was filtered with 0.25 mM filter and heated to eliminate contaminating proteins by incubating in a boiling water bath for 10 minutes, under the assumption that the aggregated β-sheet amyloid is heat resistant. To quantify the amount of aggregated amyloid, its binding to the amyloid diagnostic dye Congo Red (CR) was evaluated (Table 12). CR added to a final concentration of 10 μg/mL at pH 4.5 was tested using a BioRad UV/Vis spectrophotometer at 25° C. After 5 minutes of equilibration, the absorbance spectra were recorded from 400 to 600 nm. Each trace represents the average of 3 accumulated spectra.

TABLE 12

Effect of prophage induction on the release of
bacterial amyloid from biofilm

| Wavelength (nm) | E. coli + Mytomicin C (prophage induction) | E. coli control |
|---|---|---|
| 400 | 0 | 0 |
| 450 | 0.156 | 0.083 |
| 500 | 0.338 | 0.104 |
| 541 | 0.421 | 0.137 |
| 550 | 0.345 | 0.096 |
| 600 | 0.015 | 0.009 |

Data received demonstrated significant spectral change in CR absorbance upon binding to heated supernatant 10h following prophage induction compared with control probes and CR alone, with maximum difference in absorbance between CR bound to amyloid fibers at ~541 nm. Data demonstrate that following E. coli death due to the pro-phages induction there is a significant release in bacterial amyloid that in turn trigger seroconversion.

Example 8: Study of Correlation Between HLA
Haplotype and E. coli Presence and Disappearance The correlation between the certain HLA haplotype, and the presence or disappearance of E. coli prior to the seroconversion was studied. The HLA types of the patients referred to in Tables 7 and 8 above were determined and listed below, along with whether E. coli were present or disappeared prior to seroconversion.

TABLE 13

The association of HLA allele, seroconversion and
E. coli disappearance.

| ID | Group | HLA Type | E. coli presence/ disappearance |
|---|---|---|---|
| T025418 | T1D | -DQA1*0201/*03-DQB1*02/*0302-DRB1*0404 | Disappearance Disappearance |
| E010937 | T1D | -DQA1*05/*03-DQB1*02/*0302-DRB1*0401 | Disappearance Disappearance |
| E006574 | T1D | -DQB1*0302/*0501-DRB1*0401 | Disappearance |
| E003251 | T1D | -DQB1*0302/*0501-DRB1*0401 | Disappearance |
| E003989 | Seroconverter | -DQB1*0302/*04-DRB1*0401 | Presence |
| E010629 | Seroconverter | -DQB1*0302/*0501-DRB1*0401 | Disappearance* |
| E017751 | Seroconverter | -DQA1*05-DQB1*02/*0604 | Presence |
| E018113 | Seroconverter | -DQB1*0302/*04-DRB1*0401 | Disappearance* |
| E022137 | Seroconverter | -DQB1*0302/*0501-DRB1*0401 | Disappearance* |
| E026079 | Seroconverter | -DQB1*0302/*04-DRB1*0401* | Disappearance* |
| T013815 | Seroconverter | -DQA1*05/*0201-DQB1*02/*02 IAA | Presence |
| E001463 | Control | -DQB1*0302/*04-DRB1*0401 | Presence |
| E006547 | Control | -DQB1*0302/*0501-DRB1*0404 | Presence |
| E006673 | Control | -DQA1*05/*03-DQB1*02/*0302-DRB1*0401 | Presence Presence |
| E010590 | Control | -DQB1*0302/*04-DRB1*0401 | Presence |
| E018268 | Control | -DQB1*0302/*0604-DRB1*0404 | Presence |
| E022852 | Control | -DQB1*0302/*0501-DRB1*0404 | Presence |
| T014292 | Control | -DQA1*05/*03-DQB1*02/*0301 | Presence |
| E016924 | Control | -DQA1*05-DQB1*02/*04 | Presence |

Data received demonstrate that the following HLA alleles DQB1*02/*0302-DRB1*0404 and DQB1*0302/*0501-DRB1*0401, DQB1*0302/*04-DRB1*0401* had the highest association with seroconversion and significant alteration of E. coli abundance.

Example 9: Autoimmunity Development is
Associated with an Alteration in
Amyloid-producing Bacterial Abundance To explore the potential link between the abundance of amyloid-producing bacteria and T1D-associated seroconversion, longitudinal shotgun metagenomics sequencing data of the fecal microbiome from 10 children who exhibited autoantibodies (six seroconverters and four children who developed T1D) and eight non-seroconverted HLA-matched control individuals was used. Data was also used from a prospective, longitudinal cohort study by Kostic et al. of 16 HLA-matched infants followed from birth until 3 years of age (Kostic et al., 2015). The children, from Finland and Estonia, were recruited to the study between September 2008 and August 2010 (available at http://www.diabimmune.org/). The study generated shotgun metagenomics sequencing data of the fecal microbiome from 10 children who exhibited autoantibodies (six who developed serum autoantibodies with no progression to T1D, and four who were seroconverted and developed T1D) and eight non-seroconverted control individuals (Kostic et al., 2015). Inclusion criteria were: presence of HLA DR-DQ alleles associated with T1D development. Data on diabetes-associated autoantibodies are presented in the original study. HiSeq-2500 sequencing was performed on a sample from each individual, producing an average of ~2.5 Gb per sample.

High-throughput shotgun sequencing was performed on the Illumina HiSeq 2500 platform, generating ~2.5 Gb of sequence per sample with 101-bp paired-end reads. Human contamination was removed with the BMTagger (ftp://ftp.ncbi.nlm.nih.gov/pub/agarwala/bmtagger/). Bacterial and phage contents were quantified separately using the SRA shotgun metagenomic sequencing data. Bacterial content was quantified by taxa directly from SRA reads using Metaphalan (v. 2.0), which maps sequence reads to a database of predefined clade-specific marker genes (Segata et al., 2012). All bacterial taxa with relative abundances <0.01 in all samples were excluded from statistical analysis. Phage content was assessed using a custom method. First, reads from each SRA file were assembled de novo into contigs with metaSPAdes (v. 3.11.1) (Nurk et al., 2017). Then, contigs >200 bp were aligned to the EBI collection of phage genomes (https://www.ebi.ac.uk/genomes/phage.html) by BLAST, with a threshold e-value <1e-5 and alignment length >50% of contig length. All of the original reads were then re-mapped with Bowtie2 (v. 2.3.4.1) to the contigs with good phage BLAST matches in order to increase sensitivity and to more accurately count the abundance of reads from each type of phage (Langmead and Salzberg, 2012). Phage read counts per contig were combined per phage genome (taxa) and normalized to relative abundance. A detection threshold of two reads per sample (>90% identity to the phage genome) was used, based on a previous report (Hao et al., 2018).

Statistical analysis of the microbial community composition and differential abundance was undertaken. The QIIME pipeline (v1.9.1) was used for quality filtering of bacterial and bacteriophage DNA sequences, chimera removal (with USEARCH software), taxonomic assignment, and calculation of a-diversity, as previously described (Caporaso et al. 2010; Tetz et al., 2017). Downstream data analysis and calculation of diversity metrics were conducted in R v3.5.1, using ggplot2 and phyloseq libraries; DESeq2 was used to calculate logarithm of fold change. Bacterial and bacteriophage communities at the genus, family, and species levels were characterized based on α- and β-diversities. α-Diversity indices (ACE, Chao 1 richness estimator, Shannon and Simpson indexes) were calculated using the phyloseq R library (McMurdie and Holmes, 2013). Differences in a-diversities between datasets were examined by the Mann-Whitney test; $p<0.05$ was considered statistically significant.

Differences among groups where two variables exist (phenotype and time point) were analyzed by two-way ANOVA and Tukey's multiple comparison test. When one variable was compared, an unpaired two-tailed t-test was used. Data were visualized using multidimensional scaling (MDS).

Correlations between E. coli disappearance, Bifidobacterium abundance, breastfeeding and antibiotic usage were assessed pairwise using the Jaccard similarity index (Jaccard, 1912). Differences were considered statistically significant at $p<0.05$.

Amyloid-producing bacteria were represented by E. coli, Staphylococcus aureus, and Salmonella spp. (Barnhart and Chapman 2006; Schwartz and Boles 2013). Among these amyloid-producing bacteria, E. coli was the major group, while the other curli-producing bacteria were identified only in a single sample and only at a few collection times and thus were disregarded in subsequent analysis, as indicated in the following list of all phages identified in this study: Escherichia Stx1-converting recombinant phage HUN/2013;

Escherichia phage Pollock; Escherichia phage phi191; Escherichia phage TL-2011b; Escherichia phage TL-2011c; Escherichia phage HK639; Escherichia phage HK75, ENA|HM173637|HM173637.1 Escherichia phage N15 Escherichia phage HK022

Escherichia phage T; Escherichia phage D108; Escherichia phage K1G; Escherichia phage K1H; Escherichia phage Klind1; Escherichia phage Klind2; Escherichia phage Klind3; Escherichia phage EC6; Escherichia phage 1720a-02; Enterobacteria phage cdtl; Enterobacteria phage P2; Enterobacteria phage HK97 Enterobacteria phage Mu; Enterobacteria phage 933W; Enterobacteria phage P7; Enterobacteria phage VT2-Sakai proviral DNA; Enterobacteria phage AR1; Enterobacteria phage phiP27; Enterobacteria phage BP-4795; Enterobacteria phage RB10; Enterobacteria phage P88;

Enterobacteria phage JenP1; Enterobacteria phage 9g; Enterobacteria phage mEpX1; Enterobacteria phage mEp460, Enterobacterial phage mEp390; Enterobacteria phage mEp237; Enterobacteria phage mEp235; Enterobacterial phage mEp234; Enterobacterial phage mEp213; Enterobacteria phage mEp043 c-1; Enterobacteria phage HK106;

Enterobacteria phage HK140; Enterobacteria phage HK225; Enterobacteria phage HK446; Enterobacteria phage HK542; Enterobacteria phage HK544, Enterobacteria phage HK630; Enterobacteria phage HK633; ENA|xEnterobacteria phage mEpX2, Enterobacteria phage IME10, Enterobacteria phage IME10, Enterobacteria phage lambda, Enterobacteria phage 2851, Enterobacteria phage YYZ-2008, Enterobacteria phage DE3, Enterobacteria phage phi80, Bacteriophage P4, Bacteriophage 186; Bacteriophage If1; Stx2-converting phage 86; Stx2 converting phage I DNA, Stx2 converting phage II DNA, Stx2-converting phage 1717, Stx2 converting phage vB_EcoP_24B.

Figure 4:
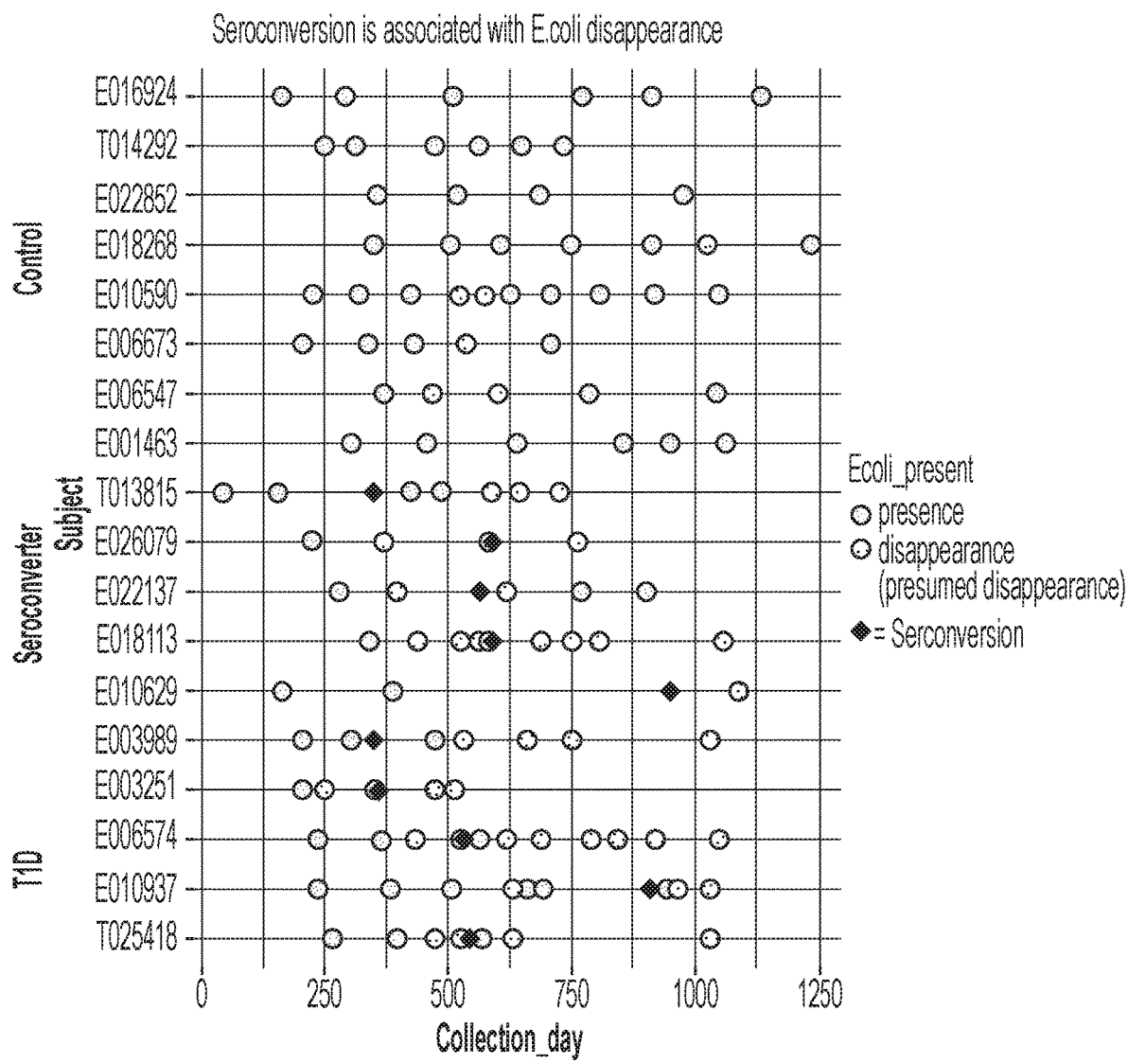
FIG. 4 shows the association between the dynamics of the disappearance of E. coli and seroconversion. Each row represents an individual, with each symbol indicating a single stool sample. The X-axis indicates age at sample collection. E. coli abundance is >0.01. The light gray circles indicate presence of E. coli, and the dark gray circles indicate disappearance or presumed disappearance (over 50-fold reduction when compared with initial abundance) of E. coli. Diamonds represent the time point at which autoantibodies were detected.

The association between E. coli abundance, disease phenotype, and collection time were first compared using a two-tailed Mann-Whitney U test (FIG. 4). The samples were clustered into time-point bins of 300 days, and the dynamics of E. coli abundance were studied over 1300 days within and among patient groups. E. coli abundances demonstrated a different dynamic relationship across time for case and control groups. E. coli tended to disappear in T1D and seroconverters over the time, whereas in controls, E. coli abundance tended to increase and did not change significantly over time. In both the seroconverter and T1D groups (case groups), a statistically significant decrease in E. coli abundance was found when comparing the first 0-300 day period and the following 300-600, 600-900, 900-1300 time bins (p<0.05). Notably, the initial abundance of *E. coli* was significantly higher in cases than in controls at 0-300 days. The case groups responded differently over time, and importantly, data from the control group revealed that there was no variation in *E. coli* associated with age.

Figure 2A:
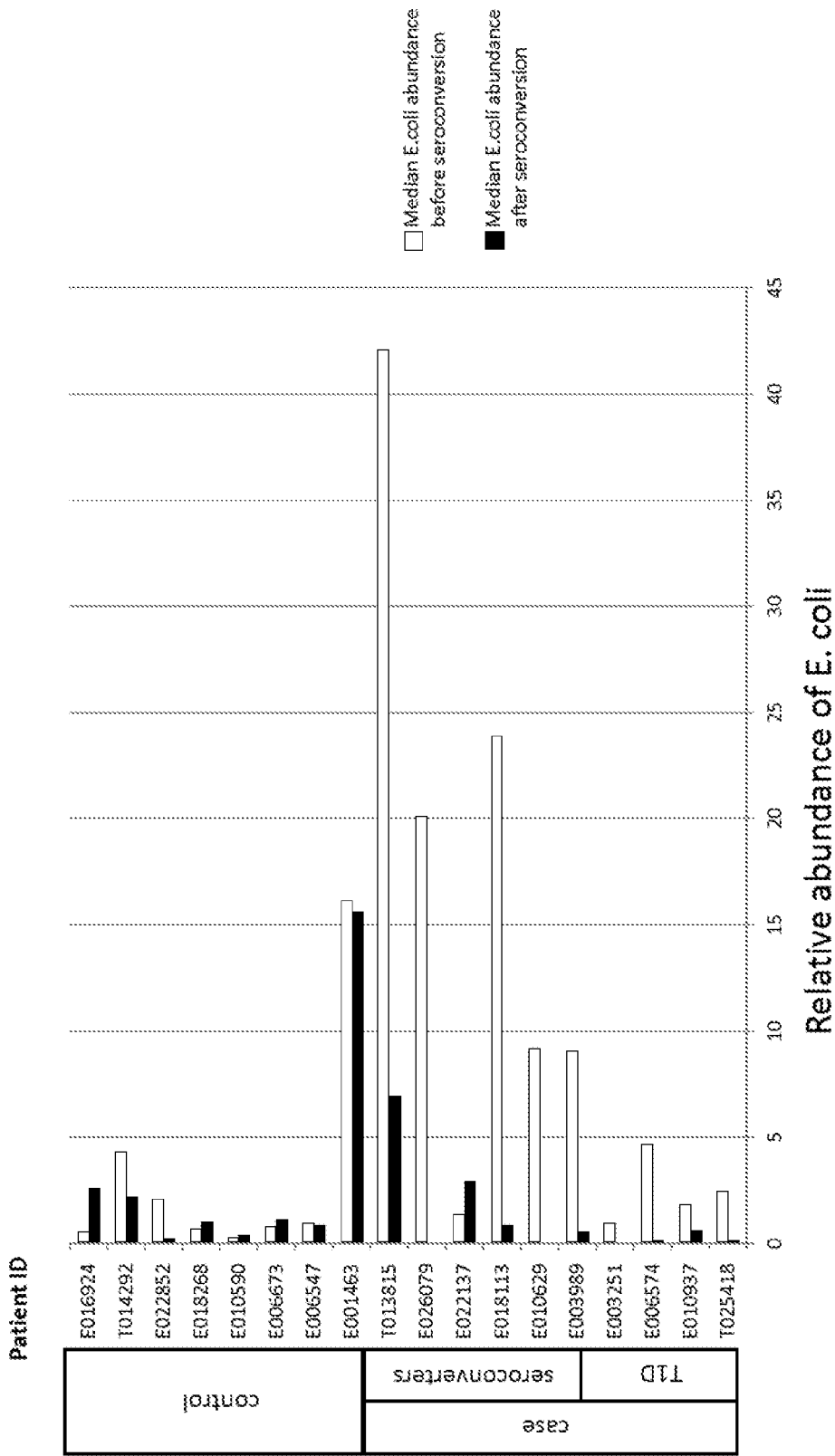
FIGS. 2A and 2B show a difference in the abundance of E. coli before and after seroconversion across groups.
Figure 2B:
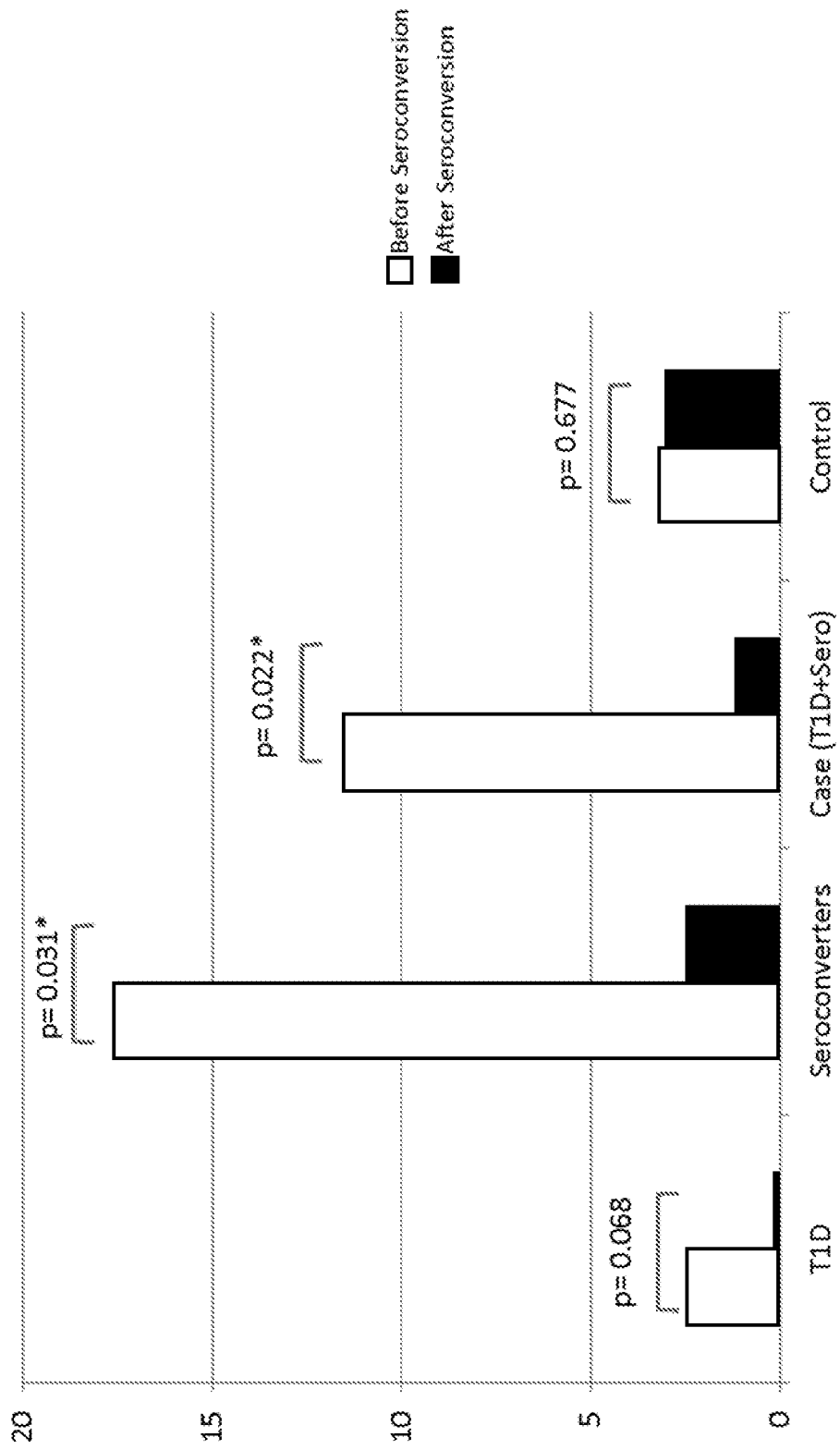

To further define the *E. coli*-related association with autoimmunity, an analyses of paired sample sets comparing the *E. coli* abundance before and after appearance of the autoantibodies across groups was next conducted, with the results shown in FIGS. 2A-2B. For the control group the inventors modulated the time of seroconversion using an artificial benchmark of the medium time to seroconversion in case groups that was 540 days (Table 14).

TABLE 14

Association of disappearance of *E. coli* and development of seroconversion and/or T1D

| Patient # | Case | Age of seroconversion (days) |
|---|---|---|
| T025418 | T1D | 540 |
| E010937 | T1D | 905 |
| E006574 | T1D | 533 |
| E003251 | T1D | 358 |
| E003989 | seroconverter | 347 |
| E010629 | seroconverter | 945 |
| E018113 | seroconverter | 588 |
| E022137 | seroconverter | 562 |
| E026079 | seroconverter | 580 |
| T013815 | seroconverter | 350 |
| E001463 | control | N/A |
| E006547 | control | N/A |
| E006673 | control | N/A |
| E010590 | control | N/A |
| E018268 | control | N/A |
| E022852 | control | N/A |
| T014292 | control | N/A |
| E016924 | control | N/A |

Three of four T1D patients showed a disappearance of *E. coli* prior to the detection of autoantibodies. One patient (E010937) from T1D group who retained the presence of *E. coli* following seroconversion showed over a 60-fold decrease in *E. coli* abundance between the first sample collection and the first sample after seroconversion, demonstrating a dramatic drop in the *E. coli* population (FIG. 5A). The same trend was noted in Seroconverters group with total disappearance of *E. coli* or a trend to the decrease of its abundance prior to the detection of autoantibodies. The only patient who had higher *E. coli* abundance following detected autoantibodies was E022137; however, this patient had a total *E. coli* disappearance before seroconversion with a restoration of *E. coli* abundance in the following time periods.

When the absolute abundance of *E. coli* sequences was compared "before" and "after" the appearance of antibodies within a subgroups (FIG. 2B), only Case (combing both Seroconvertors and T1D) and Seroconvertors groups have reached statistically significance (p=0.022 and p=0.031) (FIG. 2B). In T1D group, although the abundance of *E. coli* was lower following the autoantibodies appearance in all children, the difference was not statistically significant (p=0.068), most likely due to a smaller sample group size.

There was no correlation between the abundance of *E. coli* in control groups and the appearance of autoantibodies (p=0.677). The result further supports that the decrease of amyloid-producing bacteria abundance in T1D group was likely to be associated with disease and not with an age change.

Figure 6:
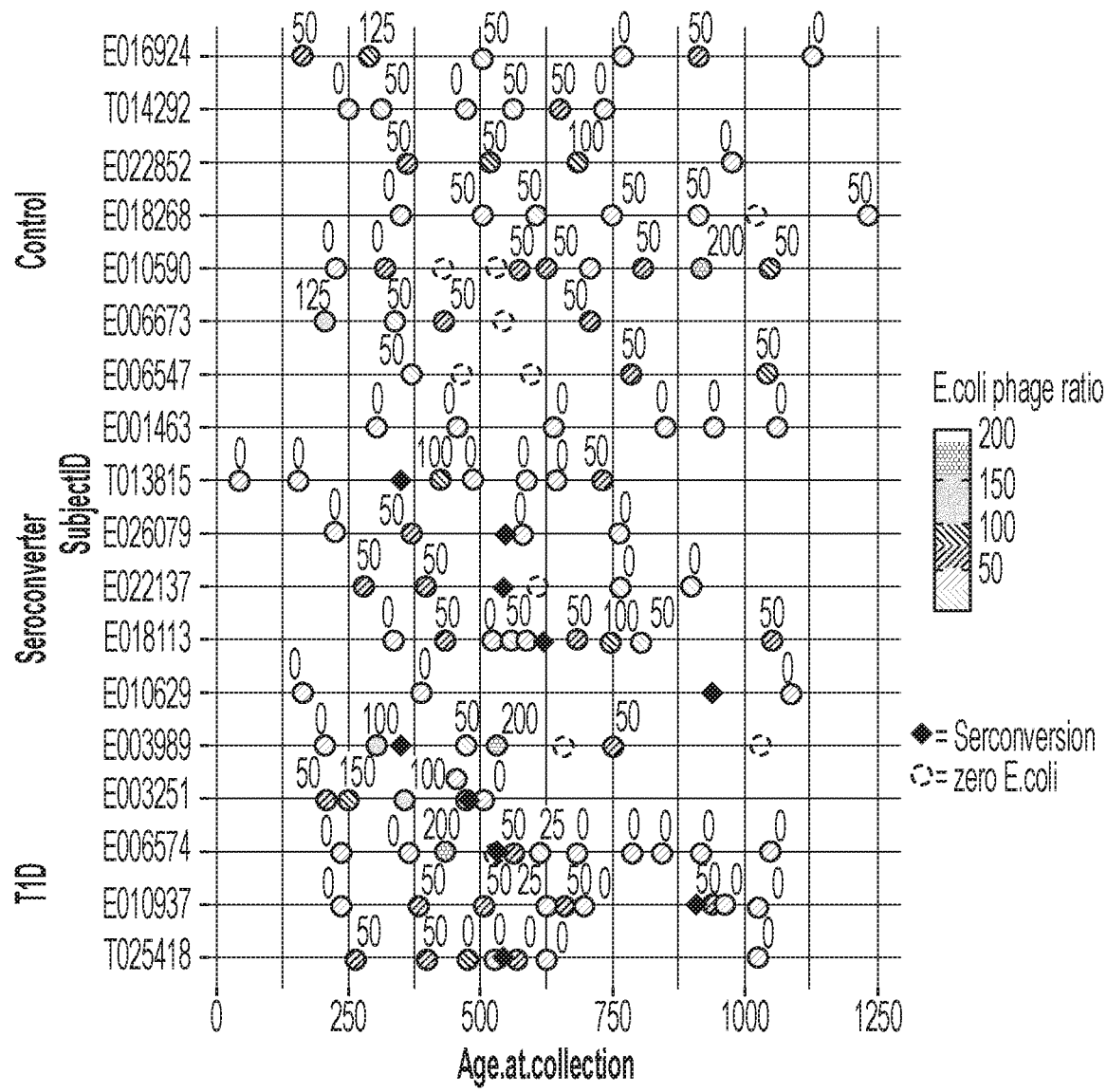
FIG. 6 shows the association between E. coli phage/E. coli ratio across samples and seroconversion. Each row represents an individual, with each symbol representing the phage/bacterial ratio, calculated as E. coli phage abundance normalized to that of the E. coli abundance, of a sample. Abundance is represented by values ranging from zero (lowest ratio) to 200 (maximum ratio) next to each circle. Samples in which E. coli phages but no bacterial cells were present are marked with white circles. Samples with total E. coli disappearance or presumed disappearance with over 50-fold decrease in E. coli are indicated by circles. The X-axis indicates age at sample collection. The diamond symbol represents the time point at which seroconversion was detected.

To explore the relation between *E. coli* abundance and autoimmunity further, the inventors next analyzed whether alterations in the abundance of *E. coli* could be associated with the development of autoantibodies in more detail, and whether or not *E. coli* abundance could distinguish the T1D disease state. To this end, the appearance and disappearance of *E. coli* was studied in each patient in dynamic association with the appearance of autoantibodies (FIG. 6). A positive correlation was found between the total disappearance or presumed disappearance (defined as a >50-fold decrease) in *E. coli* and autoantibody appearance in the T1D and seroconverter groups, but not in controls. All T1D patients showed disappearance or an episode of disappearance of *E. coli* before the detection of autoantibodies, and disappearance of *E. coli* prior to the diagnosis of diabetes (Table 14). In seroconverters, *E. coli* disappeared in all patients, except E003989 and T013815. For patient E10629, data were difficult to interpret because of the long period between sample collections (556 days between the last sample taken before seroconversion and the first sample after seroconversion). In any case, *E. coli* was absent in the first sample following seroconversion; thus, it is reasonable to assume that it had disappeared before autoantibody appearance. Notably, in certain control patients, *E. coli* disappeared at some time points; however, this was followed by a restoration of the *E. coli* population in all cases, which was not regularly seen in case subjects.

Figure 3:
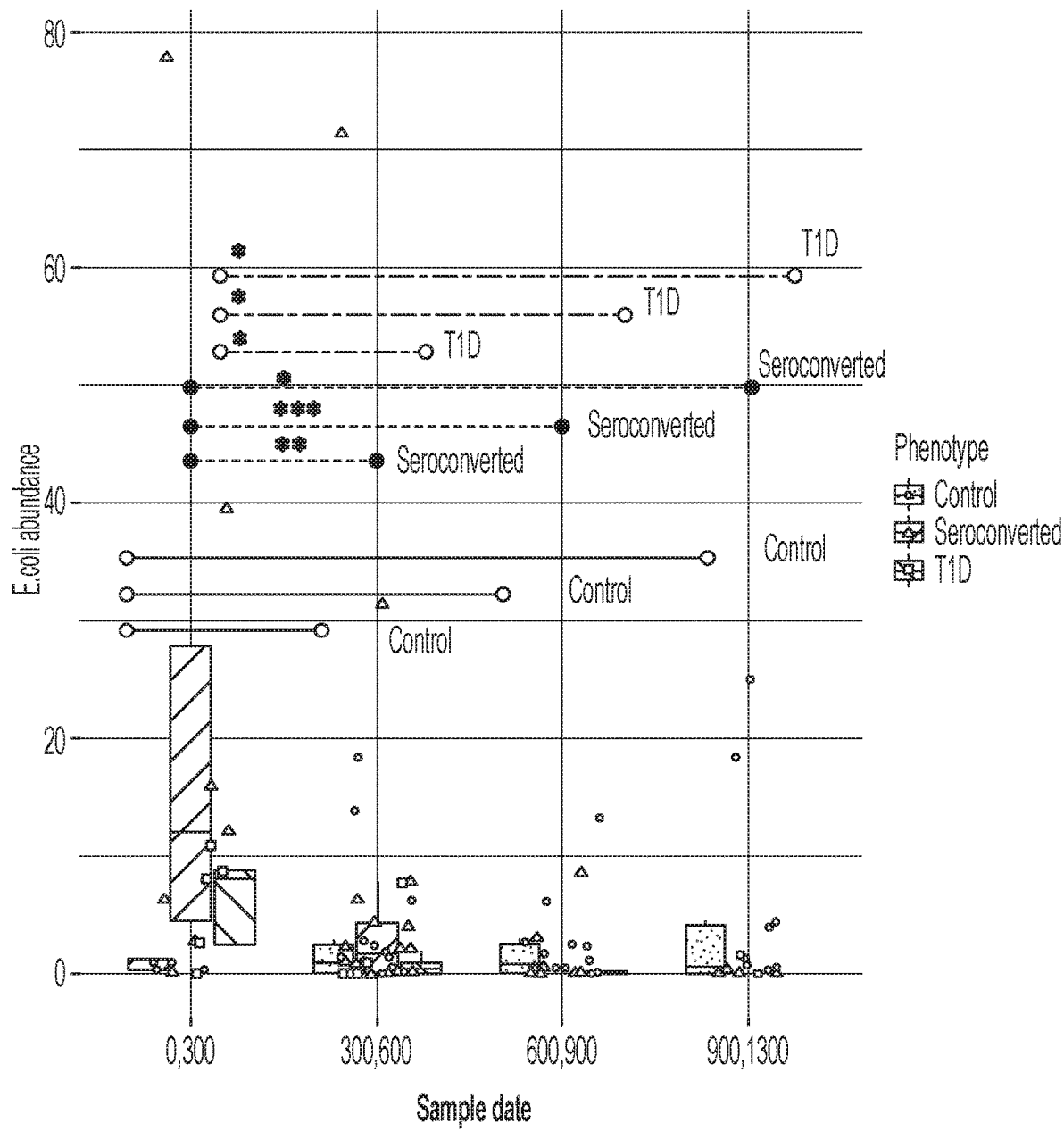
FIG. 3 shows a comparison of the abundance of E. coli across different samples. Faecal bacterial communities were analysed by high-throughput Illumina Hiseq2000 sequencing. The plots show the relative abundance of the E. coli for each group at different time periods. E. coli abundance across different time points was compared using two-tailed Mann-Whitney U test. Statistically significant variation between selected conditions (*p<0.05, p<0.01 and *p<0.005). Each of the four columns (0, 300; 300, 600; 600, 900; and 900, 1300) shows three boxes. The left box corresponds to controls, the middle box to seroconverters, and the right box to T1D. The small dots correspond to individual samples while the horizontal lines correspond to species averages.
Figure 5:
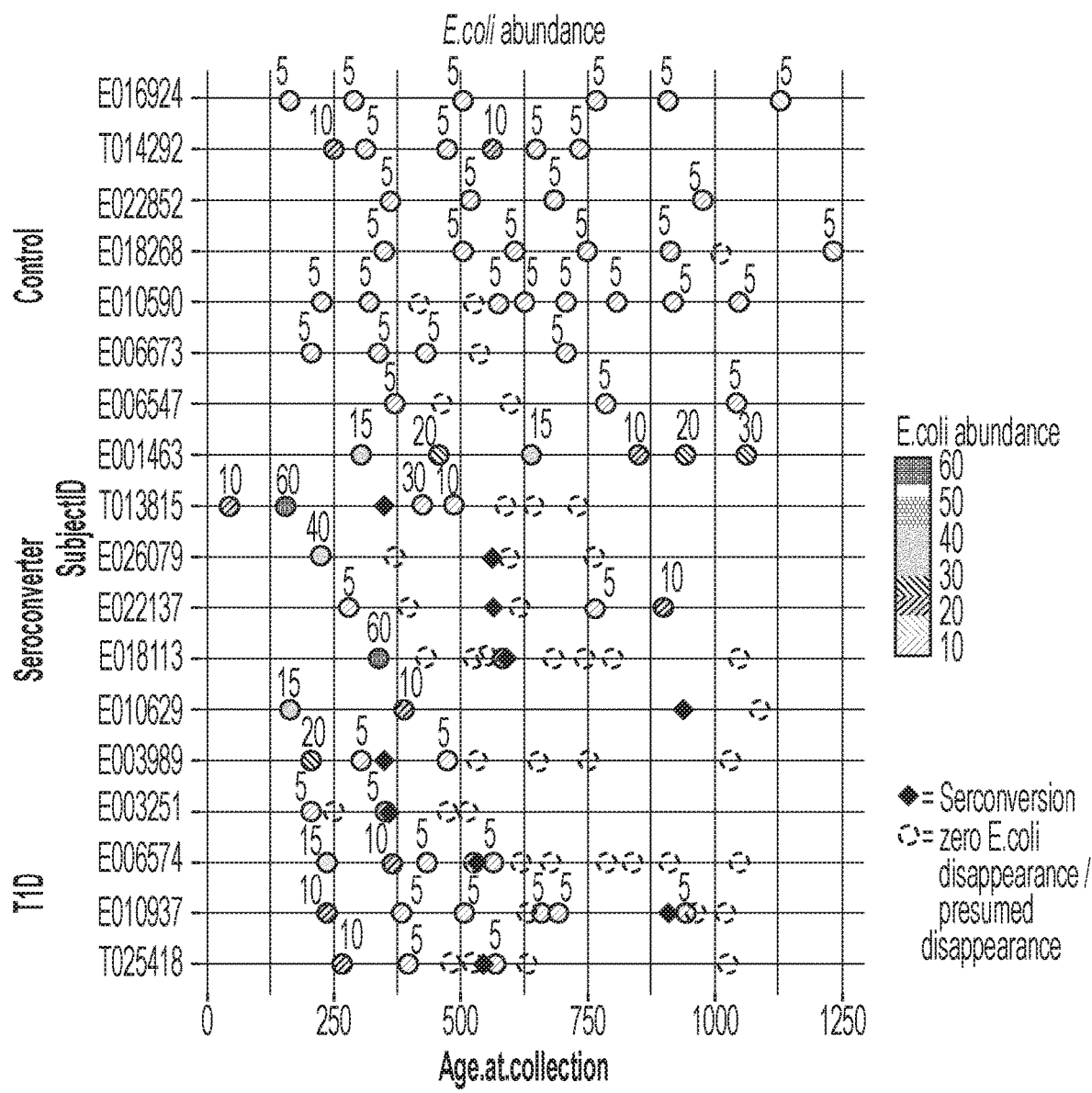
FIG. 5 shows the absolute abundances of E. coli across samples. Fecal bacterial communities were analyzed by high-throughput Illumina Hiseq2500 sequencing. Threshold for E. coli abundance is >0.01. Each row represents an individual, with E. coli abundance in each stool sample (indicated with different symbols) indicated with an approximate value from 5 to 60, ranging from zero (low abundance) to 60 (maximum abundance) next to each circle. Samples with no E. coli are marked with white circles. The X-axis indicates age at sample collection. The diamond sign represents the time of seroconversion detected.

Next, changes in the absolute abundance of *E. coli* were examined in each patient individually among different periods, with the data presented as a heatmap in FIG. 5. Alterations in *E. coli* abundance were detected within children from the control group, followed by restoration of the *E. coli* population to the levels equal to or above the pre-seroconversion levels, whereas restoration of the *E. coli* population to preceding levels was noted in only a few children from the case groups. This more detailed analysis has also revealed that in patient T013815, although *E. coli* did not disappear prior to the seroconversion, the appearance of autoantibodies occurred during the period when *E. coli* started to significantly decrease from the highly elevated abundance compared to other patients. Notably, the initial abundance of *E. coli* in T1D and seroconverter groups was significantly higher than that in the control group, which confirmed the data presented in FIG. 3. These results suggest that the initial higher abundance of *E. coli* and the decrease of amyloid-producing bacteria abundance in case groups were signatures associated with autoimmunity and disease progression.

In addition, the inventors studied the potential correlation between the disappearance of *E. coli* and certain HLA alleles or the appearance of particular autoantibodies, IAA, GADA, IA2A, ZNT8A or ICA, in case groups. No correlations were observed (data not shown). No association was detected between *E. coli* disappearance and breastfeeding duration, *Bifidobacterium* abundance, or antibiotic usage, which are known to influence Enterobacteriaceae (Candela et al., 2008).

Example 10: *E. coli* Bacteriophages as Signatures Associated with Seroconversion As identified were *E. coli* as T1D-discriminative bacteria, the relationships between this microorganism and bacteriophages of *E. coli* were then studied, as phages are known as main regulators of bacterial populations. First, 63 *E. coli* phage species were detected in case and control groups. Possible differences in *E. coli* phages were evaluated using a- and β-diversities in the pre-seroconversion period. For the samples from the control group, the medium time to seroconversion in case groups (540 days) was set as an artificial benchmark. Phage richness was statistically different between control and seroconversion individuals as indicated by ACE and Chao1 indexes (ACE: p=0.0181; Chao1: p=0.0137), but was not statistically significantly different between control and T1D, most likely because of the small T1D patient cohort (ACE: p=0.6086; Chao1: p=0.6359). *E. coli* phage diversity tended to be lower in the control subjects than in seroconverters (Shannon, p=0.1526; Simpson, p=0.5437), and was significantly lower in controls vs. T1D cases (Shannon, p=0.0055; Simpson, p=0.0248) (Mann-Whitney test).

Nearly all *E. coli* phages were observed to be lysogenic, whereas strictly virulent lytic phages, such as Enterobacteria phage IME10 or Enterobacteria phage 9g, were found only in a few samples. The predominance of lysogenic *E. coli* phages clarifies why a-diversity indices revealed trends of decreased evenness and diversity of phages in case groups compared to controls in pre-seroconversion samples, which most likely reflected lower *E. coli* abundance in controls.

Next, the *E. coli* phage/*E. coli* bacterial cell ratio, which represents the "lytic potential" (FIG. 6) (Waller et al., 2014), was analyzed. *E. coli* strain MG1655 was used as a host for prophage induction experiments (Jensen 1993). Bacteria were subcultured from freezer stocks onto Mueller-Hinton agar plates (Oxoid) and incubated at 37° C. overnight. All subsequent liquid subcultures were derived from colonies isolated from these plates and were grown in Mueller-Hinton broth (Oxoid). Bacteriophage λ from the inventors' collection was employed. Bacteriophage suspensions were routinely stored in TM buffer (10 mM Tris-HCl, 10 mM $MgSO_4$, pH 7.2) at 4° C. *E. coli* lysogenic strains were obtained by infection of *E. coli* MG1655 with the phage and titration of cells on Mueller-Hinton agar plates as previously described (Maniatis et al. 1989). For prophage induction, Mitomycin C (Sigma-Aldrich) was prepared in 0.1 M phosphate buffer (pH 7.2), filtered through a 0.22-μm-pore filter (Millipore Corp., Bedford, Mass.), and stored at 4° C. (Georgopoulos et al., 2002). A modified protocol according to Reyrolle et al. designed for prophage induction on 96-well plates was used (Reyrolle et al., 1982; McDonald et al., 2010). Twenty microliters of an overnight *E. coli* MG1655 culture, with an absorbance at 600 nm of 0.2, was dispensed in each well of a 96-well flat-bottom polystyrene tissue culture microtiter plate (Sarstedt, Numbrecht, Germany), after which 180 μl of MHB (Oxoid) was added. The plates were incubated at 37° C. for 48 h. Induction of prophages in the *E. coli* biofilms was provoked by the addition of mitomycin C (Sigma) to a final concentration 1 μg/ml to each well. The plates were further incubated at 37° C. and samples were taken at 4, 6, 8, and 10 h following prophage induction.

To this end, the *E. coli* phage abundance was first normalized to that of *E. coli*. In theory, the phage/bacteria ratio reflects whether or not a prophage is stably integrated within the host bacterial genome (Tetz et al., 2018). A low ratio indicates that prophage is most likely absent in the genomes of part of the bacterial host population, whereas a high ratio suggests active, productive phage-induced bacterial lysis. The phage/bacteria ratio increased in subjects from all groups prior to the decrease in *E. coli* abundance, indicating that productive phage infection was the cause of *E. coli* depletion. Notably, a statistically significant elevation in the phage/bacteria ratio was observed before the appearance of autoantibodies in the T1D and seroconverter groups.

To evaluate the implication of the increase in the phage/bacteria ratio as a driving force behind *E. coli* depletion further, the inventors analyzed which phages had a correlation with the depletion of *E. coli* abundance across most subjects. The most frequently found lysogenic phages with an inverse relationship with *E. coli* abundance are representatives of the Peduovirinae subfamily and of the unclassified Lambdavirus subfamily within the Caudovirales order, as shown in Tables 15 and 16 below.

TABLE 15

| phage id | order | family | subfamily | genus |
|---|---|---|---|---|
| phage1 | Caudovirales | Myoviridae | N/A | Muvirus |
| phage2 | Caudovirales | Myoviridae | Peduovirinae | |
| phage3 | Caudovirales | Myoviridae | Tevenvirinae | |
| phage4 | Caudovirales | Myoviridae | unclassified Myoviridae | |
| phage5 | Caudovirales | Podoviridae | Sepvirinae | Nona33virus |
| phage6 | Caudovirales | Podoviridae | Sepvirinae | T12011virus |
| phage7 | Caudovirales | Podoviridae | unclassified Podoviridae | P22virus |
| phage8 | Caudovirales | Podoviridae | unclassified Podoviridae | *Escherichia* phage phi191 sensu lato |
| phage9 | Caudovirales | Podoviridae | unclassified Podoviridae | |
| phage10 | Caudovirales | Podoviridae | N/A | Epsilon15virus |
| phage11 | Caudovirales | Siphoviridae | Guernseyvirinae | K1gvirus |
| phage12 | Caudovirales | Siphoviridae | Lambdavirus | *E. coli* lambda |
| phage13 | Caudovirales | Siphoviridae | Lambdavirus | unclassified Lambdavirus |
| phage14 | Caudovirales | Siphoviridae | Nonagvirus | |
| phage15 | Caudovirales | Siphoviridae | unclassified Siphoviridae | |
| phage16 | Inoviridae | unassigned Inoviridae | | |
| phage17 | unclassified *E. coli* viruses | | | |

TABLE 16

P values for *E. coli* phage/*E. coli* ratio by Fisher's exact test

| phage id | Phenotype | p value | phage id | Phenotype | p value |
|---|---|---|---|---|---|
| phage1 | all | 0.34283 | phage3 | Control | 1 |
| phage2 | all | 0.000159 | phage4 | Control | 1 |
| phage3 | all | 1 | phage5 | Control | 0.02498 |
| phage4 | all | 0.117281 | phage6 | Control | 1 |
| phage5 | all | 1.11E-07 | phage7 | Control | 1 |
| phage6 | all | 0.038959 | phage8 | Control | 0.162409 |
| phage7 | all | 0.117233 | phage9 | Control | 1 |
| phage8 | all | 0.000259 | phage10 | Control | 0.02229 |
| phage9 | all | 1 | phage11 | Control | 1 |
| phage10 | all | 1.53E-05 | phage12 | Control | 0.001707 |
| phage11 | all | 1 | phage13 | Control | 0.003943 |
| phage12 | all | 2.24E-07 | phage14 | Control | 1 |
| phage13 | all | 3.86E-10 | phage15 | Control | 1 |
| phage14 | all | 0.117233 | phage16 | Control | 0.314373 |
| phage15 | all | 0.0776 | phage17 | Control | 0.191851 |
| phage16 | all | 0.038959 | phage1 | Seroconverted | 1 |
| phage17 | all | 1.53E-05 | phage2 | Seroconverted | 0.155795 |
| phage1 | Control | 1 | phage3 | Seroconverted | 1 |
| phage2 | Control | 0.347588 | phage4 | Seroconverted | 1 |
| phage5 | Seroconverted | 0.049274 | phage12 | T1D | 0.007511 |
| phage6 | Seroconverted | 1 | phage13 | T1D | 5.26E-06 |
| phage7 | Seroconverted | 1 | phage14 | T1D | 0.491935 |
| phage8 | Seroconverted | 1 | phage15 | T1D | 0.3547 |
| phage9 | Seroconverted | 1 | phage16 | T1D | 0.491935 |
| phage10 | Seroconverted | 0.141163 | phage17 | T1D | 0.001252 |
| phage11 | Seroconverted | 1 | | | |
| phage12 | Seroconverted | 0.06885 | | | |
| phage13 | Seroconverted | 0.03751 | | | |

TABLE 16-continued

P values for E. coli phage/E. coli ratio by Fisher's exact test

| phage id | Phenotype | p value | phage id | Phenotype | p value |
|---|---|---|---|---|---|
| phage14 | Seroconverted | 1 | | | |
| phage15 | Seroconverted | 0.315225 | | | |
| phage16 | Seroconverted | 1 | | | |
| phage17 | Seroconverted | 0.133539 | | | |
| phage1 | T1D | 1 | | | |
| phage2 | T1D | 0.00159 | | | |
| phage3 | T1D | 0.491935 | | | |
| phage4 | T1D | 0.491935 | | | |
| phage5 | T1D | 0.000389 | | | |
| phage6 | T1D | 0.052489 | | | |
| phage7 | T1D | 1 | | | |
| phage8 | T1D | 0.001252 | | | |
| phage9 | T1D | 1 | | | |
| phage10 | T1D | 0.018926 | | | |
| phage11 | T1D | 1 | | | |

The increase in number of the lysogenic *E. coli* phages along with the decrease in *E. coli* abundance indicated that there was a productive bacteriophage infection that led to bacterial host death and the release of phage progeny. These data revealed previously overlooked particularities of the phagobiota in T1D, suggesting a primary role of induction of certain *E. coli* prophages in *E. coli* depletion, and an association with autoimmunity and T1D development.

Example 11: Role of Prophage Induction in the Release of Amyloid from *E. coli* Biofilms The inventors evaluated how the die-off of *E. coli* populations due to prophage induction could lead to amyloid release. The inventors used 48-h old *E. coli* biofilms with confirmed curli expression. Curli formation on 48-h colonies was visible with the naked eye on petri dishes (data not shown). Prophages were induced with mitomycin C. Lytic bacteriophage development was confirmed as an increase in plaque forming units (PFU) and a reduction in colony-forming units (CFU).

CFU and PFU were determined as follows. To estimate CFU, biofilms were thoroughly scraped (Tetz et al., 2009). Well contents were aspirated, placed in 1 ml of isotonic phosphate buffer (0.15 M, pH 7.2), and the total CFU number was determined by serial dilution and plating on Mueller-Hinton agar. The number of phage virions produced after induction was estimated by phage titration (using strain MG1655 as a host) and phage plaque assay. Following induction, at the indicated times 200-μl samples of biofilms were collected. Then, 30 μl of chloroform was added to each sample, the mixture was vortexed and centrifuged at 3000×g for 5 min in a microcentrifuge (Eppendorf 5415D). A supernatant fraction of the bacterial lysate was further used. The phage titer (number of phages per ml) was determined using the double agar overlay assay method as described previously (Yuan et al., 2012). To this end, 2.5 μl of each titration point of phage lysate was spotted on Mueller-Hinton agar (Oxoid). Then, a mixture of 1 ml of *E. coli* MG1655 culture and 2 ml of 0.7% nutrient agar (heated to 45° C.) supplemented with $MgSO_4$ and $CaCl_2$) (to a final concentration of 10 mM each) was poured over the plate. Plates were incubated at 37° C. overnight. Each experiment was repeated in triplicate.

The presence of phage in *E. coli* biofilm was confirmed by the production of plaques on a non-induced *E. coli* control culture between 4 h and 10 h. The effect of prophage induction in *E. coli* biofilm on CFU and PFU is summarized in Table 17.

TABLE 17

Effect of prophage induction in MG1655 wild-type lysogenic strain on PFU and CFU

| | PFU/ml | | | | CFU/ml | | | |
|---|---|---|---|---|---|---|---|---|
| | 4 h | 6 h | 8 h | 10 h | 4 h | 6 h | 8 h | 10 h |
| E. coli control | 0 | 0 | 0 | 0 | 9.3 log10 +/− 0.6 log10 | 8.9 log10 +/− 0.5 log10 | 9.1 log10 +/− 0.6 log10 | 9.5 log10 +/− 0.6 log10 |
| E. coli + mytomicin C | 2.3 log10 +/− 0.2 log10 | 9.3 log10 +/− 0.5 log10 | 10.4 log10 +/− 0.6 log10 | 11.2 log10 +/− 0.5 log10 | 8.8 log10 +/− 0.4 log10 | 8.2 log10 +/− 0.7 log10 | 7.6 log10 +/− 0.7 log10 | 7.4 log10 +/− 0.7 log10 |

Phages started to appear in the biofilm as of 4 h after prophage induction, with maximum PFU at 8 h, which coincided with a decrease in CFU.

Next, the inventors evaluated the effect of prophage induction on the amount of amyloid fibers released into the biofilm supernatant. Supernatant CR depletion assays were performed as follows. The amount of bacterial amyloid following prophage induction was measured in the supernatant of *E. coli* MG1655 biofilms. Biofilms were obtained as described above. Biofilm supernatant was taken at 4, 6, 8, and 10 h following prophage induction. To isolate aggregated amyloid fibers from the supernatant, the supernatant was centrifuged at 10,000×g, filtered through a 0.22 μm filter to separate bacterial cells, and treated with proteinase K to eliminate contaminating proteins. CR (Sigma-Aldrich) was added to a final concentration of 10 μg/ml from a filtered stock solution of 1 mg/ml (Reichhardt et al., 2015). After 5 min of equilibration, absorbance spectra were recorded from 400 to 600 nm (SmartSpec 3000, Bio-Rad). Each trace represents the average of 5 accumulated spectra. For all samples, spectra of corresponding nutrient MHB solutions with CR were used as blanks.

Figure 7:
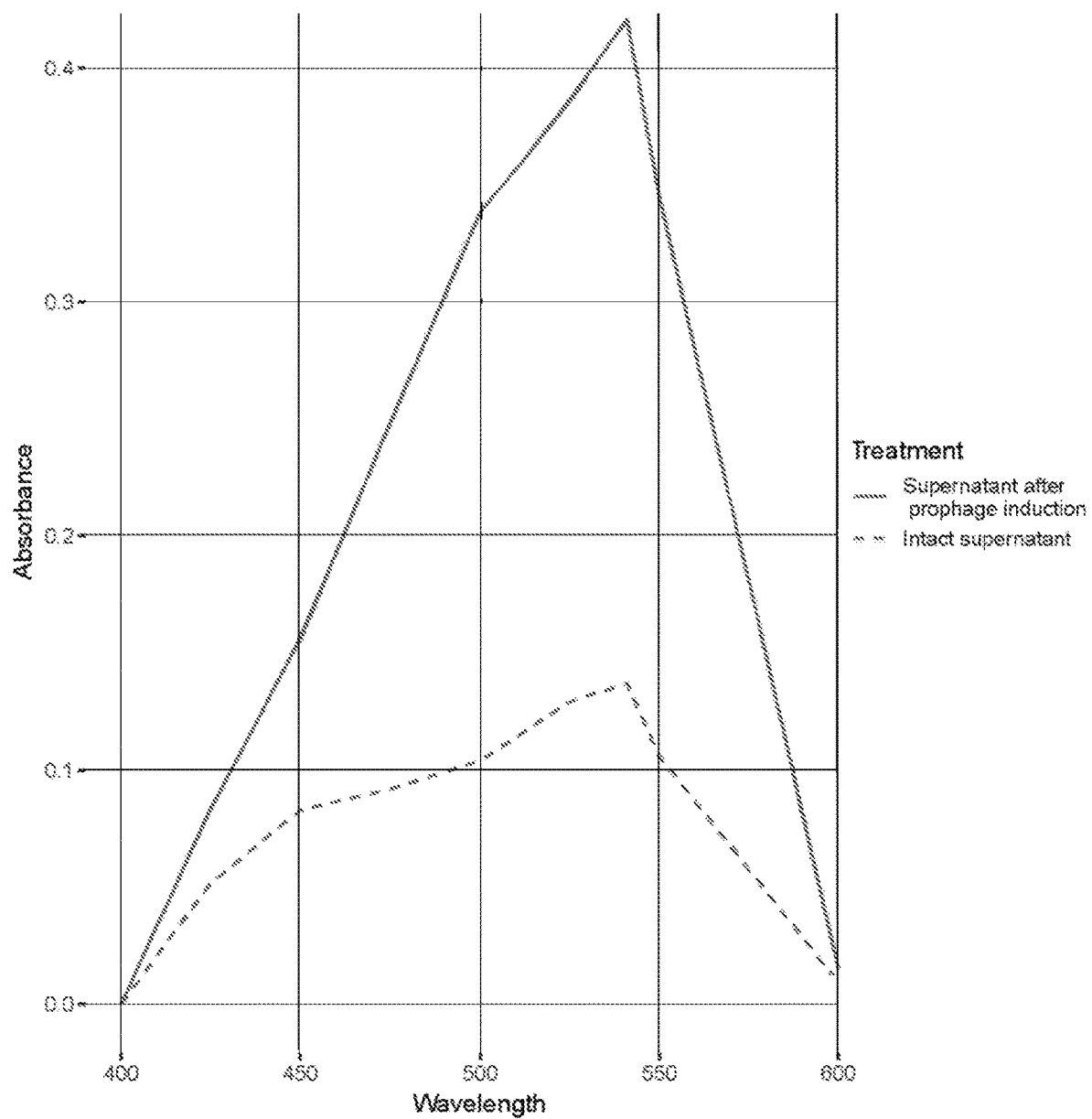
FIG. 7 shows that prophage induction promotes amyloid release from E. coli in vitro. CR absorbance upon binding to amyloid from intact E. coli supernatant (dashed line) and from E. coli supernatant after prophage induction (solid line). Both curves are approximately equal to zero at the isosbestic point (403 nm), and the maximum difference in absorbance was observed at 541 nm. Both spectra were normalized to the absorbance spectrum of free CR.

To quantify the amount of aggregated amyloid, its binding to the amyloid-diagnostic dye was evaluated by a Congo red (CR) assay (Reichhardt et al., 2015). A significant increase in CR absorbance was observed upon binding to supernatant 8 h following prophage induction as compared with control samples (FIG. 7). Like for other curli fibers, heating of the *E. coli* supernatant induced a spectral shift of the CR solution, with a maximum difference in absorbance between CR alone and CR bound to amyloid fibers at ~541 nm (Chapman et al., 2002). These data suggested that the phage-mediated lysis of *E. coli* led to the release of amyloid aggregates into the biofilm.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

REFERENCES

1. Bosi E, Molteni L. Radaelli M G, Folini L. Fermo I, Bazzigaluppi E, Piemonti L, Pastore M R, Paroni R. Increased intestinal permeability precedes clinical onset of type 1 diabetes. Diabetologia. 2006 Dec. 1; 49(12): 2824-7.
2. Vaarala O, Atkinson M A, Neu J. The "perfect storm" for type 1 diabetes: the complex interplay between intestinal microbiota, gut permeability, and mucosal immunity. Diabetes. 2008 Oct. 1; 57(10):2555-62.
3. Macs M, Kubera M, Leunis J C, Berk M. Increased IgA and IgM responses against gut commensals in chronic depression: further evidence for increased bacterial translocation or leaky gut. Journal of affective disorders. 2012 Dec. 1; 141(1):55-62.
4. Tlaskalová-Hogenová, Helena, Renata Štěpánková, Hana Kozáková, Tomáš Hudcovic, Luca Vannucci, Ludmila Tučková, Pavel Rossmann et al, "The role of gut microbiota (commensal bacteria) and the mucosal barrier in the pathogenesis of inflammatory and autoimmune diseases and cancer: contribution of germ-free and gnotobiotic animal models of human diseases," *Cellular & molecular immunology* 8, no. 2 (2011): 110,
5. Berk M, Williams L I, Jacka F N, O'Neil A. Pasco J A, Moylan S, Allen N B, Stuart A L, Hayley A C, Byrne M L, Macs M. So depression is an inflammatory disease, but where does the inflammation come from? BMC medicine. 2013 December; 11(0:200.
6. Fasano A, Zonulin, regulation of tight junctions, and autoimmune diseases. Annals of the New York Academy of Sciences. 2012 Jul. 1; 1258(1):25-33.
7. Costerton J W, Stewart P S, Greenberg L. P. Bacterial biofilms: a common cause of persistent infections. Science. 1999 May 21; 284(5418):1318-22.
8. Barnhart M M, Chapman M R. Curti biogenesis and function. Annu. Rev. Microbiol. 2006 Oct. 13; 60:131-47.
9. Noble J A. Valdes A M. Genetics of the HLA region in the prediction of type 1 diabetes. Current diabetes reports. 2011 Dec. 1; 11(6):533.
10. Knip M, Veijola R, Virtanen S M, Hyöty H, Vaarala O, Åkerblom H K. Environmental triggers and determinants of type 1 diabetes. Diabetes. 2005 Dec. 1; 54(suppl 2):S125-36.
11. Gallo, P M et al., Amyloid-DNA composites of bacterial biofilms stimulate autoimmunity. Immunity. 2015, 42(6): 1171-1184.
12. Kostic A D et al., The dynamics of the human infant gut microbiome in development and in progression toward type 1 diabetes. Cell Host Microbe. 2015, 17(2):260-273.
13. Segata, N et al., The dynamics of the human infant gut microbiome in development and in progression toward type 1 diabetes. Nat, Methods. 2012, 9(8):811-814,
14. Caporaso, J G et al., QIIME allows analysis of high-throughput community sequencing data. Nat. Methods, 2010, 7(5):335-336.
15. Cox, L et al., Altering the intestinal microbiota during a critical developmental window has lasting metabolic consequences. Cell, 2014, 158(4):705-721.
16. Love, M et al., Moderated estimation of fold change and dispersion for RNA-seq data with DESeq2. Genome Biol., 2014, 15(12):550.
17. Edgar, R et al., Search and clustering orders of magnitude faster than BLAST. Bioinformatics, 26(19):2460-2461.
18. McMurdie, P J and Holmes, S, phyloseq: an R package for reproducible interactive analysis and graphics of microbiome census data, PLoS One, 2013, 8(4):e61217.
19. Schwartz, K and Boles, B R, Microbial amyloids—functions and interactions within the host. 2013, 16(1): 93-99.
20. Tetz, G V et al., Effect of RNase and antibiotics on biofilm characteristics. 2009, 53(3):1204-1209.
21. Reichhardt, C et al., Congo Red Interactions with Curli-Producing *E. coli* and Native Curti Amyloid Fibers. PLoS One, 2015, 10(10):e0140388.
22. Chapman, M R et al, Role of *Escherichia coli* curli operons in directing amyloid fiber formation. Science, 2002, 2950556):851-855,
23. Yuan, Y et al., Genome characteristics of a novel phage from *Bacillus thuringiensis* showing high similarity with phage from *Bacillus cereus*. PLoS One, 2012, 7(5): e37557.
24. Waller, A S et al., Classification and quantification of bacteriophage taxa in human gut metagenomes. ISME J., 2014, 8(7):1391-1402.
25. Jensen, K F, The *Escherichia coli* K-12 "wild types" W3110 and MG1655 have an rph frameshift mutation that leads to pyrimidine starvation due to low pyrE expression levels. J. Bacteriol., 1993, 175(11):3401-3407.
26. Reyrolle, J et al., Lysogenic strains of lactic Acid streptococci and lytic spectra of their temperate bacteriophages. Appl. Environ. Microbiol., 1982, 43(2):349-356.
27. McDonald, J E et al., High-throughput method for rapid induction of prophages from lysogens and its application in the study of Shiga Toxin-encoding *Escherichia coli* strains. Appl. Environ. Microbiol., 2010, 76(7):2360-2365.
28. Tetz, G et al, Parkinson's disease and bacteriophages as its overlooked contributors. Sci. Rep., 2018, 8(410812.
29. Candela M et al., Plasminogen-dependent proteolytic activity in *Bifidobacterium lactis*, Microbiology, 2008, 154:2457-2462.

The invention claimed is:

1. A method for determining susceptibility to type 1 diabetes (T1D) in a mammal, said method comprising:
   a) determining the level of amyloid-producing Escherichia coli (E. coli) bacteria in gastrointestinal microbiota of the mammal,
   b) comparing the level determined in step (a) to a corresponding control level in mammal(s) from an age-matched and/or gender-matched reference population, and
   c) determining that the mammal is susceptible to T1D, when the level of said amyloid-producing E. coli bacteria in gastrointestinal microbiota of the mammal is increased as compared to the control level.

2. The method of claim 1, wherein the amyloid-producing E. coli bacteria release a T1D-associated microbial product (T1DAMP) that enters the bloodstream of the mammal.

3. The method of claim 2, wherein T1DAMP is selected from an amyloid protein, a bacterial amyloid protein, an amyloid-like protein, a bacterial amyloid curli protein, an amyloid precursor, a bacterial curli, an amyloid-DNA complex, an amyloid-nucleic acid complex, and a bacterial DNA.

4. The method of claim 1, wherein the mammal is human, and the method step (a) comprises determining the level of said amyloid-producing E. coli bacteria in gastrointestinal microbiota of the mammal at 0-300 days after birth of the human.

5. The method of claim 1, further comprising determining the expression in the mammal of at least one T1D susceptible HLA allele.

6. The method of claim 5, wherein the T1D susceptible HLA allele is selected from an HLA allele having a DR4-DQ8 haplotype, an HLA allele having a DR3-DQ2 haplotype, HLA allele DQB1*02/*0302-DRB1*0404, HLA allele DQB1*0302/*0501-DRB1*0401, and HLA allele DQB1*0302/*04-DRB1*0401*.

7. The method of claim 1, wherein determining the level of the amyloid-producing E. coli bacteria comprises performing one or more of the assays selected from i) analysis of 16S rRNA, ii) PCR, iii) sequencing, iv) a metagenomic assay, v) cultivation, and vi) biochemical identification.

8. The method of claim 1, wherein the method comprises:
   a)(i) determining the level of said amyloid-producing E. coli bacteria in gastrointestinal microbiota of the mammal at an earlier time point followed by (ii) determining the level of said amyloid-producing *E. coli* bacteria in gastrointestinal microbiota of the mammal at a later time point,
b) comparing the levels determined in steps (a)(i) and (a)(ii) to each other and to corresponding control levels in mammals from an age-matched and/or gender-matched reference population, and
c) determining that the mammal is susceptible to T1D, when the level of said amyloid-producing *E. coli* bacteria in gastrointestinal microbiota of the mammal is increased at the earlier time point followed by a substantial depletion in the level or the total disappearance of said amyloid-producing *E. coli* bacteria in gastrointestinal microbiota of the mammal at the later time point.

9. The method of claim 8, wherein the mammal is human, the earlier time point is at 0-300 days after birth of the human and the later time point is between 9 months and 30 months after birth of the human.

10. A method for determining susceptibility to type 1 diabetes (T1D) in a mammal, said method comprising:
a) determining the amount of T1D-associated microbial product (T1DAMP) in feces, saliva, blood, Cerebrospinal fluid (CSF) and/or tissue(s) from the mammal,
b) comparing the amount of T1DAMP determined in step (a) to a corresponding control amount in mammals from an age-matched and/or gender-matched reference population, and
c) determining that the mammal is susceptible to T1D, when the amount of T1DAMP determined in step (a) is increased as compared to the control amount.

11. The method of claim 10, wherein the T1DAMP is selected from an amyloid protein, a bacterial amyloid protein, an amyloid-like protein, a bacterial amyloid curli protein, an amyloid precursor, a bacterial curli, an amyloid-DNA complex, an amyloid-nucleic acid complex, and a bacterial DNA.

* * * * *

SEQUENCE LISTING

<160> NUMBER OF SEQ ID NOS: 15

<210> SEQ ID NO 1
<211> LENGTH: 9077
<212> TYPE: DNA
<213> ORGANISM: Mus musculus

<400> SEQUENCE: 1

| | | | | | |
|---|---|---|---|---|---|
| ctaatctccc | taggcaaggt | tcatatttgt | gtaggttact | tattctcctt | ttgttgacta | 60 |
| agtcaataat | cagaatcagc | aggtttggag | tcagcttggc | agggatcagc | agcctgggtt | 120 |
| ggaaggaggg | ggtataaaag | ccccttcacc | aggagaagcc | gtcacacaga | tccacaagct | 180 |
| cctgacagga | tggcttccct | tcgactcttc | ctcctttgcc | tcgctggact | ggtatttgtg | 240 |
| tctgaagctg | gccccgcggt | gagtgatcct | gtgagcgatc | cagacatggc | agttagacct | 300 |
| tagataaaga | agaagtgcct | tcttccagat | gtgagaacta | gagtactcag | actctatatt | 360 |
| taccattaga | ctccaaagag | aagagctgga | gtgcctctgg | ctcttccttc | tattgcttta | 420 |
| gcgcattggg | tctgtagtgc | tcagtctctg | gtgtccttag | ataataaaga | tatgagatta | 480 |
| acatagaaat | aaagatataa | aagggctgga | tgtatagttt | agtggtccag | tgtatgccta | 540 |
| gtatgtgaaa | agccttctgt | tcaacctcta | gcaatagaaa | aacaagatat | attctcggtg | 600 |
| gggctgttaa | tattgaattc | tcataaaatc | tttaatatat | ttagtatgcc | tattatgttg | 660 |
| ttatatttta | gttctttagc | taatcaaaat | gcattattga | tctttctttg | tcttttttg | 720 |
| gccaacactc | tattccagtc | tttgaaaaag | tcctttaaaa | gagttaatca | gtataattaa | 780 |
| atgagtcagg | aagtatgtga | gggttatttt | acaaccagag | ggaattacta | tagcaacagc | 840 |
| tgattagaat | gatctcaaga | aaaagcccat | tctgtctttt | tgcaccatgc | acctttcagt | 900 |
| ggctccattc | agatggagag | gcaaacagag | caatggctct | cagagggcct | attttccctt | 960 |
| tgaacattca | ttatccatat | ccctggtgca | cagcagtgca | tctgggggca | gaaactgttc | 1020 |
| ttgctttgga | aacaatgctg | tctatgtcat | actggataaa | gaagctcatt | aattgtcaac | 1080 |
| acttatgtta | tcataatggg | atcagcatgt | acttttggtt | ttgttccaga | gtctatcacc | 1140 |
| ggaaagaaca | agccggttta | ctctgaccca | tttcactgac | atttctcttg | tctcctctgt | 1200 |
| gcccagggtg | ctggagaatc | caaatgtcct | ctgatggtca | aagtcctgga | tgctgtccga | 1260 |
| ggcagccctg | ctgtagacgt | ggctgtaaaa | gtgttcaaaa | agacctctga | gggatcctgg | 1320 |
| gagccctttg | cctctgggta | agcttgtaga | aagcccacca | tgggaccggt | tccaggttcc | 1380 |
| catttgctct | tattcgtgtt | agattcagac | acacacaact | taccagctag | agggctcaga | 1440 |
| gagagggctc | aggggcgaag | ggcacgtatt | gctcttgtaa | gagacacagg | tttaattcct | 1500 |
| agcaccagaa | tggcagctca | taaccatctg | aaactcacag | tcttaggaga | tctgggtatc | 1560 |
| tgacattctc | ttctacccac | catgtgtgtg | gtgcacaaat | tcacatgcag | gcatcaaatc | 1620 |
| ttataaacaa | caacaaaaaa | ccaacaaacc | tggtagcaaa | agaagattag | aaggttaaac | 1680 |
| atatgagccg | agagcttttg | tttttgtttg | ttttgttttg | tttttgtttac | atttcaaatg | 1740 |
| ttatcccctt | tctcggtccc | cctccccaaa | ccctctaccc | cattctctcc | tccccttctt | 1800 |
| ctatgagggt | gttccccacc | aacccactcc | caccttcctg | ctctcgaatt | ccctatact | 1860 |
| gggacatcaa | gccttcacag | aatcaagggc | ctctcctccc | attgatgccc | gacaatgtca | 1920 |
| tcctctgcta | cctatgtggc | tggagccatg | ggtcccttca | tgtatcctcc | ttggttggtg | 1980 |
| gtttagtctc | tgggaggtct | gggggatctg | gttgattgat | attattgttc | ttcctatgag | 2040 |
| attgcaaacc | ccttcagctc | cttcggtcct | ttaactcctc | cactggggac | cccgagctca | 2100 |

```
gtccaatggt tggctgtgag catccaccag cagaggcctt ttttttttt tttaacaaag    2160 ctgctttatt atgttgctta gagcatgacc aggaaccaga gcacagtcca agactgaagg    2220
gaggaaaagg gggggagtca ataacccac tgtttcatag tggtttgcaa ccctttata    2280 tcacagccca ctttaggcaa ataatgaaaa ttatagtctc cagggacaga gaagatggtg    2340
caggaagtga agtgcctgct cagaaaatgg gggcttgaat gtgagttccc agactctgtg    2400
taagatgccc agcatcgaag tgcatgctta aacaccagc ctggaggtag aagcttagaa    2460
acaggggtac cctgaagttg cttgttcacc agtgtccctg aatgggtagg tgcatgtttg    2520
gtgagagacc ctgtctcaaa atcaaggtg taggataatt gaaataccct agctttgagc    2580
ttagatcatg caaatgtgta cacacactca cacacaccac acacacaaaa aaatgcagag    2640
acagagagat acagagagac agagagatac agagacagag acagagagaa aaggagaaag    2700
taaaaaacaa ataatttaaa gacccatggc cacaaagagg ctcaaagaca agcacgtata    2760
aaaccataca catgtaattt taggagtttt cagattccct ggtacccgtg ggtgatgcac    2820
aagctttgaa tcccagtctt aaaatcttac gaagaacgtg ttcgtgtgtg ctaatttatt    2880
gatgagagga aaggaattga caaagtgccc ttccggagct tcctgcatta cccagactca    2940
gggttttttt aaatgtacac tcagaacaga gtagctctgt gcaagggtag caaccacgaa    3000
gcttaataag aaacatatcg tgagagatct gcaaggcaaa tctaggggct gaccaatctc    3060
acagtcaccc actagcatgt caacacaact tcccacctgt gctagccact tagcaatttt    3120
gtgttgttct gttttgtttt tgttttttaac aaagcaattt caaagagatt tctaattcat    3180
ctaaacaaac aaaccaaaag gaaaacagca aagacgccct gagcacttag cagagcagct    3240
atgcagttat gactcctggg tggagacttt tatcaggct tcaactgaat acctagaacc    3300
tactagtgct cttcatcaat ccttgggaag gtcattttct tttggtgctg ttttgagttt    3360
ctatttgtta atgtcttcat aattatacac gtgttgagca cagcatgcaa agtgattagg    3420
ggaatctagt tggagtggaa tggatacccca aatattcaga cttctcttgtg actcttcttt    3480 cttgtaccca catcaaaaaa aaaaaaatg gagatgagac atggtcagag tcactaaaac    3540
cagctgctac ttttaattac gtggggagca gtttctaaca ttgccattat tgaactgatg    3600
ctgcctgggt ggaaatggaa atcacttagt atttcttgtt ggcaaagaat tactgaatgg    3660 attaaattc caagggagaa agtcagttac aagtcttttc tttgtttatt aggctttctg    3720
ctatgataaa ttacactact tccagaagtt acccttaggc catgggacac tggactatca    3780
ctctgctgtc acaagagatt acagagttag tcaaggcagc ttgtgacacc ttcagggact    3840
gtcataaact tccagcaagt cattaatcct gaatgcaata ctgtgtgtgt gtgtctatgt    3900
gtgtttgtat gtctgtgtgt gtcttatgtc tgtgtctctg tgtgtgtgtg tgtttgtgtg    3960
tgtgtgtgta tgtatgcctg tgtgtgtctt atgtctgtgt ttgtgtgtct gtgtgtgtct    4020
tatgtctgtg tttgtatgtc tgtgtgtgtc tgtgtgtgtc ttatgtctgt gtctctgtgt    4080
gtgtgtgtgt gtatgtatgt atgtatgtat gtatgtgtat gtgtttgcat ctctctgtgt    4140
gtctgcgctt atatatttgt gtatgtgttt atgtgttcgc ctttgtgcgt tgttggggat    4200
tgaatccagg ggaatacaaa tgttaagaaa gaacgttacc actaagcttc acctgtaggc    4260
cttaaagctt ttcttttcttt taaaaattgt aattaattca ttttcagtca ggatctccac    4320
acctcgtccc tgctgctcta gaactcacta tttaaacaca atcgccctca aacctgcagc    4380
aaccctcccg cctctaccct gcgagcacta gaataataac aggtgacccc acacgcctag    4440
```

```
attaagacct ttaaggtaaa cattttacta tattttagtc tcataagaca agatgctaca    4500
ataaagctgt acataaagtt ccctcgaatt tcttgctatt ttaactcaaa cataaggatt    4560
tcctcctttt tgattcaggt aacagaaaaa atacacaggt acatacatgt acacacatga    4620
acacacacgc atcacaacca catatgcgca cgcttgtgtg atctatcatt taccatgcca    4680
ctgaactctt cttccccat aaattcctct ggacttgtgt gccctccagg aagaccgcgg     4740
agtctggaga gctgcacggg ctcaccacag atgagaagtt tgtagaagga gtgtacagag    4800
tagaactgga caccaaatcg tactggaaga cacttggcat ttccccgttc catgaattcg    4860
cggatgtaag tggacacacc aagttgtttg gattttgttt ttagtctcag gaaattccct    4920
tcgctcttgc tgtacgatgg gcatgagtgg aaagtagatt ccacagccag aatccacagt    4980
gctgggaaag caagccttct gaattttct aaaactcatt tagcaacatg gcctgaacct     5040
gttcacactg cttatggtca gctaactata tttatgtaaa tattcatttc tctgttgagg    5100
aaatgttagt atttgctttt gaggcaacct ccagatacca tggagggcat gtcatagtca    5160
aagagagggc tccctatggt atttctctaa attctgcat ttcctttatt ccaaagcaca     5220
tctagtgtcc ccagaagttt gggtagacaa ttcttggcaa cacagagaat tacaacatgt    5280 tcaaaccca acagcttaat atctaaatca tcaagcaaac atcacatggc aaagggattt     5340
ctgaatcaaa actgtttcat ccttatgatc aacctatgga ggtctagcct cgacttacac    5400 ccatttacc aataagctaa gagaagctaa gttcctcatc aaggacacaa ggctagcatg     5460
tgtgagcaag tgacagagtt gccctctatg ttggttagtg tgccttagcc agtgtctcag    5520
taagaaatgg agctaaatca aacccaagg ccaacagcca aaggcacatg agtaacccttt    5580 gcttggcact gggctcagtt tccctggctc ctctcagtcc tcagttcaca gaggcagctg    5640
tcatgcaaat agaatccaag cttgttggtc agacctggag ataacaaatt ccatcaaaaa    5700
tagctcctca tgtgacctag tttgctgtct gttgctatga tacacaccat gaccgaaaag    5760
caaccctggg gagagaaggg tttatttcat cttacagctt acagttcacc atggaggaaa    5820
gccaggtggg aacctggaag tggaaattga agcagagacc agaaaggaat gctgtttact    5880
ggctggctta gctccttttc ttatacagct taggtctatg tgcccagggg atggtactgc    5940
cgagcatagg ctgagcccgc ctacatcaac cattagtcaa aaaaggtcc atagacttgc     6000 ctacaggcca atctcatgga ggcaatacccc cagtggaggg tccctcttcg caggttactc    6060
tagtttgtgt caagttgaca aaacctaacc acaaagcaca aacagggtct gcccttgtgg    6120
cttagccatg gatgacactc tcagatgatg gtgttaccag acaaaccaga ggggctcacc    6180
aagagtctgc cacctaccaa ggtagtactc tactcctcac tgggcaccaa cacccatatt    6240
agctgggcca gtacaggacc cttgctgttt cctgcatgaa ttgtccatag accctgggtc    6300
tcagcctgcc gggagtacct gtaagtagtc gcctcaaaca cattattcct gttggaagac    6360
ttgtctgatt ctcttttaga actcaatcaa caaacgtttt tattttgttt tggcttttg     6420 gagacaagat ctctcatagg ccagcctgac ttgaatgtag ctgaggatga cctgtgctgc    6480
taatcttctc gcctcttcct cccaagtggt aggataatag gcataagaca ccacagcagt    6540
tttactccat accagggctc tgaacccaga cttaaacac tctatcaact gattcacatt     6600 cccacccat cattcaacaa acatttgaaa aataaaaccc ttctgccttg agcactctgc     6660
taaatacagc ctttgagtgc ggagtatttc ctcacaacca gggtccaaga tgaccccatc    6720
atacatacca cggaaaatta ggagatgttt ttaggtctct ttgcttgggg taattttat     6780 gtgtgtgtgt acacagccct gtgcgtgtgt gtgtgtgtgt gtgtgtgtgt gtacaggcac    6840
```

```
acacgtgtat gcatgtagag gctacataaa aaccttaggt gtcattctca ggcactctgt    6900 tcacccttc acacagcccg aacacacaaa atttgaggca ttagcctgga gctcaccagt     6960
taggctagac tgacttgcca gcagacccca ggctgtctcc atctcccag ctctgggatt     7020 acaaactcta tcataccaga catttttata catattctga gcataaaatt catgtcttca    7080
ggctaacaag tcaagagctt aaatgactga gctctcttac gtggtggatt ttttttaaaa    7140
ctacataata tcttttttt ttttttcact tctggggaag aaacaaatga gcctgagtga     7200
caatgcgaca gaaaagaaat tttgaggagt gtgtgtgtct gtgtgtgtgg tggcacatgc    7260
ctctcatcta atgctagagg ctacagtaga atgctcctga attagtggcc agccaaggcc    7320
aagggctagg gttgtaactc agtggcagag ggcttgccta gcattcgcag gatttgatcc    7380
atagcgctat aaataataat aaataaatac aacagtctaa gatgattctc cctttcattt    7440
atctggatgt tatttttgtg ttagttttac tctgtcatcc aatcattgtt tgccctatat    7500
ttggacattt aaaaaaaatc tttattccaa gtgtgttcaa agctgtatcc aaaacctgtc    7560
caccaaatga gtccaatgac atacatcttc tatattacca tctgttccag atttggctga    7620
ctcccggcac ctgggctgtt gctgcaccca tgtctcagat agtctagtga tttgagaagt    7680
gactagtaat tgcaaaatcc agactttgtc cagaaacttc tatgagctcc aaaactttca    7740
tttacatttc tgccagccac aaaccgcttg tgttgtggag agaaccctgt gatgtcttcc    7800
cacagcatct cagccttgtt tcttccctta aaatattcat cttttcacat tagaacatgc    7860
aaagggacag tgggagcgaa acccctggac tgggacgcac gaagccttcc tttctggtca    7920
ggctctcact gtagaaactt aggccggttt cagcatgcag tctgctggag aatggctcct    7980
gccaacattc caggtctgga agtttgtagt ggagttgttg ataaccactg ttcgccacag    8040
gtcttttgtt tgtgggtgtc agtgtttcta ctctcctgac ttttatctga acccaagaaa    8100
gggaacaata gccttcaagc tctctgtgac tctgatctga ccagggccac ccacactgca    8160
gaaggaaact tgcaaagaga gacctgcaat tctctaagag ctccacacag ctccaaagac    8220
ttaggcagca tattttaatc taattattcg tcccccaacc ccaccccaga ggacagttag    8280
acaataaaag gaagattacc agcttagcat cctgtgaaca ctttgtctgc agctcctacc    8340
tctgggctct gttagaacta gctgtctctc ctctctccta ggtggttttc acagccaacg    8400
actctggcca tcgccactac accatcgcag ccctgctcag cccatactcc tacagcacca    8460
cggctgtcgt cagcaacccc cagaattgag agactcagcc caggaggacc aggatcttgc    8520
caaagcagta gcatcccatt tgtaccaaaa cagtgttctt gctctataaa ccgtgttagc    8580
agctcaggaa gatgccgtga agcattctta ttaaaccacc tgctatttca ttcaaactgt    8640 gtttctttt tatttcctca tttttctccc ctgctcctaa aacccaaaat cttctaaaga    8700
attctagaag gtatgcgatc aaactttta aagaaagaaa atacttttg actcatggtt     8760 taaaggcatc ctttccatct tggggaggtc atgggtgctc ctggcaactt gcttgaggaa    8820
gataggtcag aaagcagagt ggaccaaccg ttcaatgttt tacaagcaaa acatacacta    8880
agcatggtct gtagctatta aaagcacaca atctgaaggg ctgtagatgc acagtagtgt    8940
tttcccagag catgttcaaa agccctgggt tcaatcacaa tactgaaaag taggccaaaa    9000
aacattctga aaatgaaata tttgggtttt ttttataac ctttagtgac taaataaaga     9060
caaatctaag agactaa                                                   9077
```

<210> SEQ ID NO 2

```
<211> LENGTH: 912
<212> TYPE: DNA
<213> ORGANISM: E. coli

<400> SEQUENCE: 2
atgaaacttt taaaagtagc agcaattgca gcaatcgtat tctccggtag cgctctggca      60
ggtgttgttc ctcagtacgg cggcggcggt aaccacggtg gtggcggtaa taatagcggc     120
ccaaattctg agctgaacat ttaccagtac ggtggcggta actctgcact tgctctgcaa     180
actgatgccc gtaactctga cttgactatt acccagcatg gcggcggtaa tggtgcagat     240
gttggtcagg gctcagatga cagctcaatc gatctgaccc aacgtggctt cggtaacagc     300
gctactcttg atcagtggaa cggcaaaaat tctgaaatga cggttaaaca gttcggtggt     360
ggcaacggtg ctgcagttga ccagactgca tctaactcct ccgtcaacgt gactcaggtt     420
ggctttggta caacgcgac cgctcatcag tactaaatga aacttttaaa agtagcagca     480
attgcagcaa tcgtattctc cggtagcgct ctggcaggtg ttgttcctca gtacggcggc     540
ggcggtaacc acgtggtgg cggtaataat agcggcccaa attctgagct gaacatttac     600
cagtacggtg gcggtaactc tgcacttgct ctgcaaactg atgcccgtaa ctctgacttg     660
actattaccc agcatggcgg cggtaatggt gcagatgttg gtcagggctc agatgacagc     720
tcaatcgatc tgacccaacg tggcttcggt aacagcgcta ctcttgatca gtggaacggc     780
aaaaattctg aaatgacggt taaacagttc ggtggtggca acggtgctgc agttgaccag     840
actgcatcta actcctccgt caacgtgact caggttggct ttggtaacaa cgcgaccgct     900
catcagtact aa                                                         912

<210> SEQ ID NO 3
<211> LENGTH: 21
<212> TYPE: DNA
<213> ORGANISM: Artificial sequence
<220> FEATURE:
<223> OTHER INFORMATION: siRNA primer

<400> SEQUENCE: 3
gcccaaattc tgagctgaac a                                                21

<210> SEQ ID NO 4
<211> LENGTH: 21
<212> TYPE: DNA
<213> ORGANISM: Artificial sequence
<220> FEATURE:
<223> OTHER INFORMATION: siRNA primer

<400> SEQUENCE: 4
gcccgtaact ctgacttgac t                                                21

<210> SEQ ID NO 5
<211> LENGTH: 21
<212> TYPE: DNA
<213> ORGANISM: Artificial sequence
<220> FEATURE:
<223> OTHER INFORMATION: siRNA primer

<400> SEQUENCE: 5
gtaactctga cttgactatt a                                                21

<210> SEQ ID NO 6
<211> LENGTH: 21
<212> TYPE: DNA
<213> ORGANISM: Artificial sequence
```

```
<220> FEATURE:
<223> OTHER INFORMATION: siRNA primer

<400> SEQUENCE: 6
ggcggtaatg gtgcagatgt t                                              21

<210> SEQ ID NO 7
<211> LENGTH: 21
<212> TYPE: DNA
<213> ORGANISM: Artificial sequence
<220> FEATURE:
<223> OTHER INFORMATION: siRNA primer

<400> SEQUENCE: 7
gcgctactct tgatcagtgg a                                              21

<210> SEQ ID NO 8
<211> LENGTH: 21
<212> TYPE: DNA
<213> ORGANISM: Artificial sequence
<220> FEATURE:
<223> OTHER INFORMATION: siRNA primer

<400> SEQUENCE: 8
gcgaccgctc atcagtacta a                                              21

<210> SEQ ID NO 9
<211> LENGTH: 456
<212> TYPE: DNA
<213> ORGANISM: E. coli

<400> SEQUENCE: 9
atgaaaaaca aattgttatt tatgatgtta caatactgg gtgcgcctgg gattgcagcc      60
gcagcaggtt atgatttagc taattcagaa tataacttcg cggtaaatga attgagtaag    120
tcttcattta atcaggcagc cataattggt caagctggga ctaataatag tgctcagtta    180
cggcagggag gctcaaaact tttggcggtt gttgcgcaag aaggtagtag caaccgggca    240
aagattgacc agacaggaga ttataacctt gcatatattg atcaggcggg cagtgccaac    300
gatgccagta tttcgcaagg tgcttatggt aatactgcga tgattatcca gaaaggttct    360
ggtaataaag caaatattac acagtatggt actcaaaaaa cggcaattgt agtgcagaga    420
cagtcgcaaa tggctattcg cgtgacacaa cgttaa                              456

<210> SEQ ID NO 10
<211> LENGTH: 21
<212> TYPE: DNA
<213> ORGANISM: Artificial sequence
<220> FEATURE:
<223> OTHER INFORMATION: siRNA primer

<400> SEQUENCE: 10
gcagcaggtt atgatttagc t                                              21

<210> SEQ ID NO 11
<211> LENGTH: 21
<212> TYPE: DNA
<213> ORGANISM: Artificial sequence
<220> FEATURE:
<223> OTHER INFORMATION: siRNA primer

<400> SEQUENCE: 11
ggtcaagctg ggactaataa t                                              21
```

```
<210> SEQ ID NO 12
<211> LENGTH: 21
<212> TYPE: DNA
<213> ORGANISM: Artificial sequence
<220> FEATURE:
<223> OTHER INFORMATION: siRNA primer

<400> SEQUENCE: 12
gattgaccag acaggagatt a                                              21

<210> SEQ ID NO 13
<211> LENGTH: 21
<212> TYPE: DNA
<213> ORGANISM: Artificial sequence
<220> FEATURE:
<223> OTHER INFORMATION: siRNA primer

<400> SEQUENCE: 13
gtgccaacga tgccagtatt t                                              21

<210> SEQ ID NO 14
<211> LENGTH: 21
<212> TYPE: DNA
<213> ORGANISM: Artificial sequence
<220> FEATURE:
<223> OTHER INFORMATION: siRNA primer

<400> SEQUENCE: 14
ggcaattgta gtgcagagac a                                              21

<210> SEQ ID NO 15
<211> LENGTH: 21
<212> TYPE: DNA
<213> ORGANISM: Artificial sequence
<220> FEATURE:
<223> OTHER INFORMATION: siRNA primer

<400> SEQUENCE: 15
gattgaccag acaggagatt a                                              21
```